United States Patent
Schaack

(10) Patent No.: US 6,459,481 B1
(45) Date of Patent: Oct. 1, 2002

(54) SIMPLE SYSTEM FOR ENDOSCOPIC NON-CONTACT THREE-DIMENTIONAL MEASUREMENT

(76) Inventor: David F. Schaack, 1243 Monte Verde Dr. NE., Albuquerque, NM (US) 87112

(*) Notice: Subject to any disclaimer, the term of this patent is extended or adjusted under 35 U.S.C. 154(b) by 0 days.

(21) Appl. No.: 09/565,441

(22) Filed: May 5, 2000

Related U.S. Application Data

(60) Provisional application No. 60/132,908, filed on May 6, 1999.

(51) Int. Cl.$^7$ ............................................... G01N 21/00
(52) U.S. Cl. .................................................. 356/241.1
(58) Field of Search ......................... 356/241.1, 241.3, 356/241.4, 241.5, 241.6, 139.03, 376; 702/95, 153; 700/69, 174

(56) References Cited

U.S. PATENT DOCUMENTS

| | | |
|---|---|---|
| 4,721,098 A | 1/1988 | Watanabe |
| 4,825,259 A | 4/1989 | Berry, Jr. |
| 4,895,431 A | 1/1990 | Tsujiuchi et al. |
| 5,047,848 A | 9/1991 | Krauter |
| 5,432,543 A | 7/1995 | Hasegawa et al. |
| 5,642,293 A | 6/1997 | Manthey |
| 5,748,505 A * | 5/1998 | Greer ..................... 364/571.02 |
| 5,803,680 A | 9/1998 | Diener |
| 5,805,289 A | 9/1998 | Corby, Jr. |
| 6,078,846 A * | 6/2000 | Greer et al. ................. 700/174 |

OTHER PUBLICATIONS

H.M. Karara, ed., Handbook of Non–Topographic Photogrammetry, 1979, pp. 113–115, American Society of Photogrammetary, Falls Church, VA.

(List continued on next page.)

Primary Examiner—Michael P. Stafira
(74) Attorney, Agent, or Firm—Michael Tavella

(57) ABSTRACT

Three-dimensional endoscopic measurements are made by adding an array of reference target points to the scene viewed by an endoscopic camera and characterizing the image formed by the camera when it views the scene from two or more viewing positions. Methods and apparatus are taught which allow one to make accurate measurements with any endoscope, without requiring any modification to the endoscope. Under certain circumstances, the measurements can be made without any pre-calibration of the endoscopic camera.

A general measurement reference apparatus comprises a reference target array which is placed near to and fixed with respect to an object of interest inside an enclosure by means of a reference array holding apparatus and a reference array insertion apparatus. This measurement reference apparatus can be used to make either perspective dimensional measurements or to make conventional photogrammetric measurements of the object of interest.

A general measurement apparatus to be used with the new methods comprises a reference target array which is placed near to and fixed with respect to an object of interest inside an enclosure by means of a reference array holding apparatus and a reference array insertion apparatus. In a version of this apparatus the reference array holding apparatus may attach the reference array directly to the object of interest and the combination may be inserted into the enclosure by the insertion apparatus. The general measurement apparatus also comprises an endoscopic camera located inside the enclosure. The camera is moved with respect to the object by a camera moving apparatus. Images formed by the camera are measured with an image measurement apparatus. These measurements are supplied to a computing apparatus which computes the desired three-dimensional distances. The measurement results are displayed to the user by a display apparatus.

47 Claims, 27 Drawing Sheets

OTHER PUBLICATIONS

Close–Range Photogrammetry & Surveying: State–of–the–Art, 1985, pp. 277–278,416,478, 760–761,871, American Society of Photogrammetry, Falls Church, VA.

K.B. Atkinson, ed., ClosE Range Photogrammetry and Machine Vision, 1996, p. 304, Whittles Publishing, Caithness, KW5 6DW, Scotland, UK.

F.H. Moffitt and E.M. Mikhail, Photogrammetry (3rd. ed.), book, 1980, pp. 552–553, Harper & Row, New York.

D. Whittaker, Photogrammetry with Endoscope, International Archives of Photogrammetry and Remote Sensing, 1994, pp. 437–442, vol. XXX, Part. 5.

* cited by examiner

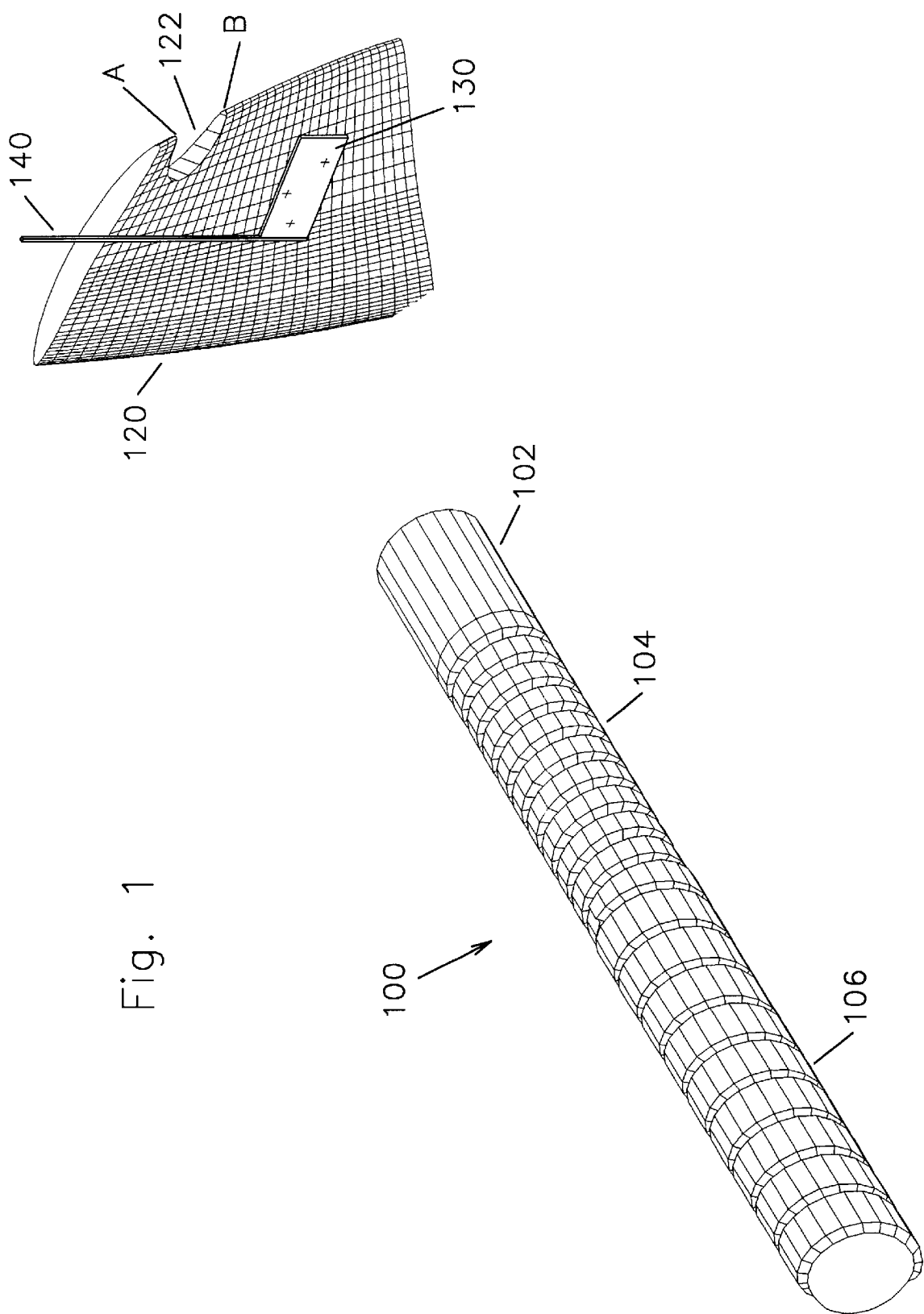

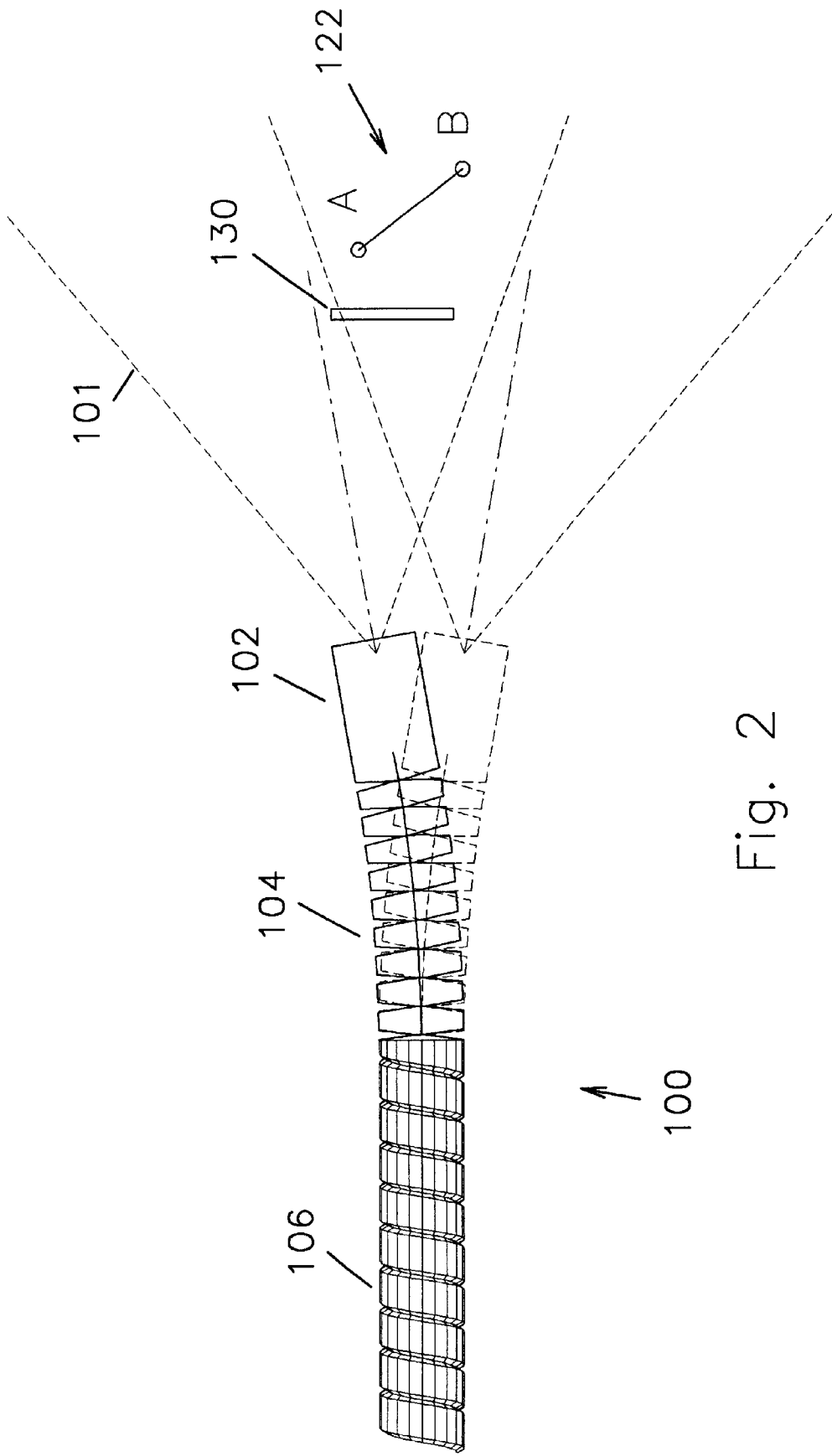

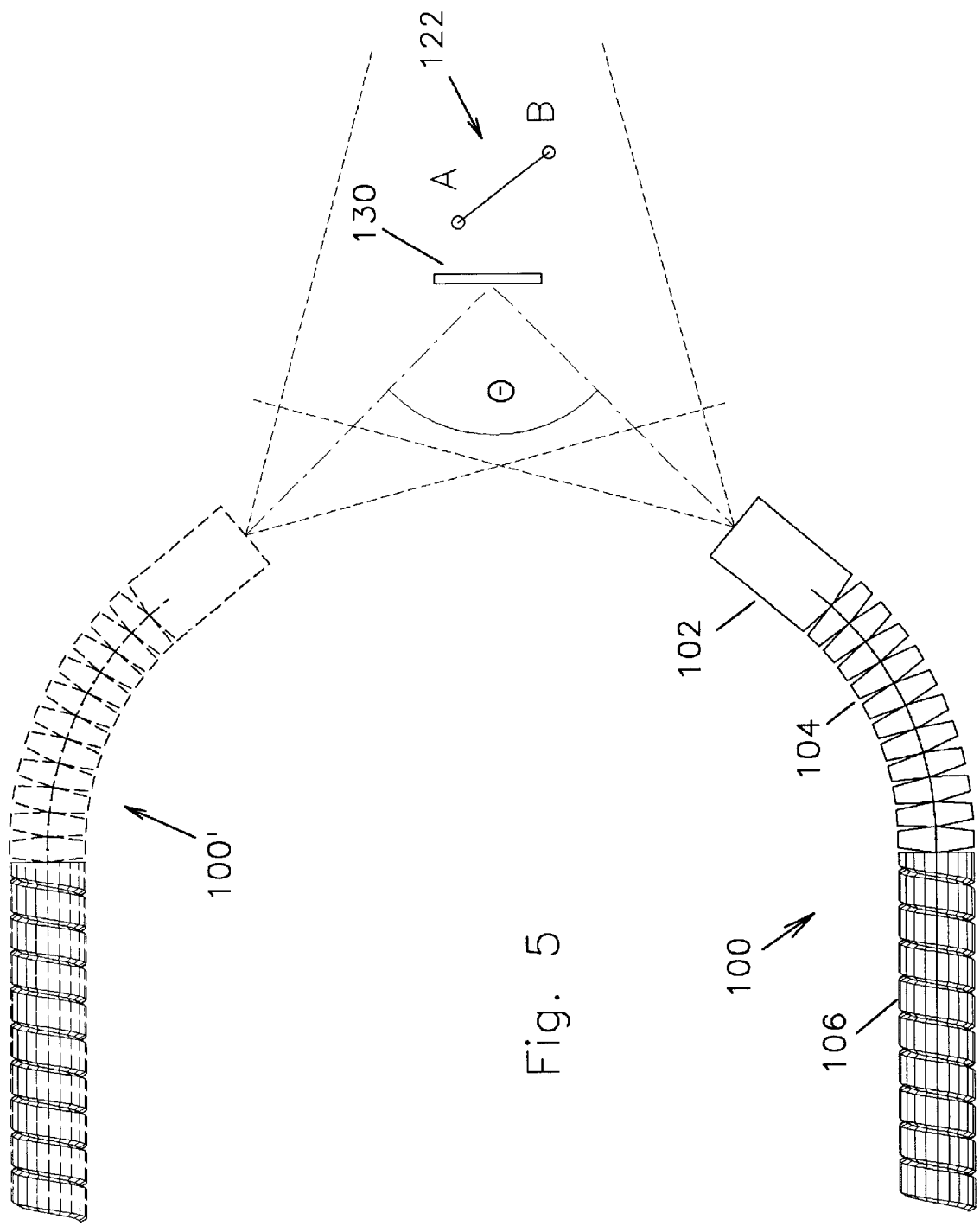

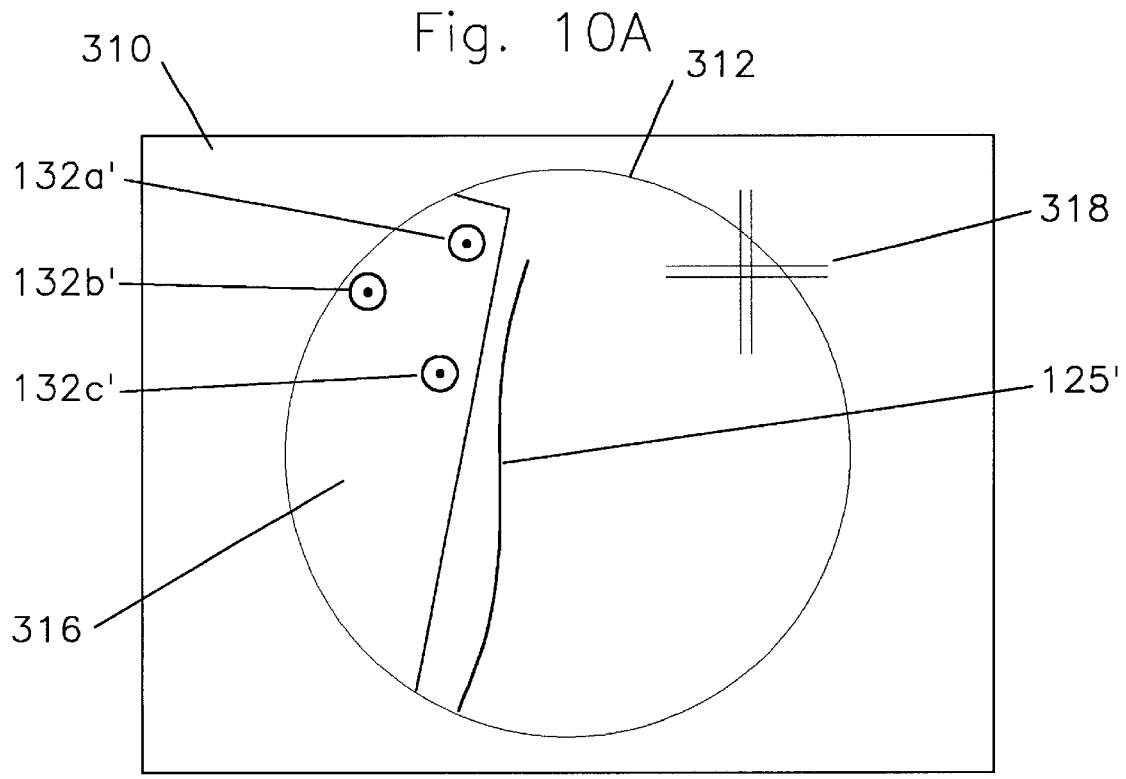
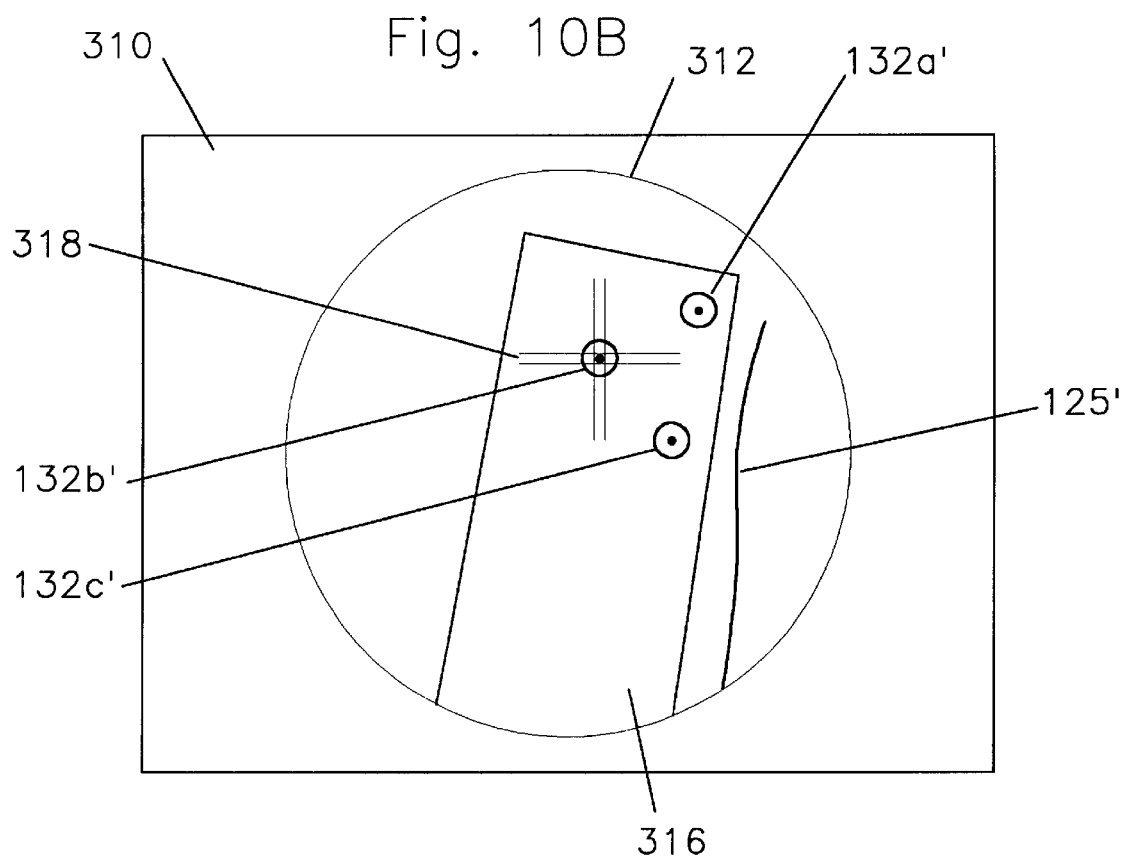

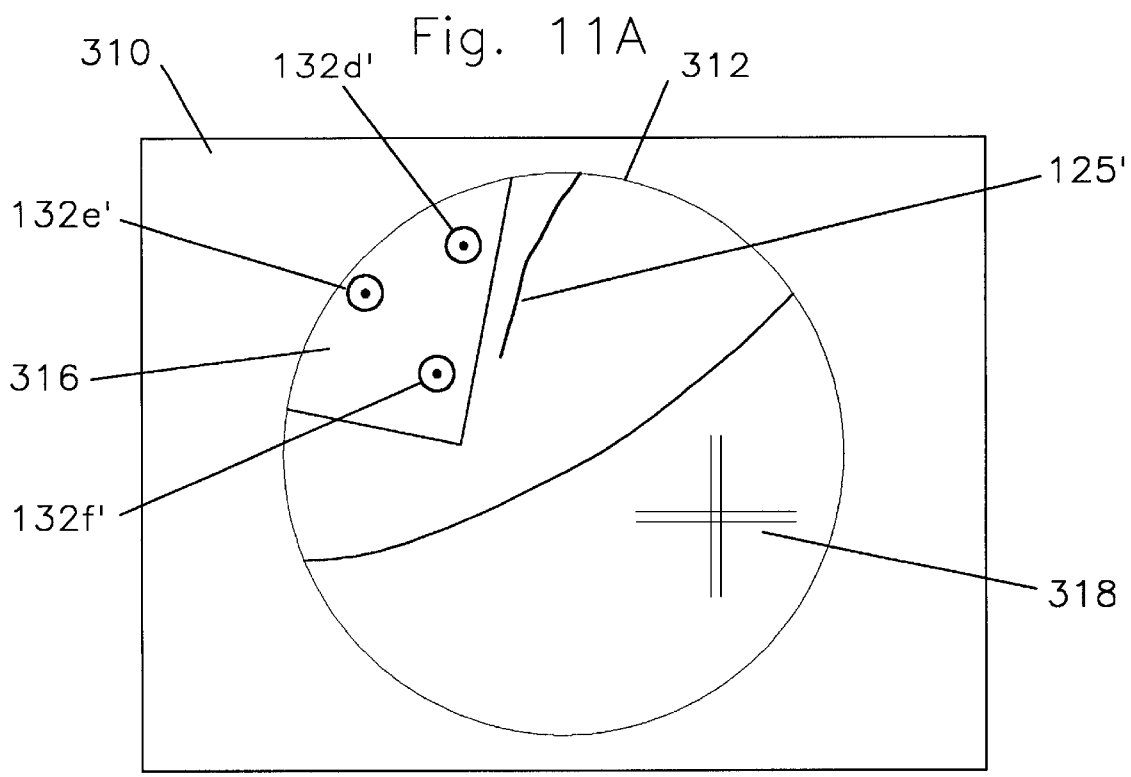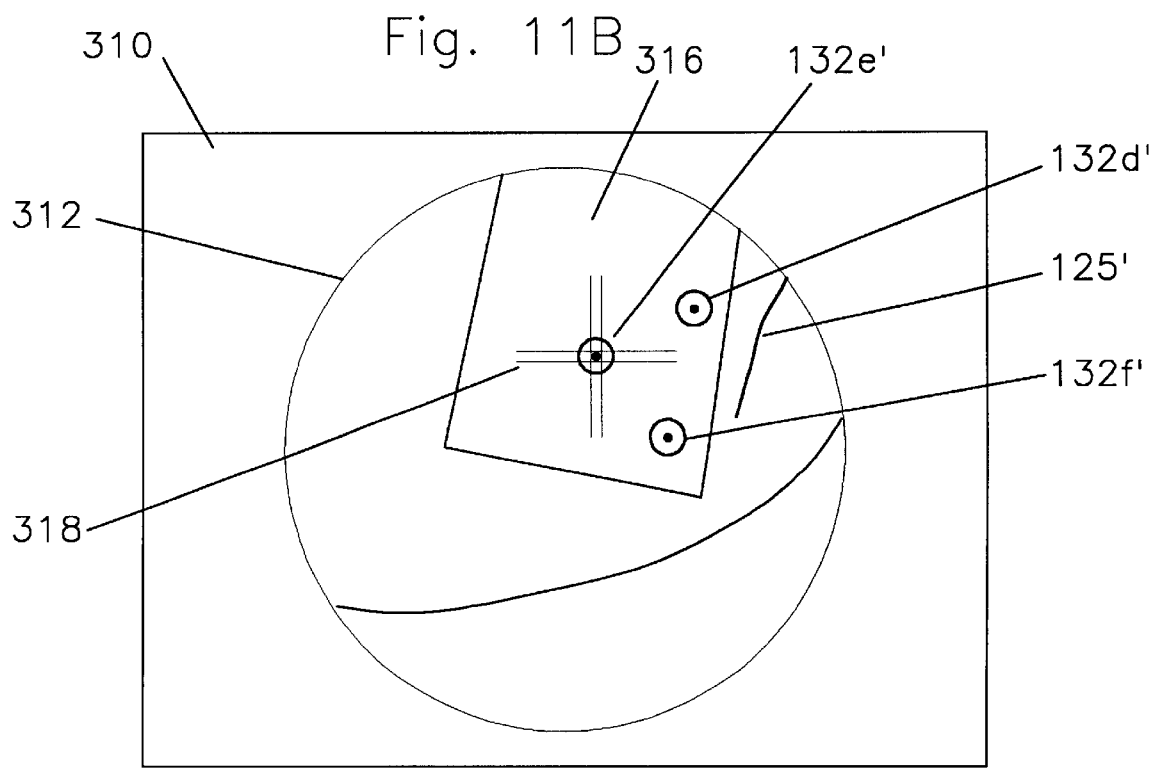

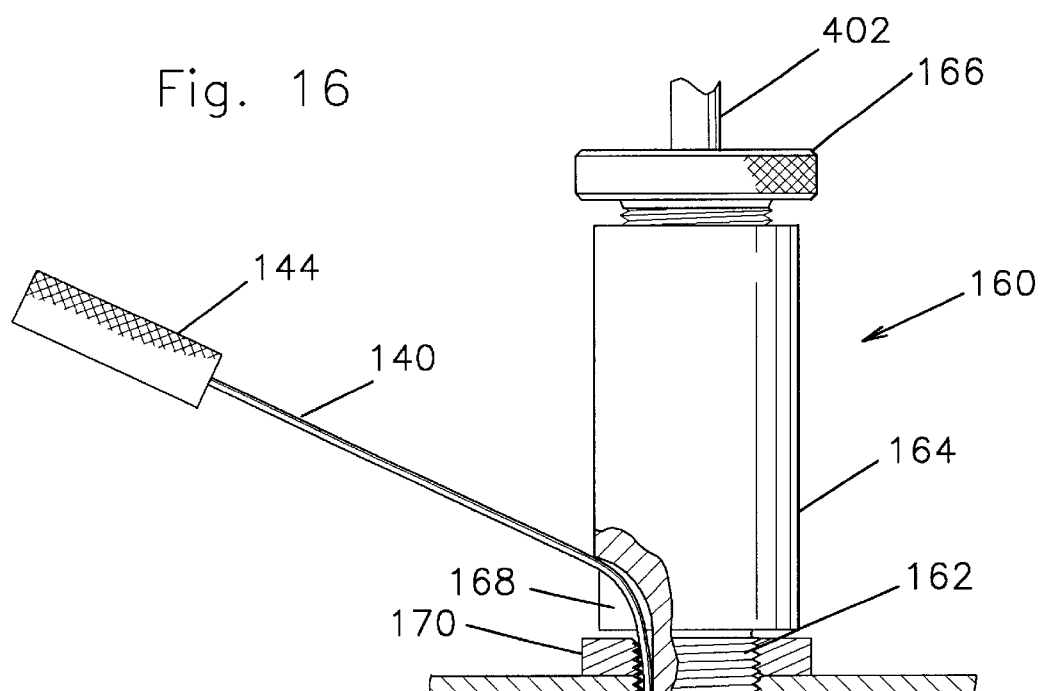
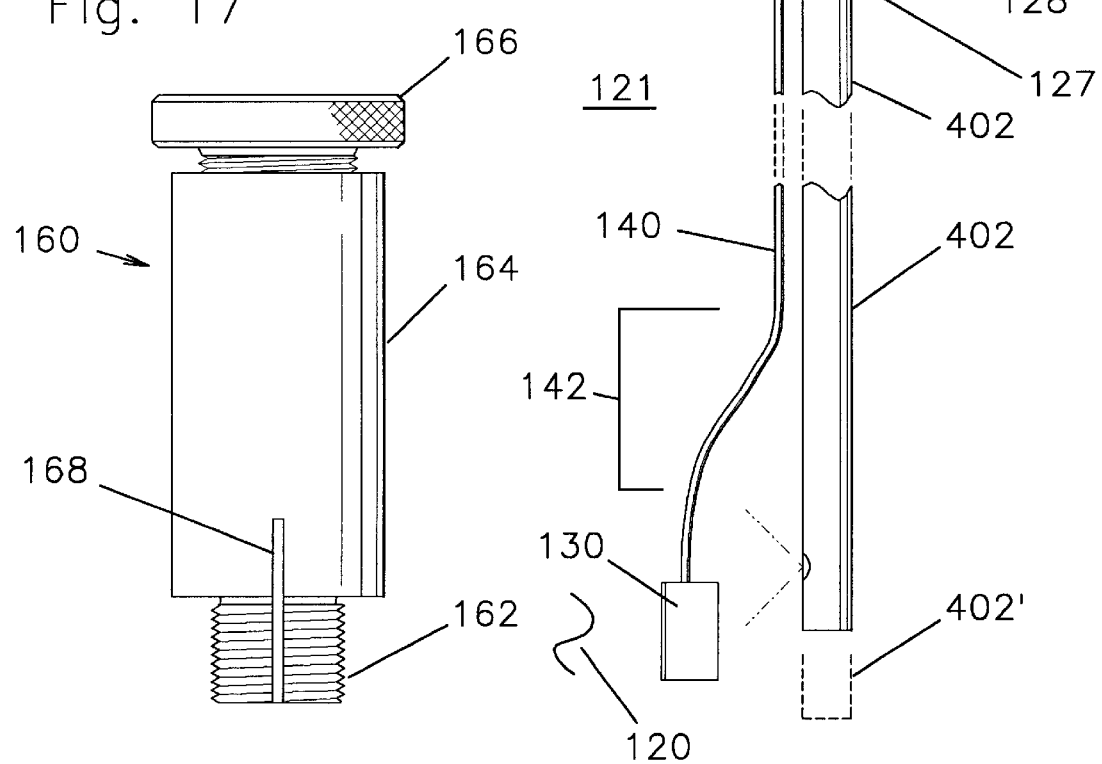

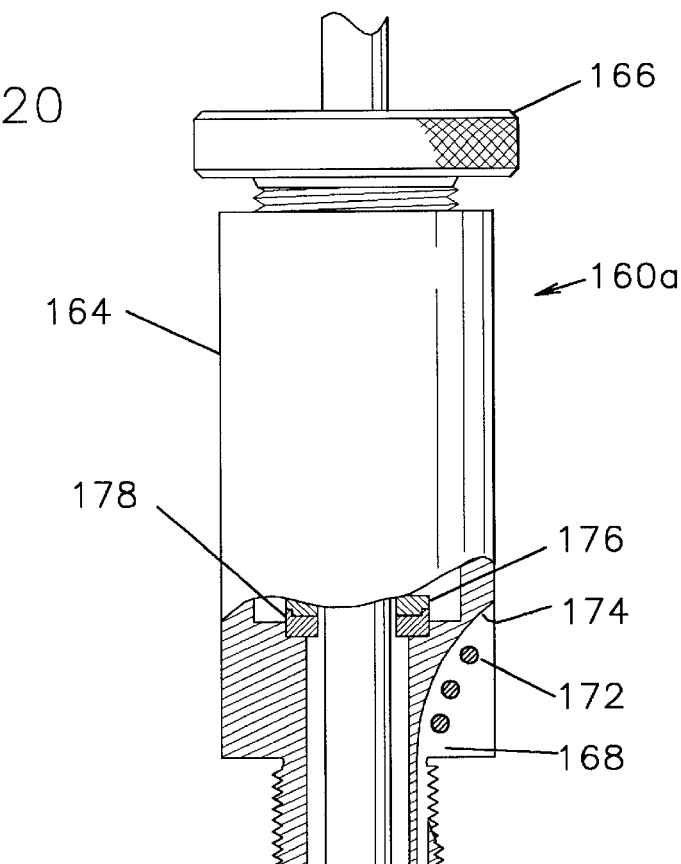
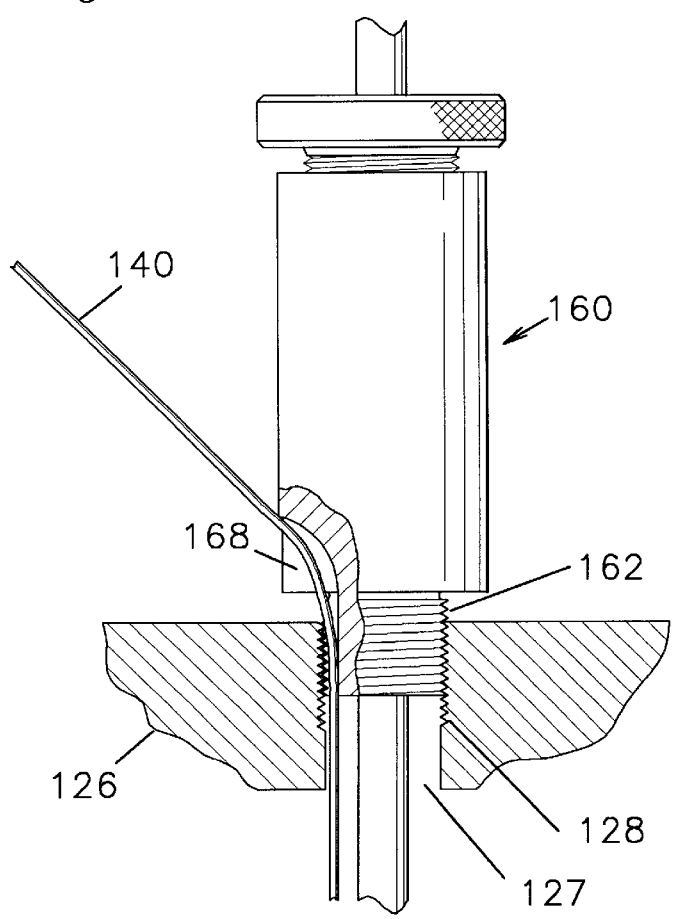

Fig. 21
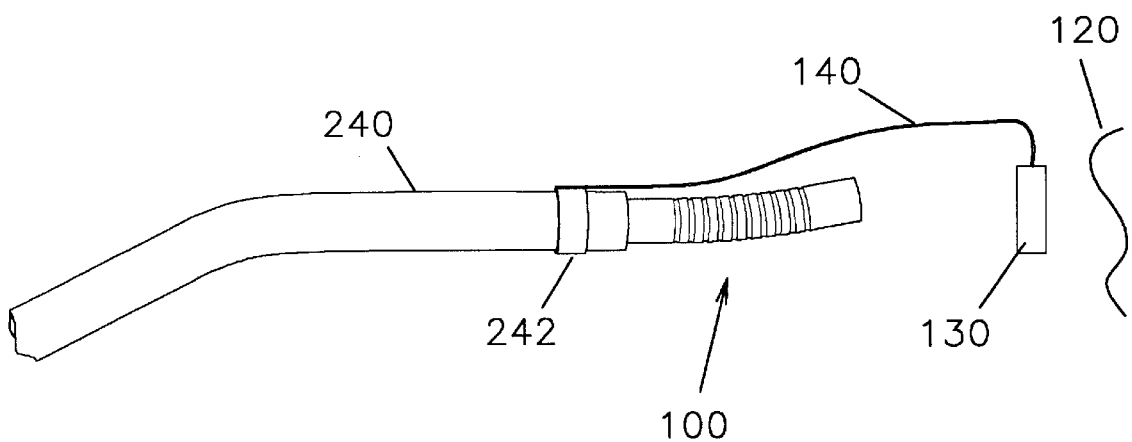
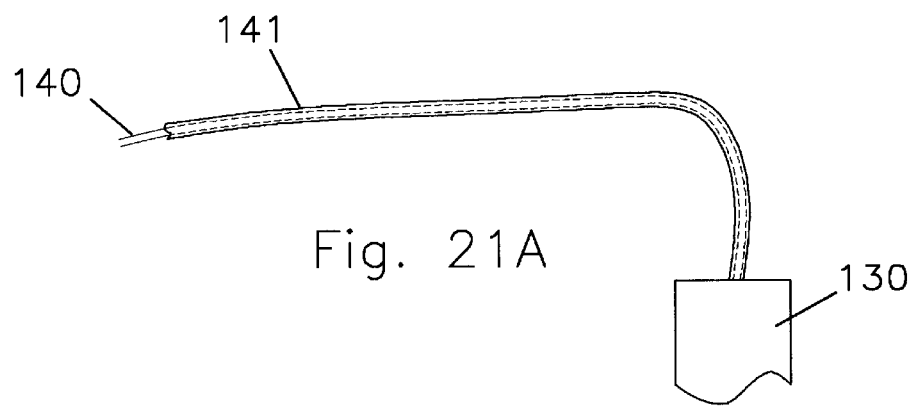
Fig. 21A
Fig. 25
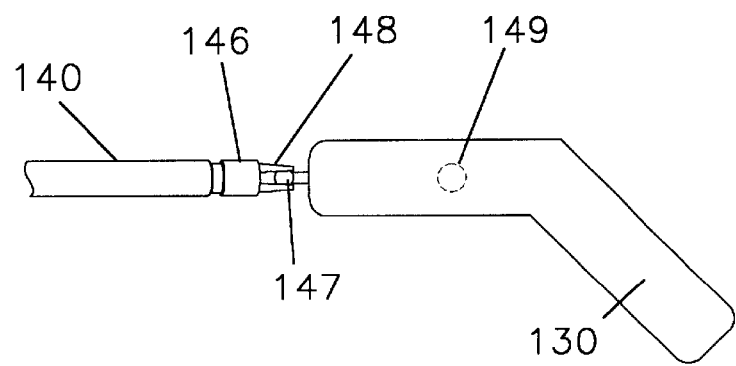

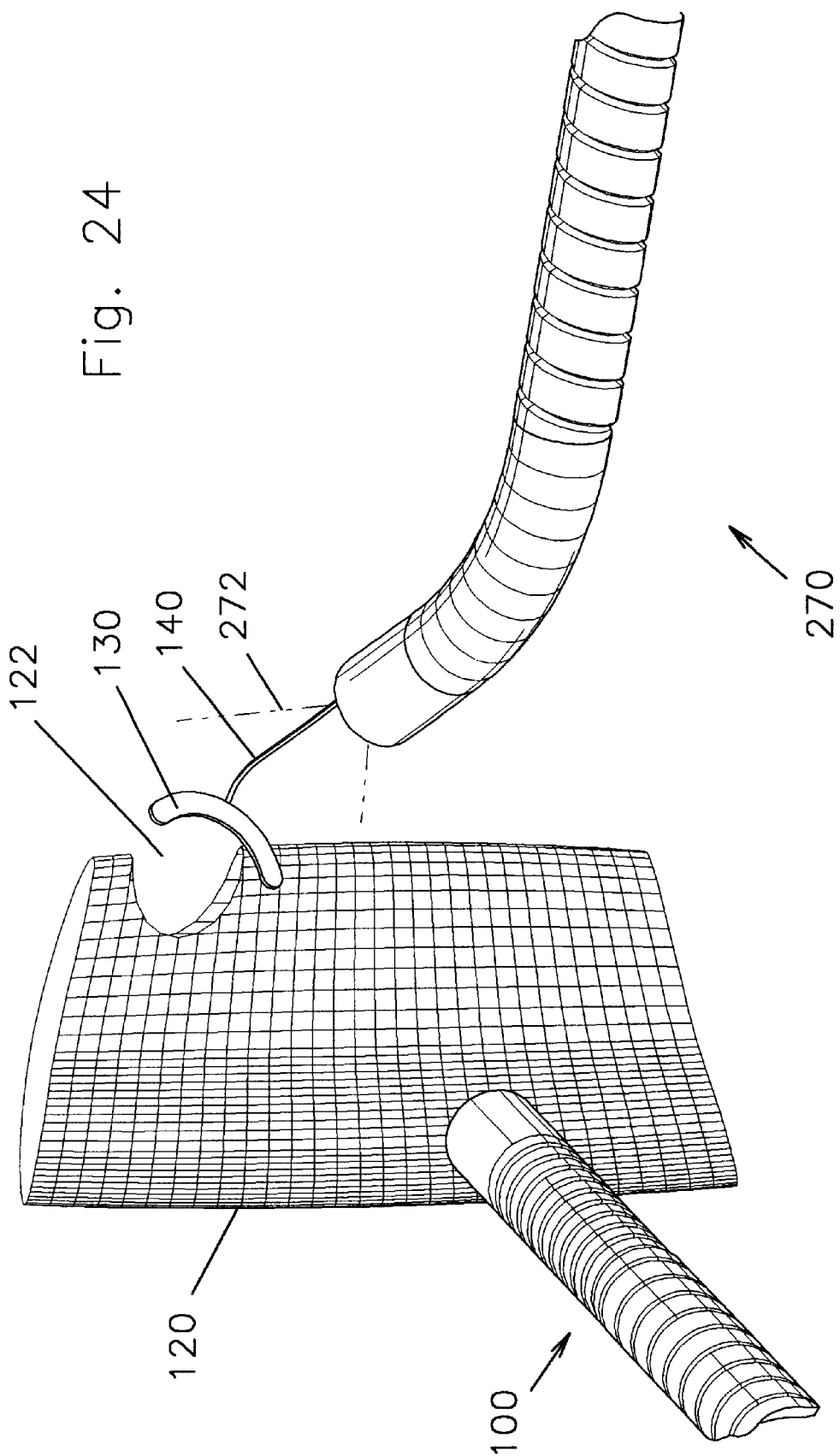

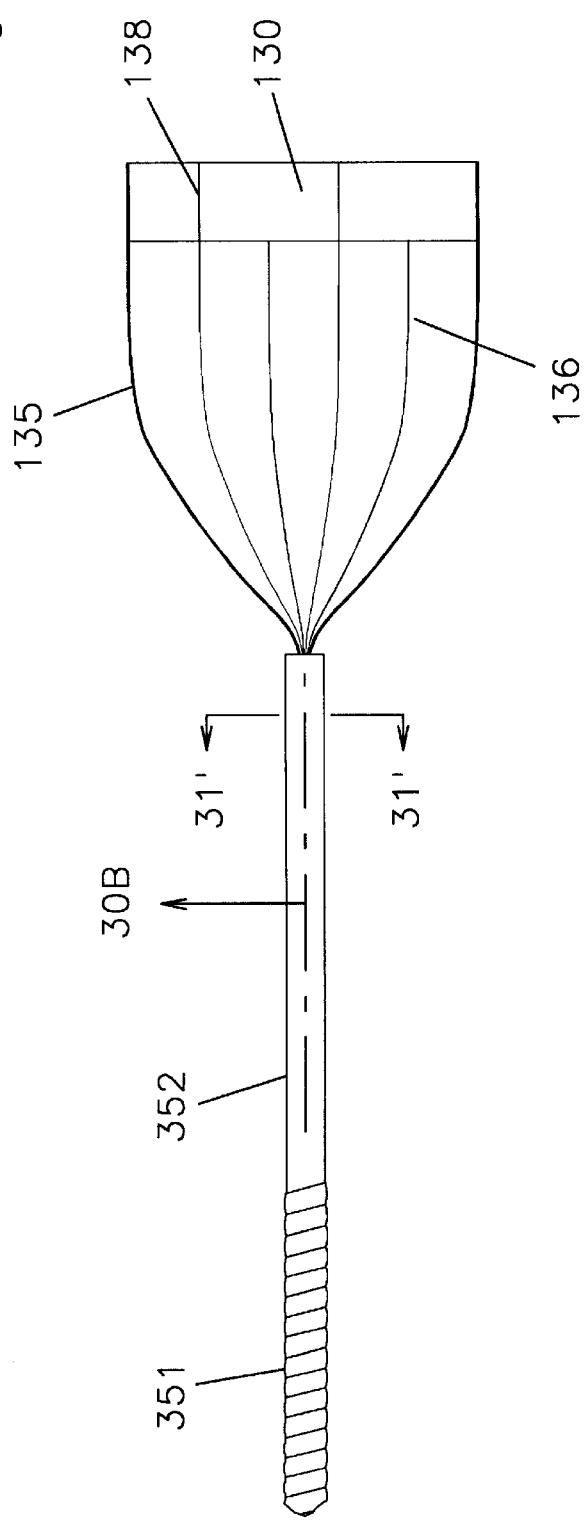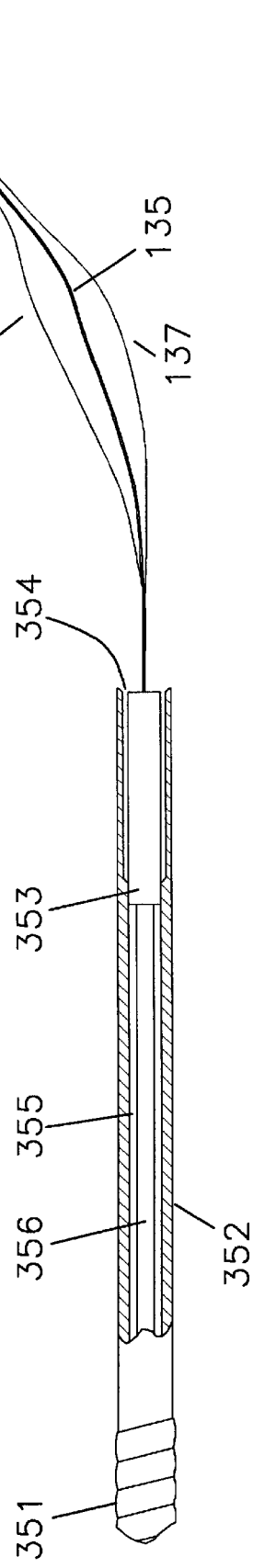
Fig. 30A
Fig. 30B

SIMPLE SYSTEM FOR ENDOSCOPIC NON-CONTACT THREE-DIMENTIONAL MEASUREMENT

CROSS REFERENCE TO RELATED APPLICATIONS

This application claims the benefit of U.S. Provisional Application No. 60/132,908 filed May 6, 1999.

STATEMENT REGARDING FEDERALLY SPONSORED RESEARCH AND DEVELOPMENT (Not Applicable)

BACKGROUND OF THE INVENTION

1. Field of the Invention

This invention relates to optical metrology, and particularly to the problem of making accurate non-contact dimensional measurements of objects that are viewed through an endoscope.

2. Description of Related Art

A. Endoscopic Measurements

Making accurate dimensional measurements of objects viewed through endoscopes is important to aerospace as well as other industries in which expensive equipment must undergo periodic internal inspections to maintain safe operation. Such measurements also have medical applications, where the internal condition of a patient is evaluated prior to or during surgery by viewing through an endoscope.

The fundamental problems in making an accurate measurement through an endoscope are that the magnification of the image varies rapidly with the range of the object, and that objects of interest (defects) lie on surfaces which are curved in three dimensions; thus the magnification varies from one point on the object to another. What is needed is a fully three-dimensional measurement, that is, one which determines the depth, as well as the height and width, of an object.

Endoscopes are long and narrow optical systems, typically circular in cross-section, which can be inserted through a small opening in an enclosure to give a view of the interior. They almost always include a source of illumination which is conducted along the interior of the scope from the outside (proximal) end to the inside (distal) end, so that the interior of the chamber can be viewed even if it contains no illumination. Endoscopes are divided into two basic types: these are the rigid "borescopes" and the flexible "fiberscopes" or "videoscopes".

Probably the simplest approach to obtaining quantitative object size information is to place a physical scale in contact with the object to be measured. U.S. Pat. No. 4,825,259 to Berry teaches this approach, as does Diener, in U.S. Pat. No. 5,803,680. Berry attaches the scale to the distal tip of an endoscope, while Diener attaches the scale to the distal end of a remote machining apparatus, where the apparatus includes an endoscope.

One problem with this approach is that it is sometimes not possible to insert the desired scale through the available access port. As an alternative, Watanabe in U.S. Pat. No. 4,721,098 teaches the construction and use of a measurement scale apparatus that has both a collapsed configuration and an expanded configuration, so that the scale can be passed through the access port when the apparatus is collapsed, and then the apparatus can be erected to an operating configuration once it is near the object of interest.

Other problems with such direct physical scale approaches are that the objects of interest are almost never flat and oriented in the correct plane so that the scale can lie against them, and that it is often not permissible to touch the objects of interest with a rigid scale. Even the seemingly simple task of bringing the scale into contact with the object so that the points of interest on the object are adjacent to the indicia of the scale is often difficult. In many cases, the precision with which the position of the scale can be manipulated is insufficient. In addition, it is difficult to determine that all of the desired indicia on the scale are in contact with the object rather than lying either in front of or behind the object.

Even when the object is suitable for measurement with a physical scale and the scale can be manipulated satisfactorily, there is an additional requirement to manipulate the end of the endoscope into the correct position to make the desired measurement accurately. Ideally, the scale is oriented perpendicular to the line of sight of the endoscope. If the scale is not so oriented, then determining when the points on the object are aligned with the indicia of the scale becomes more difficult and subject to error.

In the current marketplace, there are many existing so-called endoscopic "measurement" systems that simply make straightforward two-dimensional measurements based on applying a scale factor to the image viewed through the scope. Such systems are today almost always implemented with a video camera attached to the proximal end of the endoscope, and with a digital "frame grabber" being used to acquire and store the video images. The measurement is then made simply by counting "pixels" between features of interest in the digital video images, and a computing device multiplies this number by an appropriate scale factor, where the scale factor may or may not take into account the Seidel distortion of the optical system.

Such systems are sometimes useful, but they are severely limited by the following requirements for the two dimensional measurement to have a meaningful relationship to the true dimension of the object. First, the object being measured has to be oriented at a known angle with respect to the line of sight. Second, the distance of the object from the endoscope optical system has to be known in order to determine the correct scale factor. The angle of the object can sometimes be estimated from the known geometrical relationship of the various components of the device being inspected. The magnification of the object is sometimes estimated by incorporating an auxiliary object of known size, such as a wire, to be compared to the object of interest, or the distance is estimated by adding a physical projection to the endoscope. An example of the latter is the system of Krauter, U.S. Pat. No. 5,047,848, in which a flexible distance gauging element is attached to the distal tip of an endoscope.

Clearly there are many sources of error in such "measurements"—these are in fact crude estimates that are useful in only a limited set of circumstances. One cannot often depend on these for critical applications. Thus, much effort has gone into the development of non-contact, truly three dimensional, methods of measurement through endoscopes.

Many of the prior art approaches to three-dimensional, non-contact measurements involve adding optical projection apparatus to the distal tip of the endoscope. Besides having the problem that the measurement precision is poor, these approaches inherently involve adding apparatus to an area where space is already at a premium. The distal tip of the endoscope must be kept as small as possible in order to allow inspections in close quarters, and to allow the endoscope to be inserted through access ports which are as small as possible. Thus, ideally, one wants to be able to make the measurement without adding anything to the distal tip of an endoscope.

U.S. Pat. No. 4,895,431, "Method Of Processing Endoscopic Images", to Tsujiuchi, et. al., describes a number of methods to mathematically process two images obtained from different camera positions to derive object surface contour information. The two images are obtained by bending the end of a fiberscope. The bending is achieved using the internal articulation capability of the scope. Their technique assumes a simple linear relationship between the bend angle of the fiberscope and the offset of the nodal point of the optical system to estimate the geometrical relationship of the images. The image processing begins by correcting for distortion, then doing correlations over a series of smaller and smaller sub-images. The patent teaches that one can thereby derive full three-dimensional position data in the overlap region between the images.

One problem with this is that the bending of the end of a fiberscope is subject to a number of difficult-to-correct mechanical errors that make the feasibility of this approach questionable.

U.S. Pat. No. 5,432,543, "Endoscopic Image Processing Device for Estimating Three-Dimensional Shape of Object Based on Detection of Same Point on a Plurality of Different Images", to Hasegawa, et. al., is an improvement to U.S. Pat. No. 4,895,431, which avoids the problem of mechanical errors. The new approach is to estimate the relative positions of the imaging optical system and the object in addition to the previous estimation of the 3D contour of the object, all by using sophisticated image processing. The resulting system is purported to be able to handle even the case of a moving object.

A first problem with the approach of both Tsujiuchi et. al., and Hasegawa, et. al., is that these systems require the use of a complicated and expensive image processing device. A second problem is that they are not directed toward obtaining simple measurements of a few dimensions on the object; instead they are directed toward determining the three dimensional shape of a surface. Thus, they do not calculate or even consider the coordinates of any individual point on the object; the processes are all based on correlations over sub-images. This inherently means that for any single point of interest on an object, the estimated position of that point depends on the characteristics of neighboring points as well as on its own characteristics.

To address the deficiencies of these and other three-dimensional, non-contact endoscopic measurement techniques, I invented the system described in U.S. Pat. No. 6,009,189, which is incorporated herein by reference. Much of the same information was also published as "Apparatus and method for making accurate three-dimensional size measurements of inaccessible objects", International Pat. No. Publication Number WO 98/07001, World Intellectual Property Organization, Geneva, Feb. 19, 1998. The latter document was produced without the introduction of errors in the printing process.

In this previous system, an imaging camera is subjected to a precision motion from a first viewing position to a second viewing position, and measurements are made using the information contained in both views of the object. As explained in the referenced documents, this system is an improved version of a more general technique that I call perspective dimensional measurement.

The disclosure of U.S. Pat. No. 6,009,189 emphasizes the need for and methods of obtaining the best possible accuracy in the endoscopic measurement. Experimental results using this previous system were published in *Proceedings of SPIE*, vol. 3397, pp. 264–276, 1998. Using my teachings, it is now possible to make three-dimensional measurements to a precision of better than 1 part in 1000 of the range to the object using standard video endoscopic equipment when the object of interest has features with sharp, high-contrast edges. This is at least 10 to 20 times better than had been achievable with prior art three-dimensional endoscopic measurement systems.

While my previous system allows one to make accurate measurements with existing rigid borescopes, if that system is to be used with a flexible endoscope, it requires that a completely new flexible scope be designed and manufactured. In addition, the high level of measurement accuracy offered by that system is not always required, although one does usually want a better measurement than was provided by earlier systems.

B. Photogrammetric Measurements

In recent decades new applications of photogrammetry (i.e., the science and technology of making measurements from photographs) have been introduced under the names "non-topographic photogrammetry" or "close-range photogrammetry". In the typical application of this art, a large structure such as a dam, a building, a ship, or an archeological site is accurately measured using a number of photographs taken from different viewing positions. Often, more than two viewing positions are used. Such measurements are miniature engineering projects, requiring extensive planning before the data are acquired and extensive data analysis after the data are acquired. The equipment required is complex and expensive, however the measurement accuracies obtainable are extremely high, with 1 part in 10,000 of the range being considered minimal accuracy and in excess of 1 part in 200,000 being achievable. A classic reference to this field is the book *Handbook of Non-Topographic Photogrammetry*, H. M. Karara, ed., American Society of Photogrammetry, 1979.

In one type of non-topographic photogrammetry a large number of alignment targets are attached to the object to be measured. The positions of these targets, when determined by the photogrammetric process, are used to represent the object. That is, in these measurements the points on the object to be measured must be preselected during the planning stage.

In another type of photogrammetric measurement, a so-called control frame is placed around the object of interest and the object and the control frame are photographed together. If the three-dimensional positions of a sufficient number of control points on the control frame have been independently determined, then desired points on the object can be measured. In this case, the points to be measured on the object need not be preselected. This avoids the extensive preplanning but it still requires the extensive (and expensive) post analysis of the photographs.

In still other applications of photogrammetry, the object of interest is considered to have a number of well defined points for which the three-dimensional positions are already known. These specific object points are then used as control for photogrammetric measurements of other portions of the object. Such a system for making measurements inside a gas turbine engine is proposed in an article by D. Whittaker, "Photogrammetry with Endoscope", *International Archives of Photogrammetry and Remote Sensing*, vol. XXX, Part 5, pp. 437–442; 1994. As described by Whittaker, setting up to make the proposed measurements inside the engine is a major engineering project; and after the scheme is set up, extensive data reduction would be necessary for any individual measurement to be made.

The problem with the application of photogrammetry to the endoscopic measurement application is the difference between the goals of photogrammetry and the goals of endoscopic measurement. In photogrammetry, the goal is usually to characterize the structure as a whole; thus a very large amount of data is desired. In endoscopic measurements we are concerned with discrete positions on the object of interest, typically sites of damage such as nicks, cracks, or pits in industrial applications, or the size of tumors or other features of the body in medical applications. Often a single dimension between two points on the object is the only information desired. Rather than needing the extremely high accuracy of which photogrammetry is capable, the precision of an endoscopic measurement needs to be between 1 part in several hundred and 1 part in 10,000 of the range. Rather than being an engineering project that takes hours, days or weeks, the endoscopic measurement must be performed in minutes. Rather than allowing for the use of expensive photoreduction hardware and software, the endoscopic measurement must be as inexpensive as possible. For these reasons, to my knowledge, photogrammetry per se has not found application in endoscopic measurements.

In fact, the differences between the practice of photogrammetry and the needs of endoscopic measurement are so profound that its practitioners have not considered photogrammetry to be applicable to endoscopic measurement at all. For instance, in the book *Close-Range Photogrammetry & Surveying. State of the Art*, American Society of Photogrammetry; 1985, in an article on applications in medicine, a major academic figure in photogrammetry, professor F. H. Moffit of the University of California at Berkeley, made the statement: "Various types of endoscopes such as the colonoscope and the sigmoidoscope can be used to photograph internal parts for later examination and interpretation; however, this is outside the purview of the photogrammetrist." (p. 761). A similar sentiment was recently stated by I. Newton and H. L. Mitchell in the Chapter entitled "Medical Photogrammetry" in the book *Close Range Photogrammetry and Machine Vision,* K. B. Atkinson, ed., Whittles Publishing, Bristol, England, 1996. They state: "Although photogrammetry, along with other optical techniques, appears to have the disadvantage that it is associated with the exterior of the body, rather than the interior which is often seen as so relevant to health, it is found in practice that external studies are valuable in many situations for a number of reasons." (p. 304).

C. Summary of Prior Art

To summarize the deficiencies of the prior art in endoscopic measurements, methods requiring physical contact for dimensional measurements are not often applicable in practice. Many available endoscopic non-contact measurement systems are not truly three-dimensional, and therefore are inaccurate. Optical projection approaches involve increasing the size of the distal tip of the endoscope, they require that a specialized measurement endoscope be acquired at high cost, and their accuracy is insufficient. Image processing approaches are complicated and expensive, are not directed toward obtaining measurements of the distances between a few specific points on an object, and their accuracies are currently unknown. My previous perspective dimensional measurement system provides three-dimensional measurements of nigh accuracy, but it cannot be used with standard, unmodified flexible endoscopes. The practice of close-range photogrammetry has been directed toward making measurements of extremely high accuracy where the time necessary to make the measurement, and the cost of the equipment required are completely out of the question for the endoscopic measurement application.

What is needed is an inexpensive system that can be used with existing flexible endoscopes that provides a non-contact, true three-dimensional measurement. The system should not involve adding any apparatus to the distal tip of an endoscope, even as an add-on accessory. In addition, it would be ideal if this new system could be easily retrofitted to existing two-dimensional pixel counting endoscopic "measurement" systems to upgrade their accuracy and usefulness.

BRIEF SUMMARY OF THE INVENTION

The present invention resolves the problems identified with the prior art and offers additional advantages as well. It is a first object of this invention to provide a non-contact method for making true three-dimensional measurements of the distances between individual points on an object that can be used with any endoscope, without requiring any modification of the endoscope.

A second object of this invention is to provide a non-contact method for making three-dimensional measurements which does not require the use of an image processing device.

A third object is to provide a non-contact method and apparatus for measuring three-dimensional distances which are not fully contained in any single view of a measurement camera.

A fourth object is to provide a method for making non-contact three-dimensional measurements which does not require any pre-calibration of the measurement endoscope.

A fifth object is to provide a variety of apparatus for implementing the methods that enable accurate three-dimensional measurements to be made using any endoscope.

A sixth object is to provide a variety of measurement apparatus that enable three-dimensional measurements to be made in a wide variety of applications where the object to be measured is inaccessible except through access openings in an enclosure.

A seventh object is to provide a variety of measurement apparatus which can be inserted through existing inspection ports in equipment to be inspected.

An eighth object is to provide a method for determining three-dimensional coordinates for at least one point on an object in which the method does not require that an endoscope be subjected to an accurately predetermined motion.

The methods of the instant invention are adaptations of my improved perspective dimensional measurement technology in which the motion of the camera, rather than being precisely controlled, is instead determined by using additional information contained within images obtained at the two viewing positions. This additional information is added to the scene being viewed by placing an array of reference target points into the scene next to, and fixed with respect to, the object of interest.

Rather than simply measuring the positions of the images of object points of interest in each of the two views, in the new methods one also measures the positions of the images of a number of the reference target points. These additional data, together with predetermined spatial relationships between the reference target points and together with internal calibration parameters of the camera, enable one to determine the positions and orientations of the measurement camera in three-dimensional space for each of the views. Optionally, one may either predetermine the internal calibration parameters of the camera, or determine those parameters simultaneously with the determination of the positions and orientations of the camera. The latter option requires one to measure the positions of a larger number of reference target points than does the former.

Once the locations and orientations of the measurement camera have been determined for each of the views, one can determine three-dimensional distances between the points of interest on the object using the improved perspective dimensional measurement technique taught in my previous application, now U.S. Pat. No. 6,009,189. Measurements can be made with the new methods with either the "mode 1" or "mode 2" processes taught there. In mode 1, all the distances to be determined must be fully contained in each camera view. In mode 2, a distance can be determined which is too large to be contained within any single camera view.

A general measurement reference apparatus comprises a reference target array which is placed near to and fixed with respect to an object of interest inside an enclosure by means of a reference array holding apparatus and a reference array insertion apparatus. This measurement reference apparatus can be used to make either perspective dimensional measurements as I teach or to make conventional photogrammetric measurements.

A general measurement apparatus to be used with the new methods comprises a reference target array which is placed near to and fixed with respect to an object of interest inside an enclosure by means of a reference array holding apparatus and a reference array insertion apparatus. This apparatus allows for the possibility of using the reference array holding apparatus to attach the reference array directly to the object of interest. In this case, the reference array and the array holding apparatus are inserted into the enclosure by the insertion apparatus. The general measurement apparatus also comprises an endoscopic camera located inside the enclosure. The camera is moved with respect to the object by a camera moving apparatus. Images formed by the camera are measured with an image measurement apparatus. These measurements are supplied to a computing apparatus which computes the desired three-dimensional distances. The measurement results are displayed to the user by a display apparatus.

In a first specific embodiment of a measurement apparatus, the camera is a flexible endoscope, and the camera moving apparatus can either be the internal articulation provided within the endoscope or the endoscope can be subjected to any other motion which meets a specific requirement that is explicitly taught.

In a second specific embodiment, the camera is a substantially side-looking rigid borescope, and the camera is moved by translating the borescope in a direction substantially along its length. A first borescope holder is taught that provides the user with a convenient way to hold the borescope steady at each viewing position in this embodiment.

In a third specific embodiment, the camera is a rigid borescope (either forward-looking or side-looking), and the camera is moved by rotating the borescope about an axis of rotation that is substantially perpendicular to the length of the borescope and that is nearly coincident with the inspection port through which the borescope has been introduced to the interior of the enclosure. A second borescope holder is taught that provides the user with a convenient way to hold the borescope steady at each viewing position in this embodiment.

Any of these specific embodiments of measurement apparatus can be used with any of a number of specific implementations of reference target arrays and reference target array insertion and holding apparatuses. The array of reference targets can be introduced into an enclosure, brought to a position near the object of interest, and held at a fixed position with respect to the object using a variety of modifications of standard endoscopic inspection accessories. In specific implementations, the array of reference targets is supported by a rigid, a semi-rigid, or a flexible endoscope guide tube. Optionally, the array may be supported by a wire which is fed through a lumen in the wall of the guide tube. In another implementation, the array of reference targets is supported by a second endoscope. In additional implementations, the reference target array is supported by a support wire which is mounted to the enclosure at an inspection port.

Arrays of reference targets may be marked on rigid or flexible substrates. In certain preferred implementations, the substrate of the array is planar, while in others, the array is three-dimensional. For planar arrays, a feature is added to the array that makes it easy for the user to determine an additional piece of information that is necessary if one wants to minimize the number of reference points used in the measurement. A number of specific three-dimensional arrays are taught that have the advantage that they can be characterized using only one- and two-dimensional metrology.

Optionally, the substrate of the array may contain one or more apertures thus enabling one to view the object through the array. In another implementation, the array is marked on a loop of wire. In additional implementations, the array may have a variable orientation with respect to its support member. In a specific implementation, an insertion tool is provided that enables a flexible reference target array to be collapsed for insertion through an inspection port and then expanded once it is inside an enclosure. Other specific implementations provide a combined reference array, support means, and insertion means, where the flexible reference target array is mounted at the distal end of the support means, and where the array can be collapsed to a small size for insertion, and expanded to full size for measurement.

Further objects, advantages, and features of my system will become apparent from a consideration of the drawing and ensuing description.

BRIEF DESCRIPTION OF THE DRAWING

FIG. 1 shows a first embodiment of a measurement apparatus according to the present invention being used to measure the distance between two points, A and B, on a remote object.

FIG. 2 depicts schematically the measurement principle of the present invention.

FIG. 5 depicts a measurement being made with a flexible endoscope undergoing both a large translation and a rotation between two viewing positions.

FIG. 10 shows two views of a video monitor as seen by the user during a first stage of the second distance measurement procedure.

FIG. 11 shows two views of a video monitor as seen by the user during a second stage of the second measurement procedure.

FIG. 16 is a fragmentary side elevation view, partially cut away, of a second embodiment of a measurement apparatus according to the present invention.

FIG. 17 is a front elevation view of the exemplary borescope support body used in the second embodiment.

FIG. 18 is a fragmentary side elevation view, partially cut away, of an alternate implementation of the second embodiment.

FIG. 20 is a side elevation view, partially cut away in cross-section, of the exemplary borescope support body used in the third embodiment.

FIG. 21 depicts a measurement apparatus using a rigid or semi-rigid guide tube with an attached reference target array supported by a wire. FIG. 21A is a detail of a variant in which a dissipative coating is used on the support wire to reduce the effect of vibrations.

FIG. 24 shows the use of a second endoscope to manipulate and hold a reference target array.

FIG. 25 shows a rigid target array which can take various orientations with respect to its support.

FIG. 30 shows top and side views of the expanded configuration of the flexible reference target array of FIG. 29. FIG. 30A is a top view, while FIG. 30B is a side view, partially in cross-section, generally as indicated by the arrow marked 30B in FIG. 30A.

FIG. 36 depicts two views of a three-dimensional target array based on an inflatable bladder. FIG. 36A is drawn partially in cross-section, and shows the bladder inflated, while

DETAILED DESCRIPTION OF THE INVENTION

1. Description of a First Embodiment

Figure 3A:
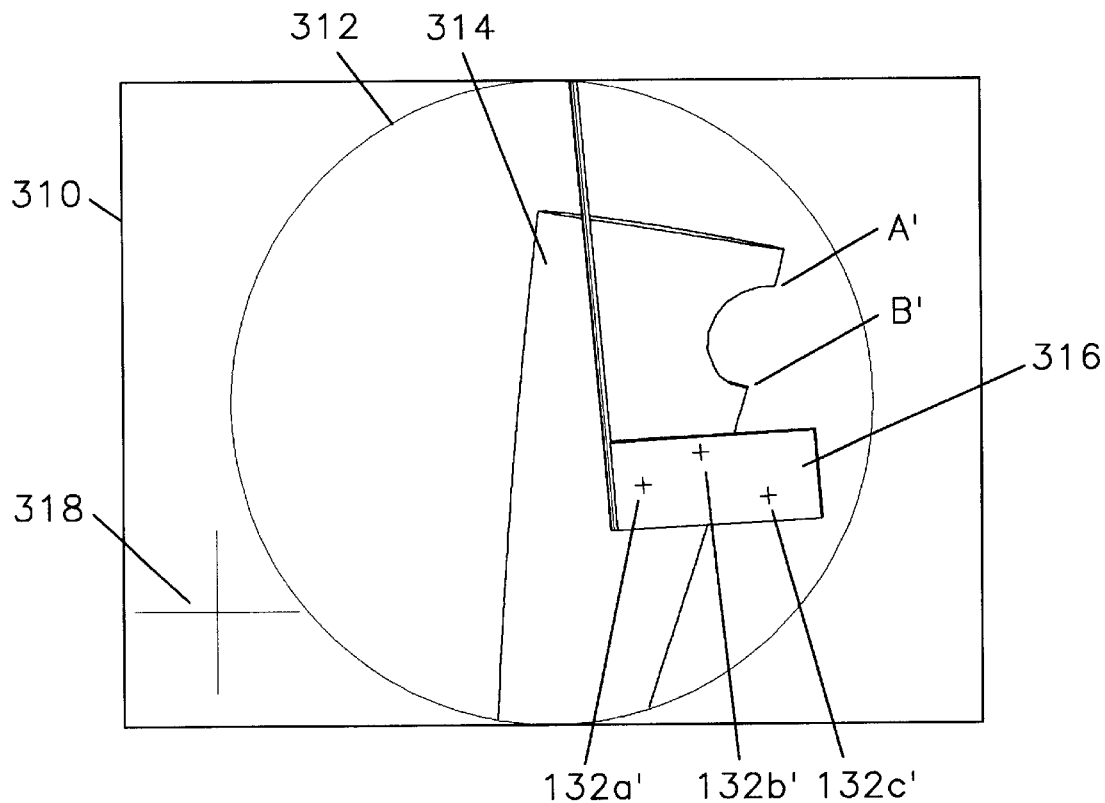
FIG. 3 depicts two views of a video monitor as seen by the user during the two steps of a first measurement procedure.

FIG. 1 depicts a flexible endoscope 100 being used to inspect an object 120. Only the most distal portion of endoscope 100 is shown; it is to be understood that the invention is most advantageous when object 120 is located at some inaccessible position inside an enclosure. It is also to be understood that, under typical conditions, flexible endoscope 100 will have been manipulated through one or more available access ports in the structure of the enclosure to achieve the position with respect to object 120 shown in FIG. 1.

The distal portion of endoscope 100 is made up of an imaging section, 102, a bending or steering section 104, and a flexible insert section 106. Insert section 106 extends back to the user interface (not shown) at the proximal end of the endoscope (not shown).

Object 120 has damage or some other feature of interest 122. The problem is, for example, to measure the distance between points A and B of feature 122. In general, this measurement must be a three-dimensional measurement, because points A and B are at different distances from the optical system of imaging section 102 of endoscope 100.

As a preliminary step in performing the measurement according to this new system, FIG. 1 also shows that a measurement reference target array 130, located at the distal end of a support wire 140, has also been inserted into the enclosure through one or more access ports, and has been manipulated to a position near object 120.

In general, the access ports through which reference target array 130 has been inserted into the enclosure may be either the same as or distinct from the access ports through which endoscope 100 has been inserted. This issue is discussed at greater length below.

Once target array 130 is in position near object 120, the proximal end of wire 140 is clamped or otherwise secured to the enclosure or to some other object which is fixed in position with respect to object 120 to fix the location of array 130 with respect to object 120.

Usually, the proximal end of scope 100 will also be secured to a portion of the enclosure fixed with respect to object 120, so that a steady image can be viewed through the endoscope. However, if a digital video system with a frame grabber is used to capture video images at the proximal end of endoscope 100, then the requirements for securing the location of the proximal end of the scope can be relaxed to a large extent. In this latter case, it is often possible to hand hold the proximal end of flexible endoscope 100 during the measurement.

FIG. 2 depicts the basic principle of measuring the three-dimensional distance between points A and B according to the new system. During the measurement operation, the imaging section 102 of endoscope 100 is moved to obtain two different views of the area of interest 122. For instance, using the facility provided within endoscope 100 for viewing objects at different orientations with respect to itself, steering section 104 at the proximal end of endoscope 100 is bent by the user to obtain in succession two suitable views. The key to the new measurement method is that not only is object area of interest 122 contained within both views, but so is at least a portion of reference target array 130.

Figure 3B:
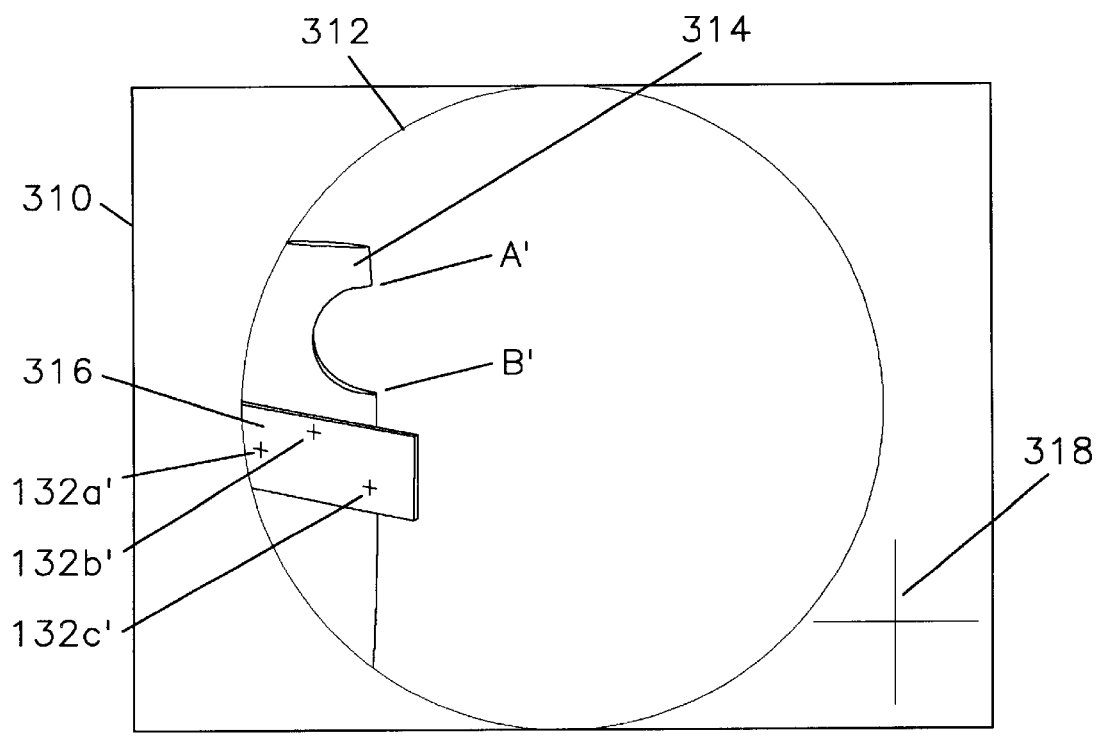

FIGS. 3A and 3B show two typical views as seen by the user during the two steps of a first measurement procedure. On a video screen 310 there is seen an image of the borescope field of view, which I call the apparent field of view, 312.

Inside apparent field of view 312 is shown an image of the object being inspected, 314. Also within the apparent field of view is seen an image of the reference target array, 316. There are also seen images 132a', 132b', and 132c' of three particular reference target points with corresponding unprimed designations (shown, but not identified, in FIG. 1). Also shown are images A' and B' of two object points of interest. Superimposed on video screen 310, and hence on images 314 and 316, is a cross-hair, fiducial mark, or cursor, 318, that can be positioned to any point on video screen 310 under user control.

It is to be understood that the designations of the reference target points are to be unambiguously defined, such as by specific marks made on reference target array 130, so that the user can identify which reference target point is which without confusion, even though such marks are not shown in FIG. 1 nor are they shown in most of the subsequent Figures.

Incidentally, there is no requirement that apparent field of view 312 be completely contained within video screen 310 as depicted in FIG. 3. The relative configuration of apparent field of view 312 and video screen 310 shown here should be taken only as a typical example. For instance, apparent field of view 312 is circular as shown, but this is not inherent to or required for the measurement.

As shown in FIG. 2, the bending of steering section 104 causes imaging section 102 of endoscope 100 to both translate and rotate in three dimensional space with respect to both object 120 and target array 130. Thus, both the image of the object, 314, and the image of the reference target array, 316, appear to move with respect to apparent field of view 312 as steering section 104 is bent, creating two different views as shown in FIG. 3.

As was fully disclosed in U.S. Pat. No. 6,009,189, when two views of an object are obtained with a camera from different positions in three dimensional space, it is possible to determine the true three-dimensional distances between points on the object, provided that the relative positions and orientations of the camera at the two viewing positions are known. In the new system of the present invention, the motion of the camera from the first viewing position to the second viewing position is not known prior to the measurement, because the motion of the flexible tip of endoscope 100 is not under precise control. However, the relative positions and orientations of the camera at the first and second viewing positions can be determined from the images obtained at these viewing positions because of the presence of reference target array 130.

Initially, in a separate calibration setup, internal calibration parameters of endoscope 100 can be determined. This is what I call an optical calibration, and it need only be performed once provided that no internal changes are made to the optical system of the endoscope after the calibration.

During the measurement, the two dimensional apparent positions of the reference target points, 132a, 132b, etc., on video screen 310 are determined along with the two dimensional apparent positions of the desired points on the object, A and B. This process is performed at both the first and second viewing positions, i.e., on both images as shown in FIG. 3.

If the two images are captured with a digital video system, then it is possible to display them both simultaneously, side by side, on video screen 310.

Combining the optical calibration data with the apparent positions of the reference target points enables one to locate and orient the camera in three dimensions with respect to the coordinate system defined by the reference target points on array 130. As a result, the camera is located in three dimensions in each image of the pair of images. Since reference target array 130 is fixed with respect to object 120, points A and B can also then be located in a three-dimensional coordinate system that is fixed with respect to target array 130. Once both points A and B are located in the same three-dimensional coordinate system, the distance between the points is easy to calculate, using the Pythagorean theorem.

Unlike those measurement methods which rely on physical scales, the reference target points 132a, 132b, etc., need not touch points A and B, nor do they have to be aligned with these points in any manner. The reference target points may lie either closer to or farther from the endoscope than do points on the object. Thus, there is no need to perform a difficult alignment of a scale with points A and B. In addition, there need be no particular orientation of endoscope 100 with respect to object 120 or target array 130, something that is also required to obtain accurate measurement results with physical scale approaches.

The principles for obtaining the best precision in perspective dimensional measurements were taught in U.S. Pat. No. 6,009,189, and these principles apply to the instant invention as well. The most important principles are that the angle subtended by the two camera viewing positions at any point of interest on the object must be substantially different from zero, and that there is an optimum range for the value of this subtended angle.

Figure 4:
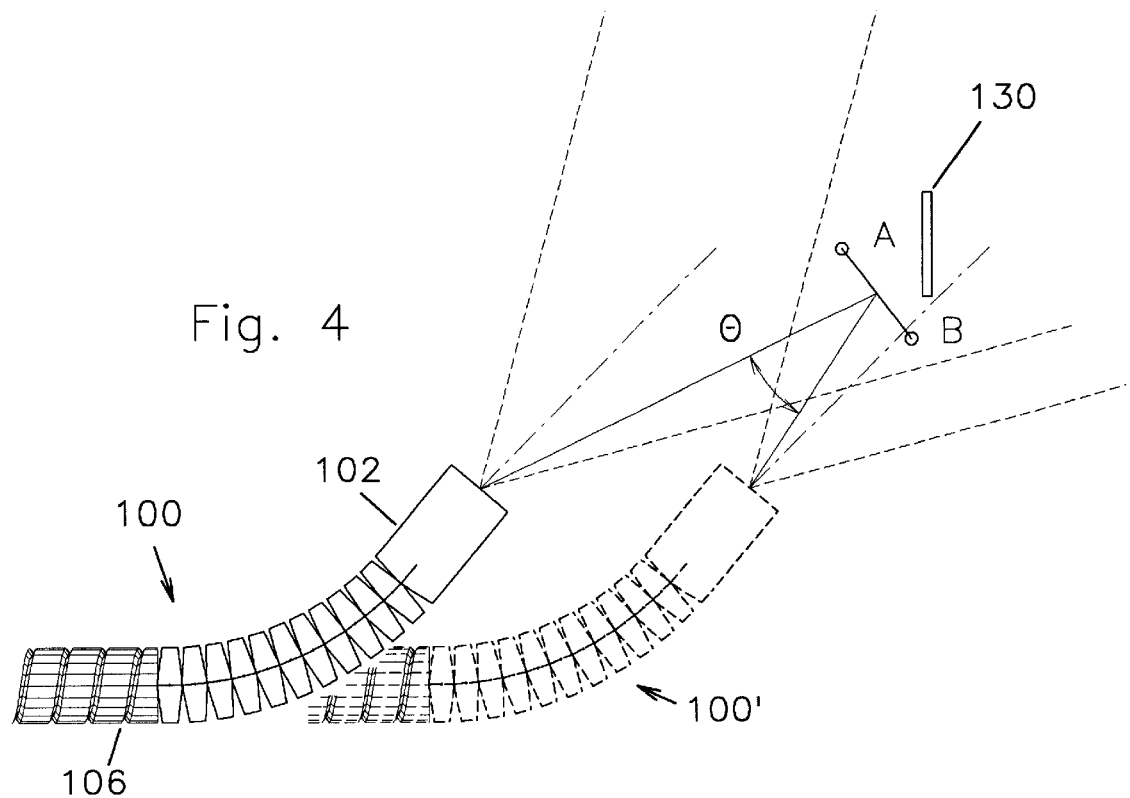
FIG. 4 depicts a measurement being made with a flexible endoscope being translated in the direction along its length. The angle subtended by two camera viewing positions at the midpoint between two points of interest on an object is denoted in this Figure by Θ.

The measurement can be made with any motion of imaging section 102 of endoscope 100 as long as that motion produces a translation of imaging section 102 (i.e., the perspective displacement) for which the subtended angle is substantially different from zero (and as long as the object and target array are both visible in both views). For instance, FIG. 4 depicts a measurement being made where endoscope 100 is advanced to a different position (denoted by 100') along the direction of flexible insert section 106 without any change of internal articulation between the views. The resulting subtended angle Θ is shown for a point which lies half way between points of interest A and B. The first principle states that angle Θ must be substantially different from zero at both points A and B.

In FIG. 5, the distal end of flexible section 106 of endoscope 100 has been manipulated so that the subtended angle Θ, depicted here as being viewed from a point on target array 130, has a much larger value than it does in FIG. 2. Clearly, the angles subtended at points A and B on the object will be much larger in this case as well. In U.S. Pat. No. 6,009,189, it was shown that the optimum range of angles for the subtended angle is 40 to 100 degrees. It was also shown that the overall optimum method for making the measurement is to achieve a situation such as that shown in FIG. 5 where the subtended angle is large, and where the object points of interest remain near the center of the endoscope's field of view, or at the scope's optimum field angle, if the latter is not the center of the field of view.

When only the internal articulation of the scope is used to move the camera between the two viewing positions, as was depicted in FIG. 2, the relationship between the subtended angle that can be achieved and the field of view of the scope is determined by the mechanical characteristics of the articulation motion. Clearly, for two scopes which use the same articulation mechanism but have different fields of view, the higher subtended angle can be achieved for the scope with the larger field of view. But, as pointed out in U.S. Pat. No. 6,009,189, the scope with the narrower field of view will have a lower effective pointing error, so one must carefully analyze the situation to determine which scope will provide the superior measurement results.

For the measurement of the instant invention, what one desires is that imaging section 102 translate as much as possible while rotating as little as possible. The worse a particular scope is in this regard, and the narrower its field of view, the more measurement precision there is to be gained by arranging the measurement to be made as shown in FIG. 5 instead of as shown in FIG. 2. With scopes of narrow field of view, or for special circumstances where the absolute best measurement precision is required, one should attempt to create a viewing situation such as that shown in FIG. 5. In this regard, scopes that have more elaborate articulation than the simple bending motion depicted in FIGS. 2, 4, and 5 are known and will be useful. An example is the articulation mechanism described by Haduch, et. al., in U.S. Pat. No. 4,530,568.

A third principle important to obtaining the best measurement precision is that if the video sensor (or the image measurement system, whatever it may be) has a higher resolution in one direction than the other, then that high resolution direction should be oriented parallel to the perspective displacement of the camera as projected onto the image. For instance, video measurement systems often have a higher resolution in the horizontal direction than in the vertical direction, and in that case, one should arrange the apparent horizontal video direction to be parallel to the plane of the Figure in any of FIGS. 2, 4, or 5.

It is necessary that at least three reference points in target array 130 can be viewed from each of the camera viewing positions. If the apparent positions of more than three reference points are located in each image, the random error in the measurement will be reduced. (There will be random error in the measurement, since it is not possible to locate the two dimensional positions of points in the image perfectly.)

If there are more than three reference points in array 130, it is convenient if all of these points are confined to a single plane as depicted in FIG. 1, because then it is easier to determine their relative positions accurately during fabrication. However, there are important reasons to use a non-planar array of reference points under certain circumstances. This issue is discussed further below in Section 2G. What is required is that the relative positions of all reference points in array 130 be known accurately in some three-dimensional reference coordinate system, and there appear at least three non-colinear reference points (that is, three points that do not lie along the same straight line in the reference coordinate system) in each image. (It is, of course, possible for the images of the three points to appear along the same line in the two-dimensional image.)

To get the best accuracy in the measurement, one does want to use a set of reference target points which has about the same physical size as the distance of interest on the object (as projected along the line of sight of the endoscope) and to be located as near as possible to the points of interest. This then allows the largest feasible subtended angle to be used when the endoscope is moved by using only its internal bending capability.

Many objects for which the dimensions are of interest are considerably smaller than the size of typical access ports. For instance, on jet engines, typical access ports are 8 to 10 mm. in diameter, while a typical object of interest has a dimension of about 1 mm. Thus, a reference target array with a maximum dimension of 3 to 6 mm. is a good general purpose size for this application, and will easily fit through the access ports.

While FIGS. 1, 2, 4 and 5 depict an endoscope that is substantially forward looking, the measurement can also be made with a side-looking endoscope. When a side-looking endoscope is used, and the internal articulation of the scope is used to perform the required motion of the camera, the endoscope is preferably bent in a plane which is perpendicular to the plane containing both the centerline of the field of view and the mechanical centerline of the endoscope. The reason is that the rotation of the camera then merely rotates the image about the line of sight, rather than adding to the apparent motion of the object as seen in the image; thus one can make use of a larger perspective displacement and obtain an advantage in reduced random error.

Of course, this measurement system is not restricted to measuring a single distance on the object; one can measure the three-dimensional locations of more than two points at a time. In addition, it is possible to implement the measurement using any other type of two-dimensional image measurement systems instead of the video camera and video cross-hair.

If a sufficient number of additional points are used in reference target array 130, and if these additional points are located in both images, then it is possible to do an optical calibration of the endoscope as well as to determine the camera motion between viewing positions, using only the data contained in two images. That is, the initial optical calibration of the endoscope referred to above is not strictly necessary. For general use, this alternate technique may be undesirable, since the location of additional target points on the video screen (FIGS. 3A and 3B) can be time consuming and tedious for the user. However, this alternate technique is of great interest if either the endoscope has not previously been calibrated or if the focus of the endoscopic camera is variable.

The image magnification produced by a camera at a particular object distance typically varies as the camera is adjusted to focus at different distances. Thus, a single optical calibration, done separately, may not be adequate for accurate metrology with an endoscope that is refocused to view objects at different distances. In this case, one can still make an accurate three-dimensional measurement using the new system being taught here; it simply requires locating additional reference points in each image. (One should keep the focus constant during an individual measurement, however.) The alternate measurement technique for uncalibrated cameras is explained below.

2. Operation of the Invention

A. Outline of the Perspective Dimensional Measurement Process

Complete details of the sub-processes of an improved perspective dimensional measurement have been provided in U.S. Pat. No. 6,009,189, referenced above. Because the new system of the instant invention uses some of these sub-processes in a different manner than does the previous system, the improved perspective dimensional measurement process is summarized here to help the reader understand exactly how to implement the new system.

The fundamental sub-process of the perspective dimensional measurement is to determine the positions of image points corresponding to points of interest on the object. When one does this for identical object points with the camera located at least two different observation positions, it is possible to locate the object points in three-dimensional space, thus determining the desired three-dimensional distances between object points. The two observation positions are denoted as P1 and P2, and can be considered to be the locations of the nodal point of the optical system of the camera in three-dimensional space.

If the camera is not perfectly focused on the object, it is more correct to consider P1 and P2 to be the locations of the center of the entrance pupil of the camera's optical system, but this makes no practical difference unless one is concerned about exactly how the magnification of the image varies from its calibrated value when the focus of the camera is varied between optical calibration and measurement.

The fundamental equation for making the perspective dimensional measurement is expressed in terms of the tangents of the angles at which a point of interest is viewed with respect to the x and y visual coordinate axes at the two viewing positions. These tangents are determined using the measured positions of the images of the point and the data from an initial optical calibration, as is described further below.

For each object point of interest, two vectors, called visual location vectors, are formed from the tangents of the angles, and are expressed as column matrices. These vectors are defined as:

$$\vec{d}_{v1} = \begin{bmatrix} \tan(\alpha_{x1}) \\ \tan(\alpha_{y1}) \\ 1 \end{bmatrix} \text{ and } \vec{d}_{v2} = \begin{bmatrix} \tan(\alpha_{x2}) \\ \tan(\alpha_{y2}) \\ 1 \end{bmatrix} \quad (1)$$

where, for instance, $(\alpha_{x1}, \alpha_{y1})$ are the angular positions for the point of interest that were determined at P1.

The physical position of the camera (more precisely, the position of either the nodal point or the center of the entrance pupil of the camera's optical system) in space is expressed as a vector, $\vec{r}_c$, in a coordinate system that I call the external coordinate system or the global coordinate system. The two camera viewing positions used in the perspective measurement are then referred to as $\vec{r}_c(P1)$ and $\vec{r}_c(p2)$.

Likewise, the orientation of the camera in space is expressed a rotation matrix, which describes the orientation of the camera's internal coordinate system with respect to the global coordinate system. The rotation matrix $R_c$ transforms any vector expressed in the global coordinate system into that vector as expressed in the camera's internal coordinate system. The matrix $R_c$ is the product of three individual rotation matrices, each of which represents the effect of rotation of the camera's internal coordinate system about a single axis:

$$R_c = R_z(\theta_z) R_y(\theta_y) R_x(\theta_x) \quad (2)$$

where $\theta_z$, $\theta_y$, and $\theta_x$ are the angles that the coordinate system has been rotated about the corresponding axes from the reference orientation where the camera's internal coordinate system is aligned with the global coordinate system. The orientations of the camera at the two viewing positions are then expressed as $R_c(P1)$ and $R_c(P2)$.

The vector connecting the location of the camera at viewing position P1 to the location of the camera at viewing position P2 is defined as the perspective displacement, $\vec{d}$. The displacement vector between the two viewing positions is calculated in global coordinates as:

$$\vec{d}_g(P2, P1) = \vec{r}_c(P2) - \vec{r}_c(P1) \quad (3)$$

The relative rotation of the camera between the two viewing positions is calculated as:

$$R_{12}(P2, P1) = R_c(P2) R_c^{-1}(P1) \quad (4)$$

Equation (4) simply says that the rotation of the camera between positions P1 and P2 is equivalent to the rotation of the camera at P2 minus the rotation it had at P1.

The perspective displacement is re-expressed in the camera's internal coordinate system at P1 by taking into account the rotation of the camera at that point. That is:

$$\vec{d}_{v1} = R_c(P1) d_g(P2, P1) \quad (5)$$

The location of the object point of interest in the measurement coordinate system is then computed as:

$$\vec{r}_m = \frac{1}{2} [\vec{d}_{v1} \quad R_{12}^{-1} \vec{d}_{v2}] [\vec{d}_{v1} \quad -R_{12}^{-1} \vec{d}_{v2}]^{LI} \vec{d}_{v1} \quad (6)$$

where the measurement coordinate system is parallel to the internal coordinate system of the camera at P1, with its origin located midway between P1 and P2. In Equation (6) the superscript "LI" denotes the left pseudo-inverse of a matrix.

Equation (6) expresses how to locate a point in a three-dimensional measurement coordinate system under completely general conditions, for any arbitrary positions and orientations of the camera, provided that these positions and orientations are known accurately in some global coordinate system. Equation (6) is the fully three-dimensional least squares estimate for the location of the point of interest. Once the coordinates of a number of points of interest are known in a single coordinate system, three-dimensional distances between these points are easy to calculate using the Pythagorean Theorem.

B. Determination of the Visual Location Vectors from Image Position Measurements The determination of the tangents of the angles used in Equation (1) uses data from an optical calibration. This process is outlined here.

The quantities that are directly measured are the positions of image point centroids on the image sensing plane of the camera. These measured positions must be corrected for a generalized distortion, where I use that term to refer to any deviation of the image position from the position that it would have if the camera were perfect according to the idealized imaging model discussed in U.S. Pat. No. 6,009,189, referenced above.

The correction of measured image point position data to form ideal image point position data can be expressed as:

$$\vec{rho}_{im} = \vec{rho}' - \vec{rho}_D = \begin{bmatrix} x'_{im} \\ y'_{im} \end{bmatrix} - \begin{bmatrix} f_{Dx}(\vec{rho}') \\ f_{Dy}(\vec{rho}') \end{bmatrix} \quad (7)$$

where $x'_{im}$ and $y'_{im}$ are the measured image point coordinates and $f_{Dx}$ and $f_{Dy}$ are functions that represent the distortion of the camera being used. After the image point positions are corrected with Equation (7), the visual location vector can be expressed as:

$$\vec{a}_v = -\frac{1}{i}\begin{bmatrix} \vec{rho}_{im} \\ -i \end{bmatrix} \quad (8)$$

where I previously called i the equivalent focal length of the camera. It could also be called a scale factor for the image. I now prefer the term "image projection distance" for the quantity represented by i.

The generalized distortion parameters, represented by functions $f_{Dx}$ and $f_{Dy}$ in Equation (7), are determined in the optical calibration process. In optical calibration the image positions of a large number of object points are determined, where the relative positions (in three dimensions) of each of the object points have previously been accurately determined and where a calibration coordinate system has been defined. Then, using the mathematical model of the imaging process and the distortion, and a nonlinear least squares optimization, best fit estimates for the location and orientation of the camera in the calibration coordinate system, the projection distance, i, and the parameters necessary to model the generalized distortion are determined. (The imaging model is represented here by Equations (7) and (8) and by Equations (13) and (15), given below.)

A particular model for the generalized distortion was disclosed in U.S. Pat. No. 6,009,189. Since that application was filed, I have made some refinements to the distortion correction process. These refinements represent the best mode of distortion correction for endoscopes that I am currently aware of. The generalized distortion is now represented by the third and fifth order axially symmetric Seidel aberrations together with an offset of the optical axis and different scale factors along two measurement directions. The new distortion correction, analogous to Equation (7) is:

$$\vec{t}_{im} = F[r\vec{h}o' - r\vec{h}o_{ic}] - \vec{t}_D(F[r\vec{h}o' - r\vec{h}o_{ic}]) \quad (9)$$

where, as before (Equation (7)), $r\vec{h}o'$ is either a 2×1 column vector of the measured image point position, or is a 2×N matrix of measured image point positions. The column vector $r\vec{h}o_{ic}$ is the offset of the optical axis with respect to the image measurement coordinate system. This offset is the same for all image points; if there is more than one point, then a 2×1 vector $r\vec{h}o_{ic}$ is multiplied by a 1×N vector of ones.

The scaling factor matrix, F, is defined as:

$$F = \begin{bmatrix} \frac{1}{i_x} & 0 \\ 0 & \frac{1}{i_y} \end{bmatrix} \quad (10)$$

where $i_x$ and $i_y$ are effectively, the projection distances for the x and y directions. There are two scaling factors because video measurements usually produce data that correspond to different physical distances on the camera image sensing plane for each increment of output. This fact was previously taken into account by specific terms within the distortion functions $f_{Dx}$ and $f_{Dy}$.

The quantity $\vec{t}_{im}$ calculated by Equation (9) contains the negative of the true tangents of the viewing angles rather than image coordinates, so that the visual location vector, in analogy with Equation (8), is now expressed as:

$$\vec{a}_v = \begin{bmatrix} -\vec{t}_{im} \\ 1 \end{bmatrix} \quad (11)$$

In Equation (9), the quantity $\vec{t}_D$ is the distortion aberration function, which is defined as:

$$\vec{t}_D(s) = [a(2|\vec{s}|^2 - 1) + b(6(|\vec{s}|^4 - |\vec{s}|^2) + 1)]\vec{s} \quad (12)$$

and which represents axially symmetric distortion of third and fifth orders, and in which $|\vec{s}|^2 = s_x^2 + s_y^2$. In Equation (12) the Seidel distortion is expressed in terms of the radial Zernike functions, rather than as simple powers of the variable. The Zernike functions are orthogonal over the unit circle, and since the tangents of the viewing angles extend over a region of about that size, the Zernike functions are much closer to orthogonal than are simple powers of the variable. I have found that using them this way helps convergence and stability of the nonlinear least squares parameter fit used in calibration.

C. Determining the Camera Positions and Orientations with a Calibrated Camera

In the present invention, the relative positions and orientations of the camera are not known prior to the analysis of measurement data. As described in Section 1, these quantities are now determined by use of reference target points which are inserted into the scene along with the object of interest. This process is analogous to what I previously called alignment calibration. We first assume that an optical calibration has been previously performed on the endoscope, so that the effective projection distances and distortion parameters of the camera are known. As mentioned above, it is possible to combine the two (optical and alignment) calibrations if additional reference target points are used; this case will be described in the following Section.

Reference target array 130 (FIG. 1) supplies a field of reference target points which have relative positions which are known to an accuracy which is better than one expects to make measurements. Unlike when optical calibration is being performed, it is not necessary that array 130 supply targets distributed over the full field of view of the camera, or over a significant range of distances from the camera. (This is true even if a fill combined calibration with additional reference points is being attempted, provided that target array 130 is close to the object to be measured and that the object does not have a lot of depth.)

Figure 6:
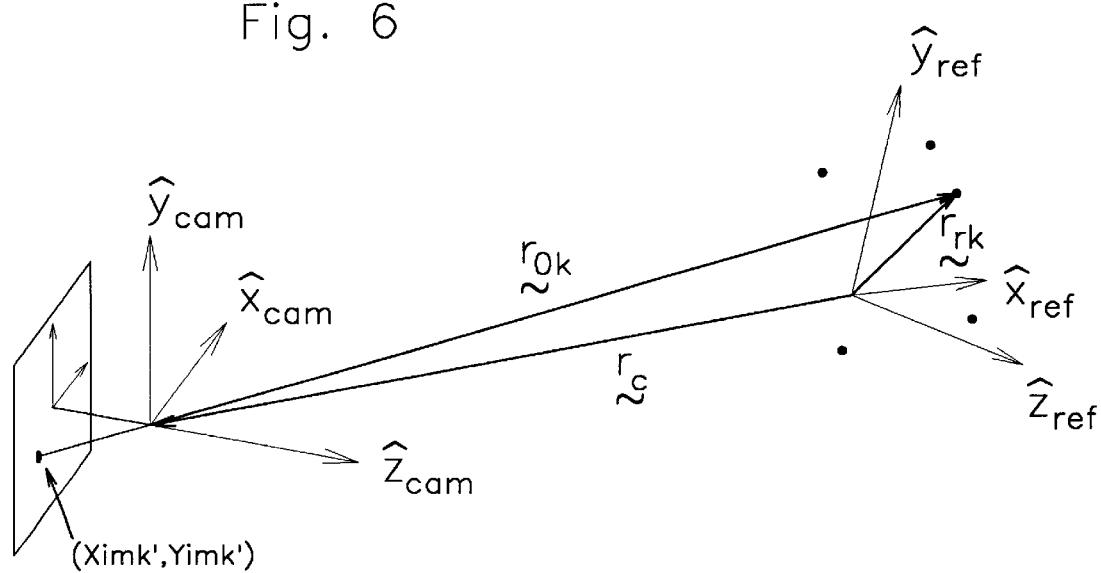
FIG. 6 shows the geometry of the determination of camera position and orientation.

The geometry of the camera position and orientation determination process is depicted in FIG. 6. In FIG. 6 the vector $\vec{r}_{0k}$, which is the (unknown) position of the kth reference target point in the camera coordinate system, can be written as:

$$\vec{r}_{0k} = R_c(\theta_x, \theta_y, \theta_z)[\vec{r}_{rk} - \vec{r}_c] \quad (13)$$

where $\vec{r}_{rk}$ is the known position of the kth reference point in the reference target array coordinate system (the reference coordinate system), $\vec{r}_c$ is the unknown position of the camera's nodal point in the reference coordinate system, and $R_c$ is the unknown rotation of the camera's coordinate system with respect to the reference coordinate system.

During the measurement, the reference target array is viewed from the two positions of the camera. According to FIG. 6 and Equation (13), one can write:

$$\vec{r}_{0k1} = R_c(P1)[\vec{r}_{rk} - \vec{r}_c(P1)]$$

$$\vec{r}_{0k2} = R_c(P2)[\vec{r}_{rk} - \vec{r}_c(P2)] \quad (14)$$

The visual location vectors, which are calculated from the distortion corrected image position data according to either Equation (8) or Equation (11), can also be written in terms of the coordinates of the reference points in the camera coordinate system as:

$$\vec{a}_{vk1} = \frac{\vec{r}_{0k1}}{z_{k1}} = \vec{r}_{0k1} u_{k1}$$

$$\vec{a}_{vk2} = \frac{\vec{r}_{0k2}}{z_{k2}} = \vec{r}_{0k2} u_{k2}. \quad (15)$$

Define the following quantities, where it is assumed that k reference points are used:

$$A_{v1} = [\vec{a}_{v11} \, \vec{a}_{v21} \, \ldots \, \vec{a}_{vk1}]$$

$$A_{v2} = [\vec{a}_{v12} \, \vec{a}_{v22} \, \ldots \, \vec{a}_{vk2}]$$

$$\vec{r}_{cal} = [\vec{r}_{r1} \, \vec{r}_{r2} \, \ldots \, \vec{r}_{rk}]$$

$$\vec{1}_k = [1 1 \ldots 1] \, (k \text{ components}) \quad (16)$$

$$U_1 = \begin{bmatrix} u_{11} & 0 & \ldots & \ldots & 0 \\ 0 & u_{21} & 0 & \ldots & 0 \\ 0 & 0 & \ddots & \ldots & 0 \\ \vdots & \vdots & \vdots & \ddots & \vdots \\ 0 & 0 & 0 & \ldots & u_{k1} \end{bmatrix}$$

$$U_2 = \begin{bmatrix} u_{12} & 0 & \ldots & \ldots & 0 \\ 0 & u_{22} & 0 & \ldots & 0 \\ 0 & 0 & \ddots & \ldots & 0 \\ \vdots & \vdots & \vdots & \ddots & \vdots \\ 0 & 0 & 0 & \ldots & u_{k2} \end{bmatrix}$$

Equations (14) can then be written as:

$$A_{v1} = R_c(P1)[\vec{r}_{cal} - \vec{r}_c(P1)\vec{1}_k]U_1$$

$$A_{v2} = R_c(P2)[\vec{r}_{cal} - \vec{r}_c(P2)\vec{1}_k]U_2 \quad (17)$$

Equations (17) represent 4k simultaneous equations in 12 unknowns, thus, they can be solved for k≧3. The unknowns are $R_c(P1)$, $R_c(P2)$, $\vec{r}_c(P1)$, and $\vec{r}_c(P2)$, each of which contains 3 unknowns. Because these equations are nonlinear, an iterative process is used to solve them. If there are 3 reference target points, then Newton's method can be used to find the exact solutions, as long as the errors in the measurements are not too high. (If the errors are too large, there may be no exact solution.) If there are more than three reference target points or if the errors are high, then a nonlinear least squares optimization process can be used to find best fit values for the unknowns.

Because Equations (17) are nonlinear, there is no guarantee that there exists only a single solution when k=3. This is discussed further in Section 2G below.

In the present case, where the internal calibration of the camera is known, there is no advantage to solving both sets of equations in Equation (17) simultaneously. That is, each of the sets is complete in itself, representing 2k Equations in 6 unknowns. This means that there is no advantage to using the same set of reference points at the first and second viewing positions. There must still be at least three reference points that are non-colinear in the reference coordinate system in each image, however.

The process of solving Equations (17) determines the camera positions and orientations relative to the reference coordinate system, which serves as the global coordinate system for the measurement (Section 2A, above). Once the camera positions and orientations are determined, one simply uses Equations (3) through (6), along with the visual location vectors determined for the object points of interest, to determine the three dimensional locations of these object points in the measurement coordinate system. Once the object points have been located, then one can calculate the desired three-dimensional distances, as discussed above.

D. Determining the Camera Positions and Orientations with an Uncalibrated Camera When the camera has not been previously calibrated, Equations (17) still apply; however, the arrays of visual location vectors $A_{v1}$ and $A_{v2}$ cannot be directly calculated from the image position measurements. Since the internal parameters of the camera are unknown, one must incorporate these unknowns into Equations (17).

From Equation (11) the visual location vector for a reference point k at viewing position j (i.e., j=1 or 2) is:

$$\vec{a}_{v_{kj}} = \begin{bmatrix} -\vec{t}_{lm_{kj}} \\ 1 \end{bmatrix} \quad (18)$$

From Equations (9) and (10) we have:

$$\vec{t}_{im_{kj}} = \begin{bmatrix} \frac{1}{i_x} & 0 \\ 0 & \frac{1}{i_y} \end{bmatrix} [\vec{rho}'_{kj} - \vec{rho}_{ic}] - \vec{t}_D \left( \begin{bmatrix} \frac{1}{i_x} & 0 \\ 0 & \frac{1}{i_y} \end{bmatrix} [\vec{rho}'_{kj} - \vec{rho}_{ic}] \right) \quad (19)$$

where $i_x$, $i_y$, and $\vec{rho}_{ic}$ are unknowns, and $\vec{rho}'_{kj}$ is the measured image position for reference point k at viewing position j.

From Equation (12), the second term on the right hand side of Equation (19) can be expressed in terms of the two distortion parameters, a and b. Thus, using Equations (18), (19), (12) and (16) the visual location matrices of Equations (17) can be expressed in terms of the measured image positions, the unknown camera positions and orientations, and the unknown internal camera calibration parameters, $i_x$, $i_y$, $\vec{rho}_{ic}$, a and b. Since there are six additional unknowns, Equations (17) now represent 4k simultaneous equations in 18 unknowns, thus they can be solved for $k \geq 5$. That is, at least five reference target points must be used if the camera has not been optically calibrated.

With an uncalibrated camera there is an advantage to solving both sets of Equations (17) simultaneously, because the internal camera calibration parameters are the same for both images (unless the focus of the camera is changed between acquisition of the first image and acquisition of the second image, something that is not recommended). That is, one prefers to use the same set of reference points in each image. If one were to use different sets of reference points in the two images, then there would be 12 unknowns to be determined from each image, thus a minimum of six reference points would be required, and one would obtain two different sets of estimates for the internal camera calibration parameters.

The minimum number of reference target points which must be used with an uncalibrated camera also depends on the number of parameters needed to model the imaging and generalized distortion. For instance, I have seen endoscopes in which both of the Seidel distortion parameters a and b were large, and others in which only parameter a was needed. If the measurement camera is such that there need be used only four or fewer parameters in the model, then the minimum number of reference points required is four.

The minimum possible number of parameters to model the imaging and distortion of any conceivable camera is one; that would be a camera with no distortion, no offset of the optical axis with respect to the measurement coordinate system, and only a single image projection distance. Of course such a camera would have to be specially built to have these properties.

As another example, the more general imaging model suggested in U.S. Pat. No. 6,009,189 uses a total of nine internal camera calibration parameters, so that with that model, there must be used at least six reference target points if the same points are used in both images. I have not found this model to be superior to the simplified model presented here as Equation (9) for endoscopes, but it may be preferred in more general embodiments of the measurement system.

Table I summarizes the minimum number of reference points required in each image for performing the new measurement method for various cases of interest. Of course, it is always a good idea to use more reference target points than the minimum number to reduce the effects of errors, if one can afford the extra time spent in making the measurement.

TABLE I

Minimum Number of Reference Points Required in Each Image

| | Generalized Distortion Model | | |
|---|---|---|---|
| Operation | Minimum $\leq 4$ parameters | Eqn. (9) 6 params. | 9 params. |
| Calibrated Camera | 3 | 3 | 3 |
| Uncalibrated - Same Reference Points | 4 | 5 | 6 |
| Uncalibrated - Different Reference Points | 4 | 6 | 8 |

Once Equations (17) have been solved using the reference target point data, the camera positions and orientations thereby determined are used in Equations (3) through (6). The visual location vectors of object points of interest are determined by substituting the internal camera parameters found from Equations (17) into Equations (9) through (12) along with the image position data for these object points. These visual location vectors are then used in Equation (6) to determine the three dimensional locations for the object points.

E. Summary of the Measurement Process

Figure 7:
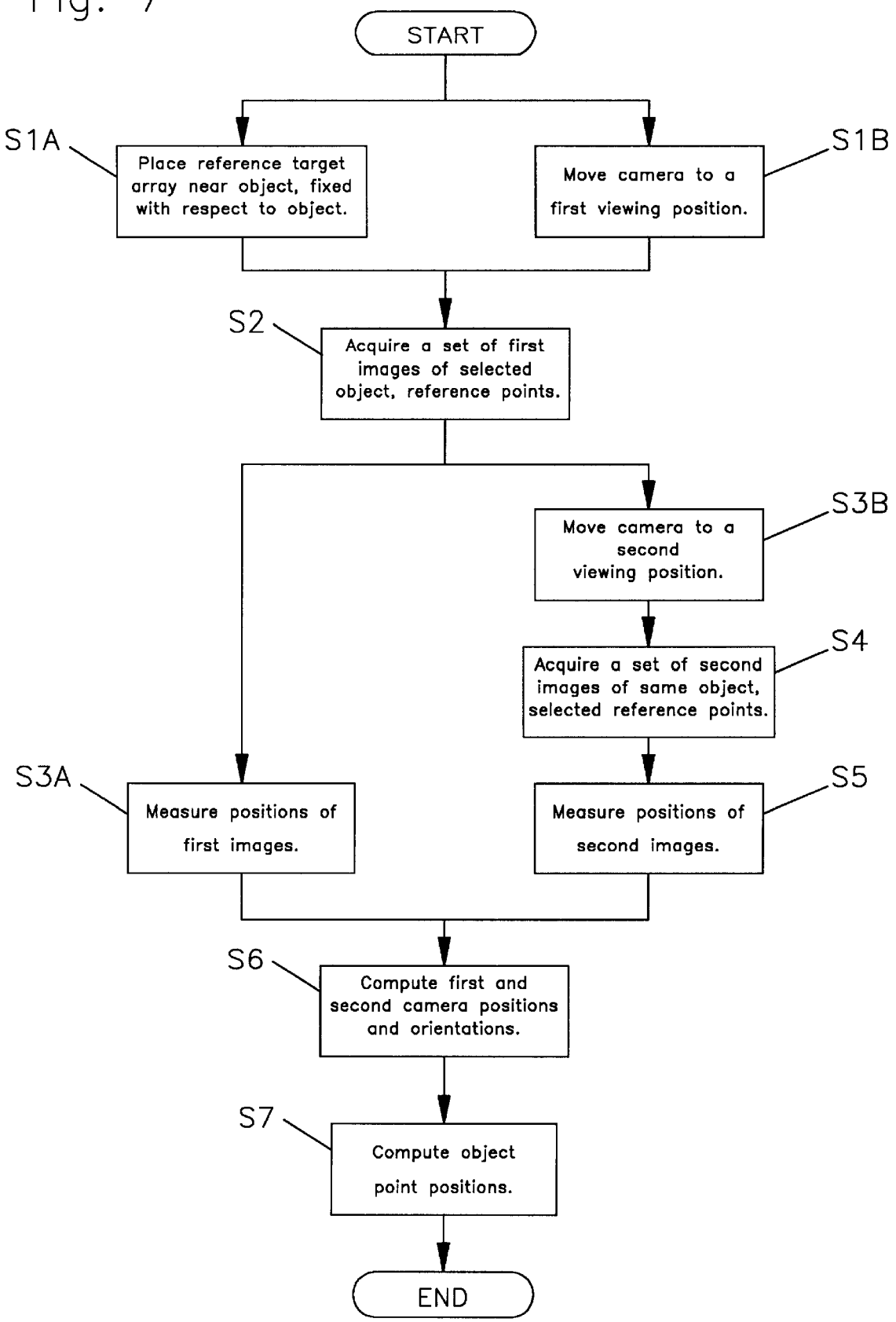
FIG. 7 is a flow diagram of the method for locating object points in three-dimensional space.

FIG. 7 is a flow diagram of the method for locating object points in three dimensions. In step S1A, one places the reference target array near the object and in step S1B, one positions the camera to a suitable first viewing position. Clearly either of these two steps can be done first; this is indicated in FIG. 7 by the fact that these steps are located in separate columns.

In step S2 of the process a set of images of the selected object points of interest, and the chosen reference points on the reference target array, is acquired. This means simply that a single image is acquired which contains images of all of these points.

In step S3A, one measures the positions of the images of the points that were selected in step S2. Clearly, this step can be accomplished either before or after steps S3B through S5, in which the camera is moved to a second viewing position, and in which a second image, containing a second set of images of the selected object points and a second set of images of reference points, is acquired and measured. Note that any suitable method of measuring the images could be used; the method is not restricted to being used with video systems.

It should also be clear that if the two images are stored, for instance as digital data by using a video frame grabber, that one could characterize the positions of the reference points on the reference target array after these images are acquired and/or after they are measured.

In step S6 of the process, one computes the camera positions and orientations at the two viewing positions as has been taught above. That is, one uses the measured positions of the reference point images at the two viewing positions, together with the predetermined relative positions of these reference points in the reference coordinate system and the camera internal calibration parameters to determine the camera positions and orientations. If the camera has been previously calibrated, one uses the known internal calibration parameters, otherwise one also calculates these parameters as part of step S6. If the camera has been previously calibrated or if different sets of reference points is used in the first and second images, then the camera position and orientation for the first viewing position is calculated separately from that for the second viewing position. However, if the camera has not been previously calibrated, and if the same set of reference points is used in both images, then the positions and orientations of the camera at both viewing positions are preferably computed together with the camera internal calibration parameters in a single step.

Finally, in step S7 of the process, one computes the object point positions in the measurement coordinate system using the camera positions and orientations, and the measured positions of the object point images, together with the internal camera calibration parameters.

Figure 8:
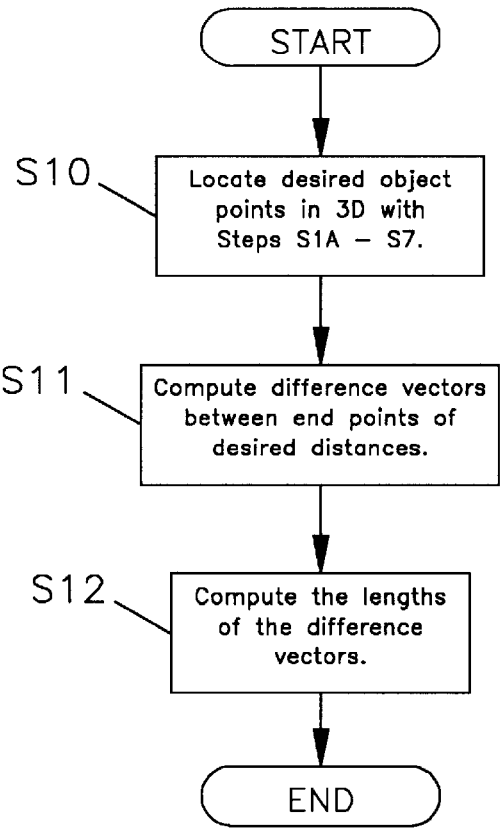
FIG. 8 is a flow diagram showing how the method for locating object points is used to determine distances between points on an object in the first measurement procedure.

In FIG. 8 is shown a flow diagram of the process of measuring the three-dimensional distances between a number of points on an object. In step S10 the process of FIG. 7 is used to locate the selected object points in a three-dimensional measurement coordinate system. In step S11, difference vectors are determined between the locations of points which represent the end points of the distances to be measured. Finally, in step S12, the lengths of these difference vectors are determined; these are the three-dimensional distances of interest.

F. Making a "Mode 2" Measurement

There is a second mode of measurement that is useful for certain situations, typically when the dimension to be measured is larger than can be contained within the field of view of the endoscope, or when the highest possible measurement precision is required.

Figure 9:
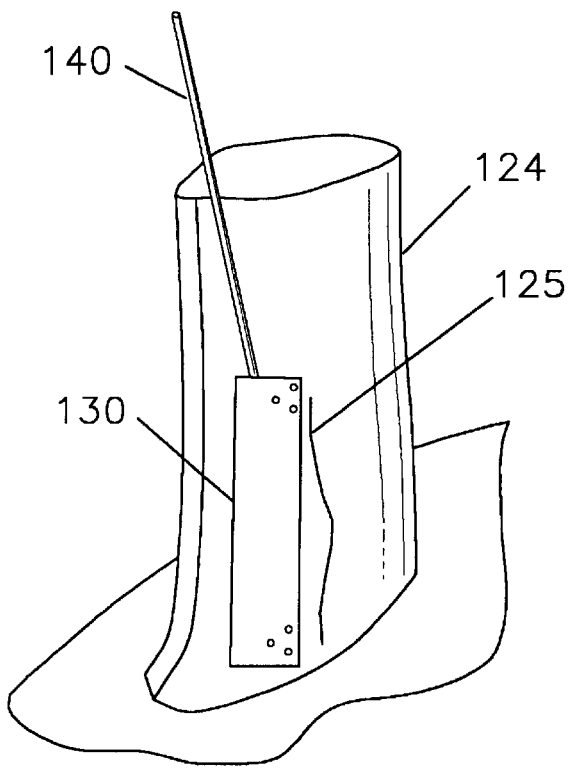
FIG. 9 depicts a measurement situation where a second measurement procedure can be used to advantage. The length of a relatively long crack in a machine part is to be determined.

In FIG. 9 is shown a machine part 124 containing a relatively long crack 125. Next to crack 125 is a long reference target array 130 oriented substantially parallel to crack 125. Target array 130 is supported by a support wire 140 as has been described.

In FIGS. 10A and 10B are shown the views that the user sees in the two steps of the first stage of the mode 2 measurement procedure. Just as before, on video screen 310 there is seen the apparent field of view of the endoscope, 312. Inside apparent field of view 312 is shown an image 125' of one end of the crack. Also shown is an image of the reference target array, 316, with images 132a', 132b', and 132c' of the reference target points with corresponding unprimed designations (shown, but not identified, in FIG. 9). Just as before, there are also one or more video cursors, 318, that enable the user to locate points on video screen 310.

In FIG. 10, cursor 318 has a different configuration than was shown in FIG. 3, as do the individual target points 132. This represents an alternative implementation of the measurement system. A more extensive discussion of the preferred characteristics of cursors and reference target points appears in Section 7, below.

In FIGS. 11A and 11B are shown the views that the user sees in the two steps of the second stage of the mode 2 measurement procedure. Here is seen an image 125' of the second end of the crack, together with images 132d', 132e', and 132f' of the reference target points with corresponding unprimed designations (shown, but not identified, in FIG. 9).

The concept of perspective measurement mode 2 is simple. FIG. 10 represents the process that has already been discussed for locating point A (that is, the first end of crack 125) in a measurement coordinate system defined by the location and orientation of the camera with respect to the coordinate system defined by reference points 132a, 132b, and 132c. Similarly, FIG. 11 represents the same process for locating point B (the second end of crack 125) in a measurement coordinate system defined by the location and orientation of the camera with respect to the coordinate system defined by reference points 132d, 132e, and 132f. But since points 132a–132f are all located on target array 130, the relative locations of all of the points are known. Thus, it is straightforward to determine the locations of both points A and B in a single coordinate system; that of reference target array 130.

In detail, the following procedure is used. As previously stated in connection with Equation (6), the measurement coordinate system is parallel to the internal coordinate system of the camera at P1, with its origin located midway between P1 and P2. That is, a point at a location $\vec{r}_m$ in the measurement coordinate system can be re-expressed in the reference coordinate system as:

$$\vec{r}_{ref} = \frac{1}{2}[\vec{r}_c(P1) + \vec{r}_c(P2)] + R_c^{-1}(P1)\vec{r}_m \tag{20}$$

Thus, Equation (20) is used after point A is located in the measurement coordinate system of the first stage of the mode 2 measurement procedure to determine the location of point A in the reference coordinate system, $\vec{r}_{rA}$. Likewise, Equation (20) is used after point B is located in the measurement coordinate system of the second stage of the procedure to determine the location of point B in the reference coordinate system, $\vec{r}_{rB}$. Then the distance between points A and B is simply the length of the vector $\vec{r}_{rA} - \vec{r}_{rB}$.

If desired, one could define a first reference coordinate system determined by reference points 132a, 132b, and 132c separately from a second reference coordinate system determined by reference points 132d, 132e, and 132f. Then the results of using Equation (20) for points A and B would refer to separate reference coordinate systems. However, one must know the relationship (that is, the translation between the origins, and the relative rotation) between these two reference coordinate systems in order to make the mode 2 measurement, and if one knows that relationship, then the locations of all of the reference points can always be reexpressed in terms of a single reference coordinate system as is assumed by the discussion immediately following Equation (20).

Mode 2 is useful when the scope has a side-looking geometry so that one can't easily adjust the position of the scope to get a view containing both end points of the distance at once. It is even more useful when one wants to obtain the most precise measurement possible of the distance between two points on an object, because one can move the camera very close to each point while locating them individually. As was taught in U.S. Pat. No. 6,009,189, the most important factor that determines the precision of the perspective dimensional measurement is the range (distance) between the camera and the object.

In FIGS. 9, 10, and 11, target array 130 is shown as containing only target points 132a through 132f. This was done for simplicity of explanation of mode 2 operation. However, for general purpose use, it is preferred to use a multiplicity of points extending along the full length of target array 130, because then objects with a range of different lengths can be measured using a single target array. When this is done, it is even more important than usual to mark the surface of array 130 with identification marks for each individual reference point, so that each individual point can be identified by the user without confusion as he or she views the video monitor as in FIGS. 10 and 11.

Figure 12:
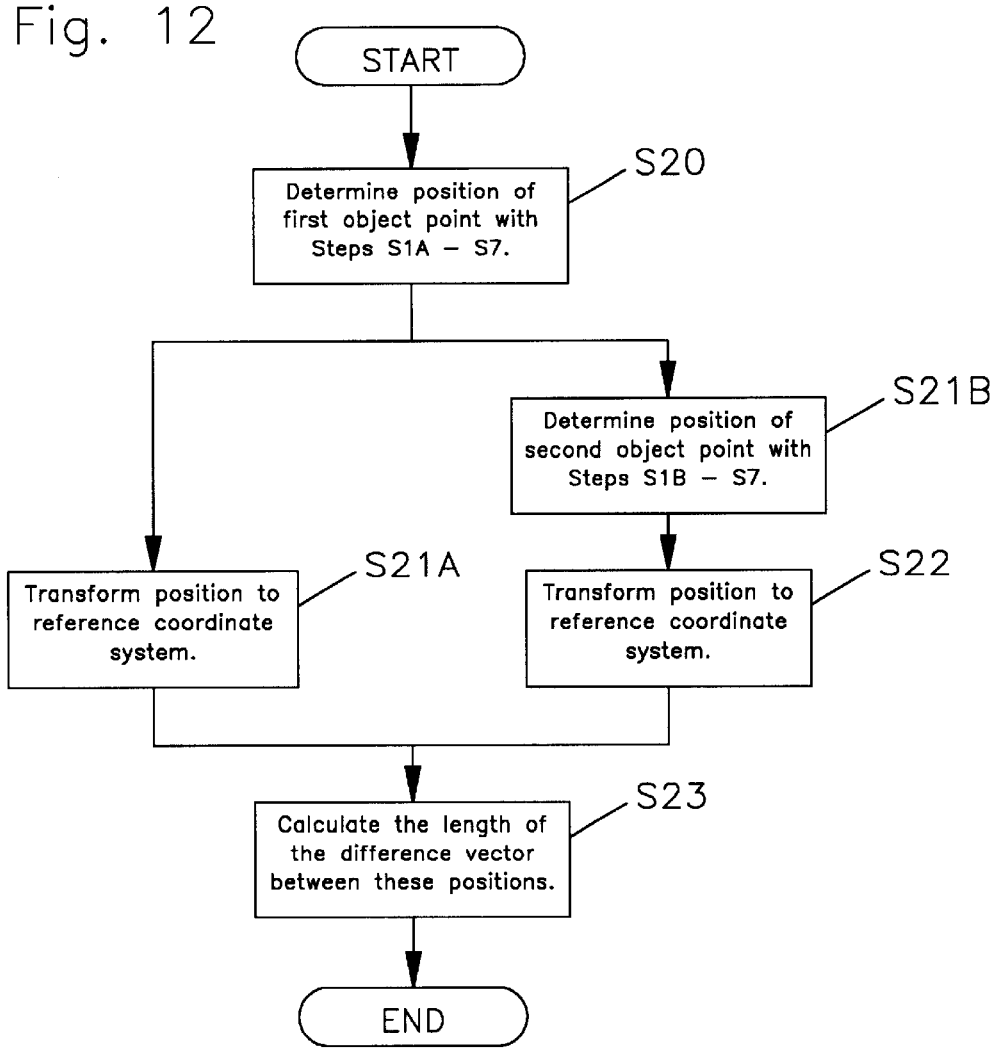
FIG. 12 is a flow diagram of the second measurement procedure for determining a distance between two points on an object.

FIG. 12 is a flow chart of the mode 2 measurement process. In step S20, one determines the position of a first end point of the distance in a first measurement coordinate system using the procedure of FIG. 7. In step S21A, this position is transformed to the reference coordinate system using Equation (20). Clearly, this step may be performed either before or after steps S21B and S22, in which the position of the second end point of the distance is determined first in a second measurement coordinate system, and then in the reference coordinate system. Finally, in step S23, the three-dimensional distance between the two end points is calculated.

G. Use of a-priori Information and Three-dimensional Reference Target Arrays

It was stated above that at least three reference target points are required to determine the location and orientation of a camera. A similar statement can be found throughout the literature in the field of photogrammetry, however, I have never found a photogrammetric project described where only this absolute minimum number of "control" points is used. In the normal practice of photogrammetry, one uses many more points than the absolute minimum in order to guarantee high accuracy, and to help ensure that the iterative solution to Equations (17) converges. As a result, the art of photogrammetry does not teach all of the requirements one must meet in order to use the minimum number of reference points.

On the other hand, in endoscopic measurements, one is very interested in using the minimum number of reference target points since it is important to minimize the time needed to perform the measurement. The fact that the accuracy required is lower than that expected from photogrammetry tends to lend support to the idea that using the absolute minimum number of reference points is feasible in endoscopic measurements.

Figure 13:
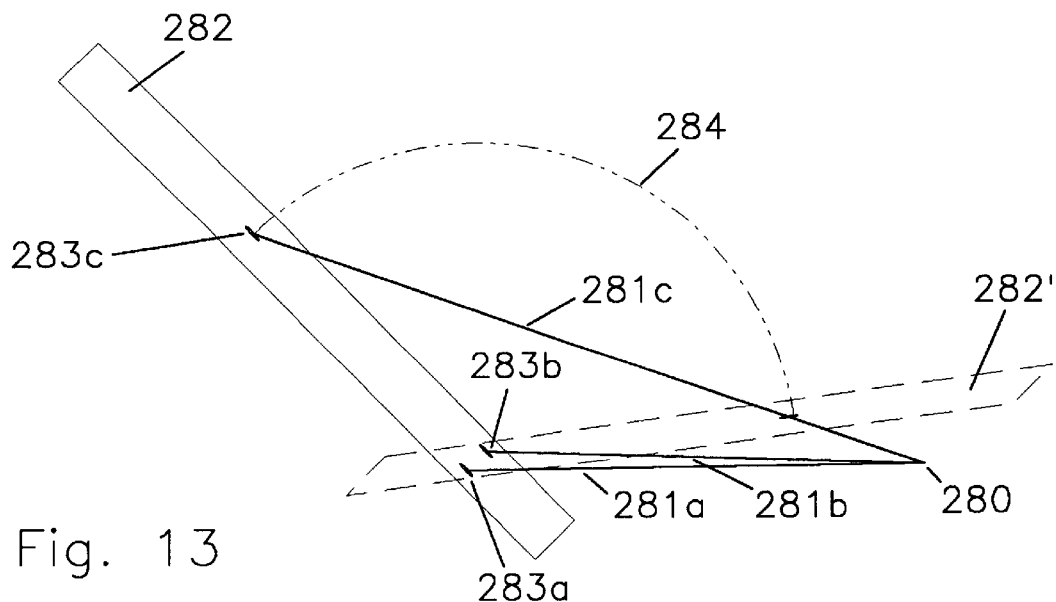
FIG. 13 depicts the relationship between three fixed optical rays and two orientations of a reference plane that contains a set of three reference points that matches the rays in both orientations.

It was also stated above that the fact that Equations (17) can be solved when there are three reference points does not mean that there will be a unique solution. In fact, there can be more than one solution for the camera position and orientation. An example is shown in FIG. 13. In FIG. 13 are shown three light rays, 281a, 281b, and 281c, which have a common point at a center of perspective 280. Center of perspective 280 could be, for instance, the nodal point of a camera lens. Then rays 281 represent the object space projection of a particular three-point image formed within the camera.

Assume that rays 281a, 281b, and 281c are associated with corresponding points of interest 283a, 283b, and 283c on a reference plane 282. Further assume that ray 281c, when projected into the plane of rays 281a and 281b, bisects the angle between rays 281a and 281b. Another way of stating this assumption is to say that the triangle formed in reference plane 282 by points 283a, 283b, and 283c has equal angles at its base 283a–283b, i.e. it is an isosceles triangle.

If reference plane 282 along with points 283 is then rotated about the line connecting points 283a and 283b, point 283c will pass through space along a circular path 284 shown as a broken line. In particular, when plane 282 takes the orientation denoted by 282' point 283c will again lie along ray 281c. Thus, there are two orientations of reference plane 282 with points 283a, b, and c which match the pattern of rays 281a, b, and c. Stated another way, there are two combinations of camera position and orientation which will produce the assumed image from the assumed set of three reference points.

I believe that it is likely that there will always be two solutions to Equations (17) when only three reference points are used, but I have not proven this conjecture, and do not wish to be bound by it. When more than three points are used, the likelihood of there being multiple solutions is reduced, in that in most cases, four or more points will not match the same number of rays at more than one orientation of reference plane 282.

In any event, since it is possible for there to exist at least two solutions to Equations (17), it is necessary to have some criterion for determining which solution is the correct one. As stated above, a solution to Equations (17) is determined by an iterative process. This iterative process must begin at some starting point which amounts to an initial guess at the solution. The iterative process will then converge to the actual solution which is "closest" to the starting point.

Determining the correct starting point when there is more than one solution requires that the user provide additional information. I refer to this additional information as "a-priori" information. The a-priori information can be as simple as the user indicating which reference point is closest to or which reference point is furthest from the camera. Note that in FIG. 13, this piece of information allows one to determine which of the two solutions is the correct one.

Figure 14:
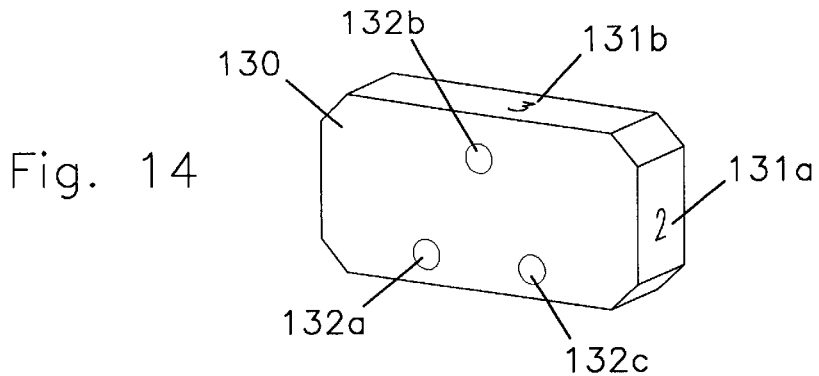
FIG. 14 shows a reference target array containing orientation indicia.

However, it will often be difficult for the user to determine which reference point is closest to or furthest from the camera. To make this easier one can add features to the reference target array. In FIG. 14 is shown a reference target array 130 with three reference target points 132a, 132b, and 132c located, for instance, at the positions indicated by the circles. On the edges of array 130 are marked array orientation indicia 131; in the Figure two of these indicia are visible, denoted as 131a and 131b. The orientation of the reference coordinate system is predetermined with respect to orientation indicia 131. For instance the reference x axis could be defined as the line containing reference points 132a and 132c with point 132c being defined as lying at positive x with respect to point 132a. Given that, then it is clear that the camera is located largely at positive x when index mark 131a (i.e., "2") is visible. Thus the user can simply indicate which of indicia 131 are visible, and this gives the needed a-priori information for the starting point for the iterative solution of Equations (17).

When there are only three reference points, the reference array is planar, by definition. If more than three points are used, there is the possibility of having a three-dimensional reference array. Consider again FIG. 13, but assume that the initial position of reference plane 282 was much closer to being normal to ray 281c, and that reference point 283c matches ray 281c for this new case. Then it is clear that the two solutions which match rays 281 to reference points 282 would involve orientations of reference plane 282 that are much closer together than in the situation depicted in FIG. 13. That is, when the reference plane is viewed nearly normal to its surface, there may be two camera positions which are close together which solve Equations (17). This implies that, in the presence of measurement noise, the error in the camera position will be increased when the camera views the reference array nearly perpendicular to its face.

The same consideration can be understood by examining the rate of change of shape of a triangle as it is viewed from different directions. This rate of change will be a minimum when the triangle is viewed perpendicular to its plane. This consideration holds even if there are more than three reference points in the plane, because it holds for every set of three points in the plane.

The importance of this is that when a planar reference target array is used, the measurement error is significantly reduced when the array is viewed far off the normal at both camera viewing positions, because the camera can be more accurately located under those conditions.

This amounts to an additional requirement for the use of a planar reference target array. As stated above in Section 1, in connection with FIG. 5, the optimum measurement occurs when the subtended angle, Θ, lies between 40 and 100 degrees. In FIG. 5, the array is being viewed at a large angle off normal at both viewing positions, thus the new condition being discussed here is satisfied. However, FIG. 5 is drawn with reference target array 130 taking a particular orientation with respect to the camera positions. Target array 130 could be rotated in the plane of FIG. 5 without affecting subtended angle Θ, but if it were, one of the camera views would become closer to normal to array 130 than is shown. Thus, when a planar reference target array is used, there is the new requirement that the normal to the array be oriented more or less to bisect the camera viewing positions (or it must be rotated far from the plane containing the two camera positions and the center of the array). If this is not done, the measurement error will be increased.

Notice that the orientation indicia 131 shown on the reference array in FIG. 14 will be visible only when the camera views the array at a large angle from the normal to the array. Thus the use of such indicia is consistent with the new requirement, in that the measurement can be made with small error when the user can read the indicia.

This requirement on reference array orientation can be largely eliminated if at least four reference points are used and if these points are not confined to a plane. Three dimensional reference arrays are discussed in detail below in Section 6. Consider, for instance, the array shown in FIG. 34. That reference target array has four reference points confined to a plane, and a fifth point which is located some distance in front of that plane. When this target array is viewed perpendicular to the plane containing the first four points, the apparent location of the single off plane point with respect to the other four points is very sensitive to changes in the viewing angle. Use of this single off-plane point is sufficient to greatly reduce the measurement error when viewing the reference target array at small angles with respect to the plane of the points.

Figure 15:
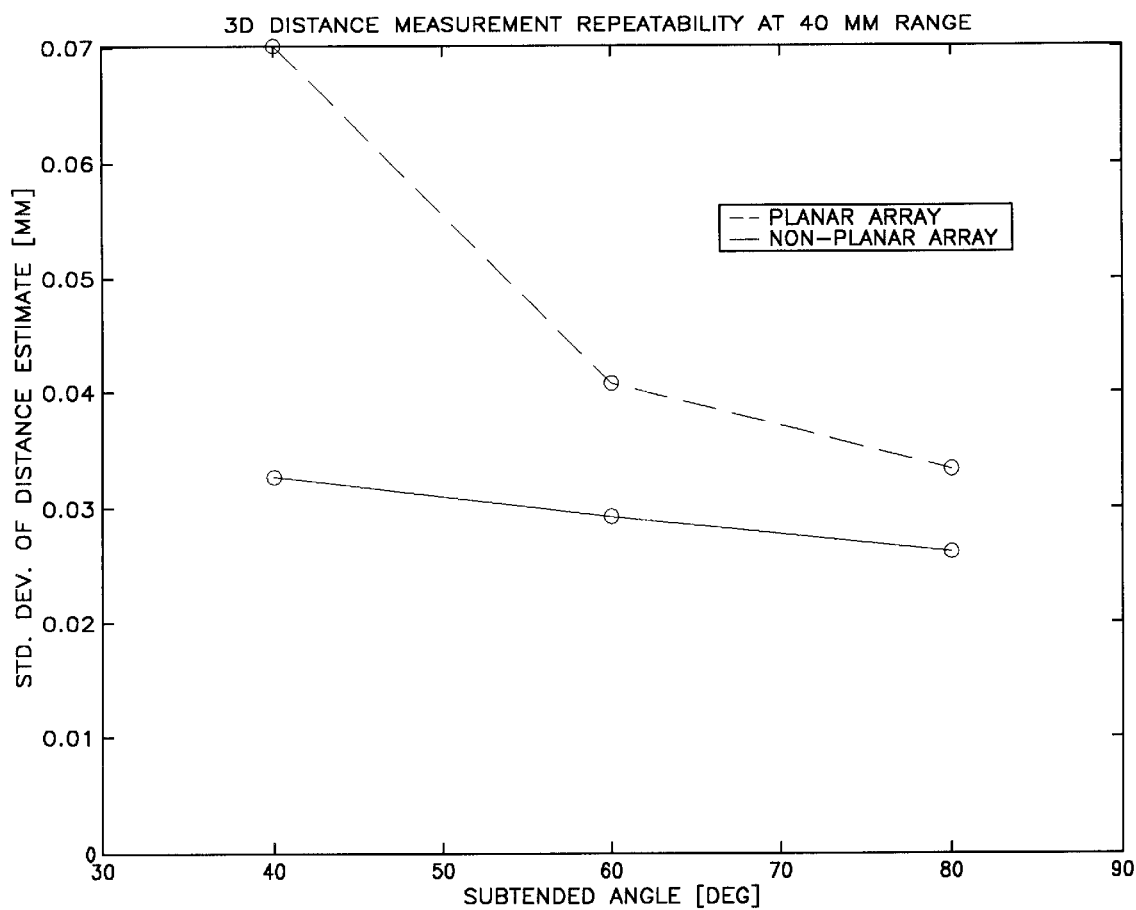
FIG. 15 compares the distance measurement error made when using a four-point planar reference target array to the error made when the four points are not confined to a plane.

FIG. 15 compares the relative performance of two 4 point reference arrays, calculated for a particular endoscope, video system, and object to be measured. In one case, all of the reference points are confined to a single plane ("PLANAR ARRAY"); in the other, one of the points is separated from the base plane determined by the other three. It was assumed that the viewing positions were equally spaced about the normal to the base plane of the reference array, so that the off-normal angle ranged from 20 to 40 degrees. One can see that the measurement error increases rapidly when the planar array is used at small off-normal angles, though it works almost as well as the non-planar array when the off-axis angle reaches 40 degrees. (At higher off-axis angles, the difference in performance becomes even smaller.)

A non-planar reference target array is superior because one need not be concerned with the orientation of the reference target array with respect to camera viewing positions. However, a planar array is easier to fabricate and characterize, so there is no single answer to which one is preferred. If one can guarantee that the normal to the array will always be at a large angle with respect to both viewing positions during a measurement, then the planar reference target array is satisfactory. If one cannot meet this requirement, then the non-planar array will be preferred, and one must pay the cost of accurate three-dimensional characterization of the array. Practical solutions for reducing this cost are discussed below in Section 6.

3. Description of a Second Embodiment

A second apparatus suitable for making measurements with my new method is shown in the side elevation view of FIG. 16. FIG. 16 depicts a substantially side-looking rigid borescope, represented by a borescope insertion tube 402, which is viewing a reference target array 130 and an object of interest 120. It is to be understood that insertion tube 402 is the distal portion of a borescope which has been connected to a suitable video camera and video measurement system, or other suitable image measurement system. It is also to be understood that reference array 130 may be a three-dimensional reference array, such as one of those discussed below in Section 6, instead of the planar reference array shown in FIG. 16. It is to be further understood that a suitable set of reference target points have been marked on array 130 although these are not shown in FIG. 16. The marking of target array points is discussed in detail in Section 7, below.

Object of interest 120 is contained within an enclosure 121, which has a wall 126, which is shown in fragmentary cross-section. Wall 126 contains an inspection port 127, which in turn contains inspection port threads 128. Mounting threads 162 of a borescope support body 160 have been engaged with inspection port threads 128. A mounting locknut 170, shown in cross-section, acts to secure support body 160 to wall 126, while allowing support body 160 the freedom to assume any desired rotational orientation about its long axis.

Borescope support body 160 also comprises a body housing 164, and a clamping screw 166. Support body 160 supports borescope insertion tube 402, and allows its position to be adjusted as required, while ensuring that the scope is held steady with respect to enclosure wall 126. At a minimum, support body 160 allows the borescope to be translated along its long axis, and rotated about that axis. Borescope support body 160 can be, for instance, that taught by Feuerstein, et. al., U.S. Pat. No. 3,917,432, the disclosure of which is incorporated herein by reference.

A portion of the left hand side of body housing 164 has been cut away to the centerline to reveal a support wire slot 168. Slot 168 is shown in front elevation view in FIG. 17. A reference target support wire 140 has been placed into slot 168 in such a manner that wire 140 is temporarily bent at slot 168 by the combined action of slot 168 and locknut 170. Target support wire 140 has an optional handle 144 for ease in manipulation. Wire 140 also has a permanently bent section 142 which spaces target array 130 away from borescope insertion tube 402 to the distance required for the application.

Support wire 140 is fabricated from spring steel or another suitable material so that any portion of its straight section can be bent substantially as shown in FIG. 16 without exceeding its elastic limit. Thus, the originally straight portion of wire 140 remains straight on either side of slot 168 and inspection port 127 as shown. Wire 140 can be either advanced into or retracted from enclosure 121 by pushing or pulling handle 144. Wire 140 and target array 130 will remain at the position selected due to the friction between wire 140 and slot 168 and the upper threads of locknut 170.

The apparatus shown in FIG. 16 is used as follows. Support wire 140 is introduced into slot 168 at some position along the straight portion of wire 140. Then nut 170 is fed over target array 130 and wire 140 and introduced to mounting threads 162. As nut 170 is threaded onto threads 162, wire 140 gradually assumes a greater bend at slot 168. Nut 170 is threaded almost fully onto threads 162 of support body 160.

Next, target array 130 and bent section 142 of support wire 140 are inserted through the open inspection port 127 until mounting threads 162 of support body 160 are introduced into inspection port threads 128. The assembly of support body 160, mounting locknut 170, and support wire 140 is then rotated with respect to enclosure wall 126 to advance mounting threads 162 into inspection port threads 128. When the thread engagement is judged to be sufficient, the rotation of the assembly is adjusted to place target array 130 at approximately the desired rotational angular position with respect to object 120. Locknut 170 is then rotated to bear against the upper surface of enclosure wall 126.

Borescope insertion tube 402 is then inserted into support body 160 from the top in FIG. 16. Clamping screw 166 is released for this purpose. The borescope is advanced into enclosure 121 and rotated about its long axis in order to achieve the desired position with respect to the object of interest. Clamp screw 166 is then tightened to maintain the borescope at this position. Wire 140 is further manipulated, advanced and/or rotated, as desired to get the required relationship between the object and target array 130. If necessary, locknut 170 is momentarily loosened, and support body 160 is rotated in order to adjust the lateral position of array 130 with respect to object 120.

When the view in the video screen (for example, FIG. 3A) is satisfactory, clamp screw 166 and locknut 170 are tightened fully and image position data is acquired for the points of interest on object 120 and the reference target points on array 130, as explained previously. Then clamping screw 166 is loosened, and the borescope is advanced or retracted to a second viewing position, for example as shown by 402' in FIG. 16 (and as was shown in FIG. 3B). Once again, image position data are acquired, and the data are processed as explained earlier to determine the required dimensions on the object.

This second embodiment thus enables one to perform the new perspective dimensional measurement with a side-looking rigid borescope. The implementation shown here also demonstrates that the reference target array can be mounted through the same inspection port that serves the borescope.

If one is concerned about contact between the object of interest and target array 130, one initially inserts support wire 140 into slot 168 so that target array 130 extends into the enclosure only a small distance when support body 160 is introduced into the inspection port. One then inserts the borescope and obtains a view of the target array. One then advances both the target array and the borescope in steps, monitoring the position of target array 130 with respect to the object as the insertion process proceeds.

Support wire 140 may be circular in cross-section, as shown, or it may be polygonal, if there is no need to adjust the angular orientation of target array 130 with respect to the line of sight of the borescope. Handle 144 can be formed from a simple loop of wire 140 itself, or it can be dispensed with entirely.

Making the width of slot 168 larger than the cross-sectional size of wire 140 gives some ability to adjust the position of array 130 in the direction perpendicular to the view of FIG. 16.

The shape and size of permanently bent section 142 of support wire 140 is also determined solely by the requirements of the application. As explained previously, there is no requirement that reference target points be positioned extremely closely to the points to be measured, but one does want to get two good views of both the points on the object and points on the reference target array. With this embodiment, advantageous mode 2 measurements are largely restricted to dimensions which lie parallel to the long axis of the borescope.

A variant of the second embodiment is shown in FIG. 18, where the mounting locknut is not used. This variant relies on the force necessary to bend support wire 140 to secure mounting threads 162 of support body 160 into threads 128 of inspection port 127. The apparatus shown in FIG. 18 is used as follows. First, target array 130 and bent section 142 of support wire 140 (FIG. 16) are inserted through the open inspection port 127, so that the straight portion of wire 140 extends out of port 127. Then, slot 168 is aligned with wire 140, wire 140 is moved to the edge of port 127, and mounting threads 162 of support body 160 are introduced into threads 128. Support body 160 and support wire 140 are then rotated together with respect to enclosure wall 126 to advance mounting threads 162 into threads 128. As this process proceeds, wire 140 is forced to bend further, thus there is an increasing load on the threads. When the threads have advanced enough to obtain what is judged to be adequate stability, support body 160 is rotated a final amount to position target array 130 rotationally with respect to the object to be measured. The borescope is then inserted into support body 160 and the measurement proceeds as described above.

Just as in the first embodiment, if the images are captured in a short exposure time one can hand hold the borescope instead of using a support body. The reference target array must be supported fixed in position with respect to the object during the time necessary to acquire both images.

4. Description of the Third Embodiment

Figure 19:
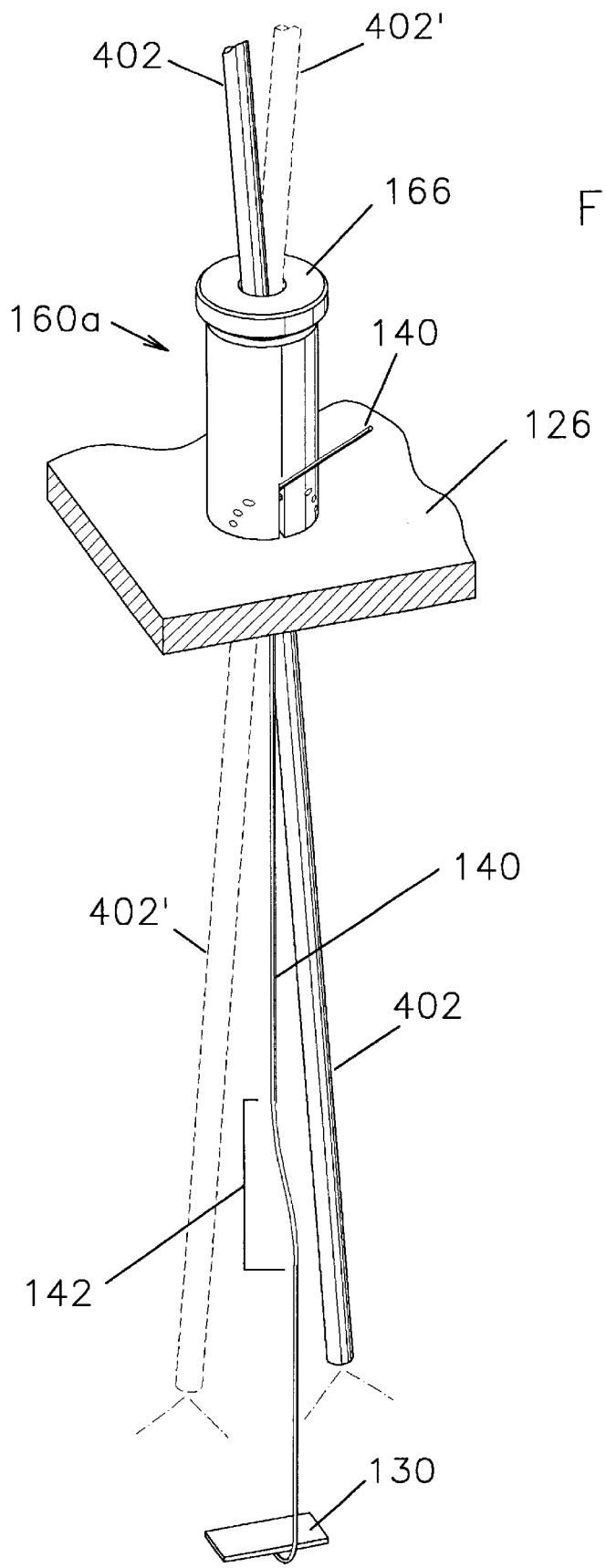
FIG. 19 is a fragmentary perspective view of a third embodiment of a measurement apparatus according to the present invention, using a forward-looking borescope.

FIG. 19 is a fragmentary perspective view depicting a third embodiment of the measurement system. This embodiment can use a substantially forward looking rigid borescope, as represented by insertion tube 402. A first position of the borescope is shown at 402 and a second position is shown at 402'. Borescope support body 160*a* is similar in many respects to support body 160 which is used in the second embodiment, but it also has important differences. A side elevation view of support body 160*a* is shown in partial cross-section in FIG. 20.

An object of interest is to be understood as being located in the vicinity of reference target array 130. Once again, array 130 may be a three-dimensional array instead of the two-dimensional array depicted in FIG. 19. In this third embodiment, borescope support body 160*a* allows a rotational motion of the borescope about a point near the inspection port (not shown) in enclosure wall 126. This rotational motion corresponds to a shift as well as a rotation of the distal tip of the borescope; thus it enables the perspective dimensional measurement. Just as in the second embodiment, a permanently bent section 142 of support wire 140 can be used to position the target array away from the axis of borescope motion, if that is required for the application.

It is to be understood that the proximal end of the borescope is attached to an image measurement system, which is capable of making two dimensional measurements on an image, as previously discussed.

Support body 160*a* has an alternate mounting arrangement for target support wire 140. As shown in FIG. 20, a support wire slot 168 intersects a support wire bore 169, so that the support wire can be captured within body 160*a* without the use of a locknut. A plurality of wire locating pins, 172, are inserted through matching bores in body housing 164 so that support wire 140 is captured between pins 172 and curved slot face 174.

Support body 160*a* is a modification of the body taught by Feuerstein, et. al., U.S. Pat. No. 3,917,432, which was incorporated herein by reference above. In that prior art device, a pair of spherical bearings are used internal to body housing 164 to allow a small amount of steering of the borescope line of sight. Here the amount of angular steering is limited along one axis to allow for the presence of mounting arrangements for wire 140. Just as in Feuerstein, when clamping screw 166 is loosened, the borescope may be slid axially (up and down in FIGS. 19 and 20) to achieve the inspection depth necessary, and the borescope may be steered about a point inside body housing 164. When clamping screw 166 is tightened, the borescope is prevented from moving with respect to the support body.

The specific example shown in FIG. 20 uses cylindrical bearings instead of spherical bearings to constrain the angular motion of the borescope. This motion is restricted to a rotation about an axis that lies in the plane of FIG. 20. The cylindrical bearings are represented in FIG. 20 by upper bearing half 176 and lower bearing half 178, which appear flat in this view, but which would appear to have a circular interface in a front or rear elevation view. Just as in Feuerstein, there is a symmetrical pair of bearings (not shown) located near the upper end of body housing 164 which cooperate with the bearings shown to provide the specified rotational degree of freedom to the borescope when clamping screw 166 is loose.

To use this third embodiment, one first inserts the proximal end of support wire 140 into bore 169 and pushes the wire past pins 172 so that it lies substantially against slot face 174. One continues to push wire 140 into support body 160*a* until target array 130 is located at a suitable starting distance from body 160*a*. One then carefully maneuvers target array 130 through the inspection port and then inserts support body 160*a* into the port and rotates it until a sufficient length of mounting threads are engaged. Just as in the second embodiment, a locknut can be used on the mounting threads of support body 160*a* if necessary for stability and/or rotational adjustment.

With clamping screw 166 loosened, one then inserts insertion tube 402 of a borescope into the support body. The borescope is advanced and rotated as allowed by support body 160*a* until a suitable view of an object of interest is obtained. Clamping screw 166 is then tightened. The whole assembly of borescope, support body, support wire, and target array is rotated a small amount as necessary to obtain the best orientation for the desired inspection. Then support wire 140 is manipulated to place target array 130 at the position required to make the desired measurement on the object of interest. Just as with the second embodiment, if there is the possibility of damaging something within the inspection enclosure, one advances target array 130 and borescope insertion tube 402 together while making frequent checks. Finally, a first viewing position is chosen by loosening clamp 166, rotating the borescope about the axis provided within body 160*a*, and then tightening clamp 166.

A measurement is made by capturing or characterizing an image with the borescope at a first viewing position (402), as shown in FIG. 19, then once again loosening clamp 166, rotating the borescope about the axis provided within body 160*a*, tightening clamp 166, and then capturing or characterizing a second image with the borescope at the position denoted by 402'.

Figure 19A:
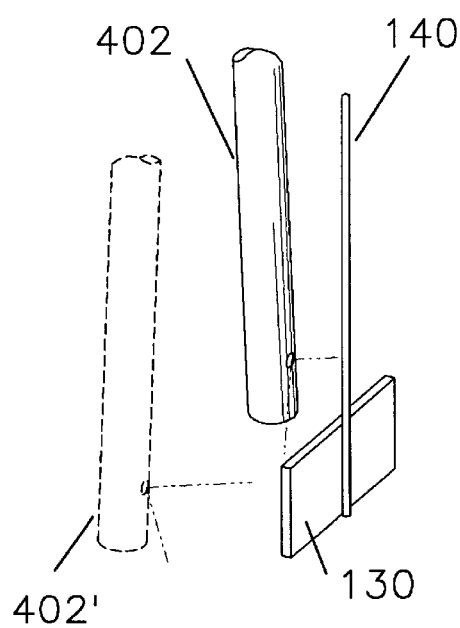
FIG. 19A is a close up view of a variant of the third embodiment, using a side-looking borescope.

This third embodiment can also be used with a side-looking rigid borescope, as shown in FIG. 19A. The only changes are that a somewhat different arrangement of reference target array 130 with respect to support wire 140 is used, and that the distance of the reference target array from the camera is controlled by using support wires with different permanently bent sections, just as in the second embodiment (FIG. 16).

If support wires 140 of different cross-sectional size are to be used, a known clamping arrangement, such as a set screw oriented parallel to pins 172, can be added to secure the wire to support body 160*a*. If wire 140 is of circular cross-section, then target array 130 can be oriented with respect to the motion of the borescope to best match a given measurement situation. The shape of support wire 140 at bent section 142 can be varied to provide some capability to change the relative locations of target array 130 and borescope insertion tube 402. If needed, a temporary handle, similar to that shown in FIG. 16, can be added to the proximal end of support wire 140 after it is installed in support body 160*a*.

Just as in the first two embodiments, one can eliminate the need for borescope support body 160*a* if one is able to capture the images in a short exposure time.

5. Additional Implementations for Inserting and Holding the Reference Target Array Clearly, one could use the target array holding methods discussed in connection with the second and third embodiments with the flexible endoscope shown in the first embodiment. However, the broader applicability of the flexible endoscope leads to a desire for additional methods of placing a reference target array in the inspection scene.

The examples in this section depict the use of planar reference target arrays, but they can be used to hold three-dimensional target arrays just as well.

In the art of industrial endoscopy, it is known to use a variety of endoscope guide tubes to guide flexible endoscopes along specific paths inside an enclosure to positions where remote objects of interest can be viewed advantageously. Such guide tubes come in three varieties: rigid, semi-rigid, and flexible.

A rigid guide tube is essentially a pipe bent into a specific shape and of a specific length that is appropriate for a particular application. The guide tube is mounted to the inspection port at the proximal end to form a fixed insertion path for the inspection endoscope. In some cases a rigid guide tube includes provision for rotating the tube about its axis at the proximal end, so that the endoscope can be guided to a number of specific inspection sites from a single inspection port with a single guide tube.

Semi-rigid guide tubes are pipes made of a flexible material that has a memory of its shape. These guide tubes are installed to the operating position by use of a rigid insert, which straightens the tube for insertion through the inspection port. Once the guide tube is inserted, the rigid insert is removed, allowing the guide tube to revert to its original shape, which then allows guiding of the tip of the endoscope to the correct position for inspection of the object of interest.

A flexible guide tube contains one or more articulating (bending) mechanisms along its length. The articulating mechanism allows the operator to bend the tube into various shapes from a control mechanism located at the proximal end of the tube. The articulation ability of a flexible guide tube is similar to the articulation ability of an articulated flexible endoscope, but the guide tube itself contains no optics. The flexible guide tube allows for a much wider range of application than do the rigid or semi-rigid types.

FIG. 21 shows the distal end of a rigid or semi-rigid guide tube 240 into which a flexible endoscope 100 has been inserted. A measurement reference target array 130 mounted on a support wire 140 is attached near the distal tip of guide tube 240 with a target array attachment 242. The tip of flexible endoscope 100 is protruding from the distal end of guide tube 240 so that an object 120 can be inspected. Target array attachment 242 can be a known clamp or other arrangement that allows wire 140 and array 130 to be mounted at various positions and orientations near the tip of guide tube 240.

The apparatus shown in FIG. 21 enables one to use the measurement system of the first embodiment to make three-dimensional measurements of object 120 as desired. In FIG. 21, the preferred endoscope bending motion for carrying out the measurement is more or less perpendicular to the plane of the Figure, because then there is no chance of contact between support wire 140 and endoscope 100.

FIG. 21A shows a variant of the target array support in which support wire 140 is covered over most of its length by a dissipative polymer coating 141. Coating 141 acts to damp vibrations of array 130, and thus increases the stability of the support provided by wire 140. Such a coating can be used on any of the implementations already shown or those to be shown subsequently. Such dissipative coatings are available, for instance, from the Sorbothane company of Kent, Ohio.

The range of locations and orientations of target array 130 with respect to guide tube 240 is restricted only by the necessity of feeding the target array assembly and the guide tube through the (possibly, series of) inspection ports provided for access to the interior of the chamber which encloses object 120.

Figure 22A:
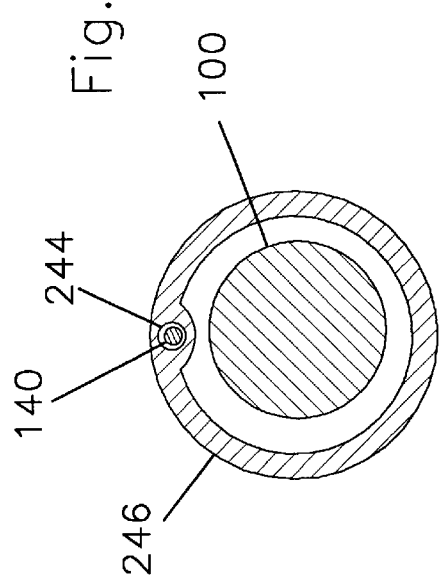
FIG. 22A is a cross-section of the apparatus at the position denoted by 22A–22A in FIG. 22.
Figure 22:
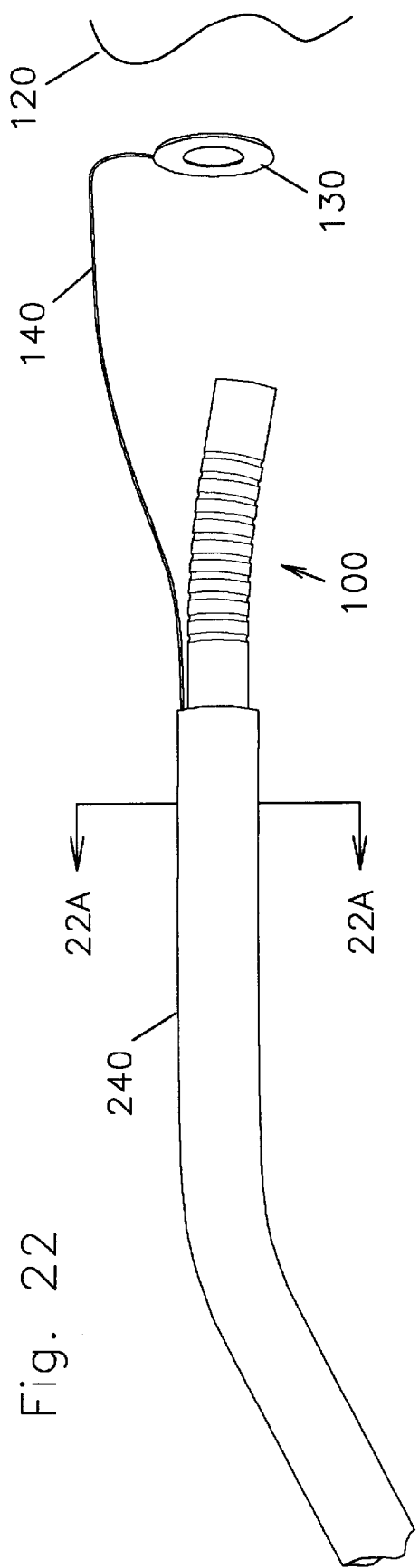
FIG. 22 depicts a measurement apparatus comprised of a rigid or semi-rigid guide tube with a reference target array mounted to a wire which is threaded through an accessory lumen in the wall of the guide tube.

In the art it is also known to use a guide tube with an auxiliary lumen in its wall for inserting accessories, such as a snare, into the inspection region. Such a lumen is often called a "working channel". One then makes use of the accessory while viewing the process through an endoscope. FIG. 22 is a perspective view showing a reference target array 130 mounted to a flexible support wire 140, where the support wire has been threaded through a lumen 244 in wall 246 of guide tube 240. FIG. 22A is a cross-sectional view taken generally at the position denoted by the lines 22A—22A in FIG. 22.

Target array 130 may be either permanently attached to support wire 140, or it may be removable, in which case there may be multiple ones of array 130 to be used for different applications. The target array example shown in FIG. 22 has an opening, so that points of interest can be viewed through the array, and reference target points can therefore surround the region of interest.

In many cases, an arrangement of reference target points surrounding the points of interest on the object will be ideal. However, there are then limits to the dimensions that can be measured and to the distance between the target array and the object which can be used to make a feasible measurement. Of course, it is not that a measurement cannot be made at all when these limits are exceeded, it is just that one loses the advantage of having the reference points surrounding the dimension of interest.

In fact it is possible to make a rigid, planar target array on a glass substrate, so that the area of interest may be viewed through the target array. Viewing through the substrate will cause very little error as long as either all of the object points or none of the object points to be measured are viewed through the transparent substrate at both viewing positions of the camera. In order to cause appreciable error, the glass substrate would have to be very thick. Of course, any other rigid, transparent material could be used instead of glass for this purpose.

To use the apparatus of FIG. 22, support wire 140 is inserted into the lumen from the distal end of the guide tube if target array 130 is permanently affixed to wire 140, otherwise, it may be inserted from either end. Wire 140 is then attached to a suitable clamping mechanism (not shown) at the proximal end of the guide tube. Guide tube 240, with attached target array 130, is then inserted into the inspection port and manipulated into position. Then flexible endoscope 100 is inserted through the guide tube and manipulated to view the object of interest. Finally, the clamp at the proximal end of the guide tube is loosened and target array support wire 140 is manipulated to position the target array with respect to object of interest 120 as required, then the clamp is retightened. At this point a three-dimensional measurement as described above can be performed.

Of course, there is a tradeoff between the flexibility of support wire 140, the distance between object 120 and the distal tip of guide tube 240, and the position stability of target array 130. Rather than a solid wire, one can use tubing to form support member 140 to increase the stiffness to weight ratio if this is important for the application.

Figure 23:
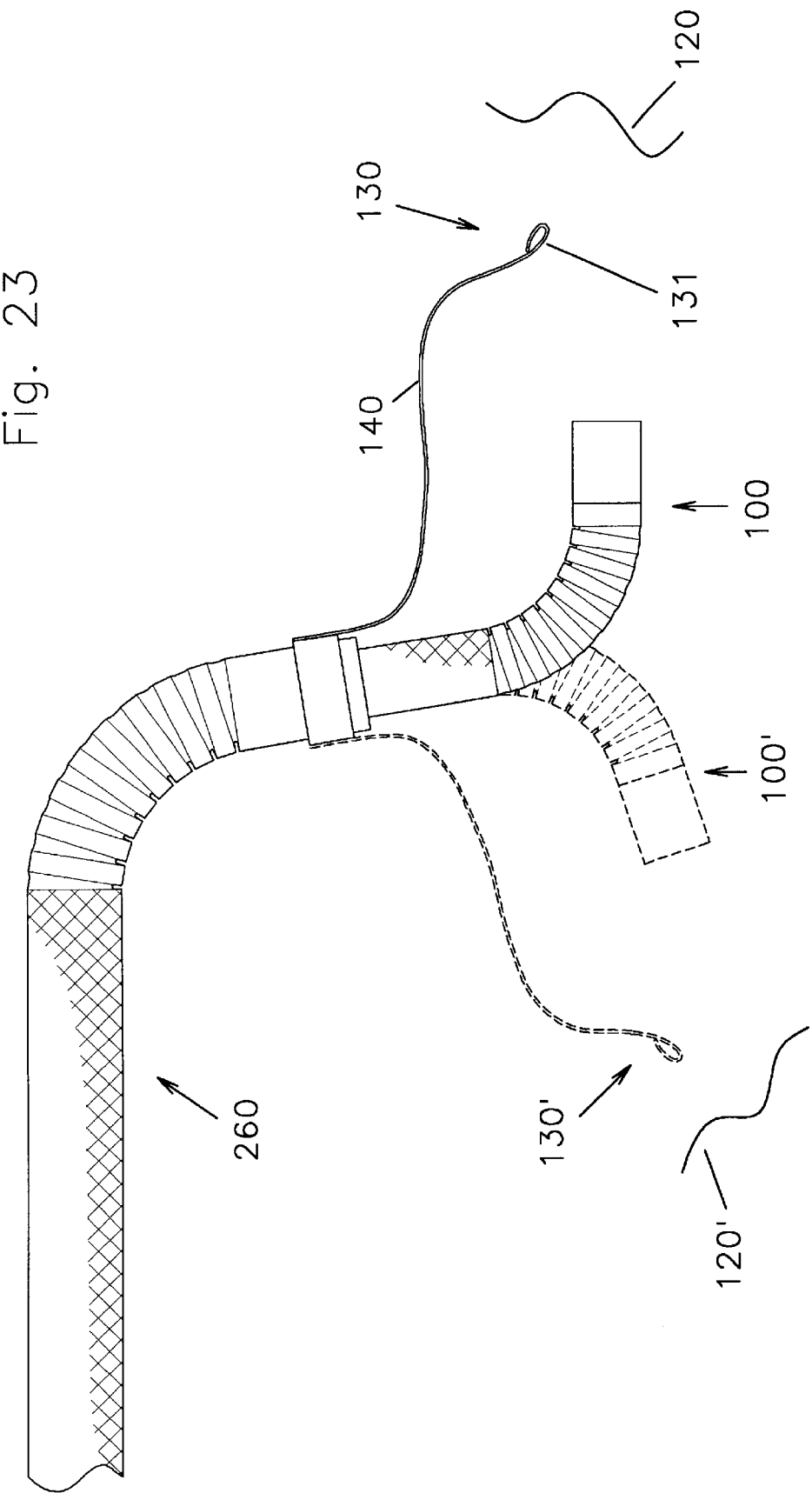
FIG. 23 shows two different measurements being made with a target array mounted to a flexible endoscope guide tube.

FIG. 23 shows a flexible guide tube 260 with a support wire 140 and a target array 130 mounted to its distal end in a manner similar to that shown for the apparatus of FIG. 21. The tip of a flexible endoscope 100 has been advanced beyond the tip of flexible guide tube 260 and articulated in order to view an object of interest 120.

With this apparatus, since the guide tube is flexible, the target array and the endoscope tip can be moved about inside the enclosure together to enable measurements of various objects of interest. During use, the target array is positioned near the object by the articulation of the guide tube, and then the endoscope is manipulated to acquire an appropriate pair of views of the region of interest. As an example, an object 120' can be inspected with the target array at a position 130' and the endoscope at the position denoted by 100' simply by rotating guide tube 260 by approximately 180 degrees about its axis and then reversing the direction of its articulation.

In the example of FIG. 23 target array 130 is comprises a tip loop 131 of the same wire which forms support 140. Tip loop 131 can be formed or machined to have a planar surface (not shown) which is marked with reference target points (not shown) for ease of characterization. Thus, the target array shown in FIG. 23 obscures only a small portion of object 120 while providing a suitable array of reference targets for making measurements.

In FIG. 24 is shown a very versatile method of positioning the reference target array. The apparatus there is shown being used with a flexible measurement endoscope 100, but it can be used with any of the three embodiments of the measurement system.

In FIG. 24, a reference target array positioning endoscope 270 has mounted to it a support wire 140 and a reference target array 130. Support wire 140 and array 130 are such that array 130 is contained within field of view 272 of positioning endoscope 270. Positioning endoscope 270 is then manipulated so that array 130 is located at a suitable position with respect to a region of interest 122 on object 120. For this purpose, the operator views through endoscope 270, and endoscope 270 may itself make use of a guide tube.

Measuring endoscope 100 is then manipulated into position to obtain two suitable views of both region of interest 122 and reference target array 130 and measurements proceed as previously explained.

Clearly, support wire 140 can be attached near the distal end of positioning endoscope 270 in the same manner as it was attached to the guide tube of FIG. 23, or it can be inserted through an operating lumen in endoscope 270, if that scope contains such a feature.

One might at first think that use of a second endoscope to position a target array is so expensive that it would have little application; however, many users have available older, lower quality endoscopes that are not being used for any other purpose. For these users, the system shown in FIG. 24 enables them to make good use of this older equipment, as well as providing a powerful and effective way of positioning an array of measurement reference targets into a scene. If the application allows, one could also use a rigid borescope to hold and position the reference target array instead of the flexible endoscope shown.

There are additional important and non-obvious advantages to the system of FIG. 24. One advantage is that the illumination provided by array positioning endoscope 270 strikes object 120 at an oblique angle with respect to the view of measuring endoscope 100. Under many circumstances this oblique illumination will serve to make features of interest on object 120 dramatically more visible than they are with the direct illumination provided by measuring scope 100. In other circumstances, just the fact that there is more illumination available will aid in making an accurate measurement. In still other circumstances, the ability to tailor the illumination by adjusting the relative illuminations provided by the two scopes will be found helpful. Some applications will be aided by the fact that the illumination provided by positioning endoscope 270 is fixed as compared to the case when measuring scope 100 provides the illumination.

A second advantage of this system is that one could make the measurement without moving either endoscope between views, if one uses the images provided from both scopes for the measurement. That is, one view is provided by endoscope 100 and the other view is provided by endoscope 270. In this case, endoscope 270 would have to be calibrated in the same manner as endoscope 100, but this calibration could be accomplished by locating a suitable number of extra reference target points as was discussed in Section 2D, above. Specifically, one needs to use the number of reference points shown in the third row of Table I, even if the same reference points were used in both images.

If one has two endoscopes, and wishes to make the measurement by using one image from each scope, there is no need for the reference target array to be mounted to one of the scopes as shown in FIG. 24; one can use any of the other methods of inserting and holding a reference target array that are taught here.

One could use positioning endoscope 270 of FIG. 24 to place a standard dimensional scale against an object of interest. However, the straight edge of a standard dimensional scale cannot, in general, be placed against the points of interest if the surface of the object is convex or concave, as is often the case. In addition, it will usually not be possible to manipulate the measurement endoscope to view perpendicular to the scale. Therefore there will still be errors (parallax errors) made in such a measurement unless the scale indicia exactly touch the points of interest. My new system of measurement is superior, even in the case where a second endoscope can be used to position a scale, because it does not depend on there being any particular relationship between the points on the object being measured and the reference target points.

6. Additional Embodiments of the Reference Target Array

A. Arrays Based on Plane Substrates

To this point all of the exemplary reference target arrays shown have been mounted to a positioning wire or rod. While this approach does give some ability to manipulate the position and orientation of the array with respect to the object of interest and with respect to the inspection endoscope, a more extensive capability is sometimes required.

In general, the requirements for the reference target array are that the array must fit through an available inspection port, and that it must be dimensionally stable. It has already been mentioned that for ease in characterization of the array during manufacture, it is preferred that the active surface of the array be flat, but that puts a requirement on the orientation of the plane of the array during the measurement. If one wishes to eliminate this requirement, then one must use a three-dimensional array.

For applications where it is desirable to be able to manipulate the array orientation with respect to the support, FIG. 25 shows one approach. In FIG. 25 a target array 130 is mounted to a support rod 140 with an adjustable ball joint mechanism. Target array 130 has a ball stem 147 that is clamped in jaw 148 through the action of clamping nut 146. This assembly is adjusted before insertion into the inspection port. It allows more advantageous target array positioning over a wider range of situations than do the previously shown support wire implementations. While some adjustment of the target array orientation can be obtained by bending a support wire, that approach is limited in adjustability and controllability.

The flat target array 130 shown in FIG. 25 can be made three dimensional simply by adding one or more short posts to the surface, mounted perpendicular to the surface, with at least one target point marked on the top surface of each of the posts. Such a post is indicated by the broken line circle with reference number 149. The length of these posts are such that the cross-section of the array perpendicular to the view shown in FIG. 25 is no greater than the cross-section shown in the plane of the Figure.

Figure 26:
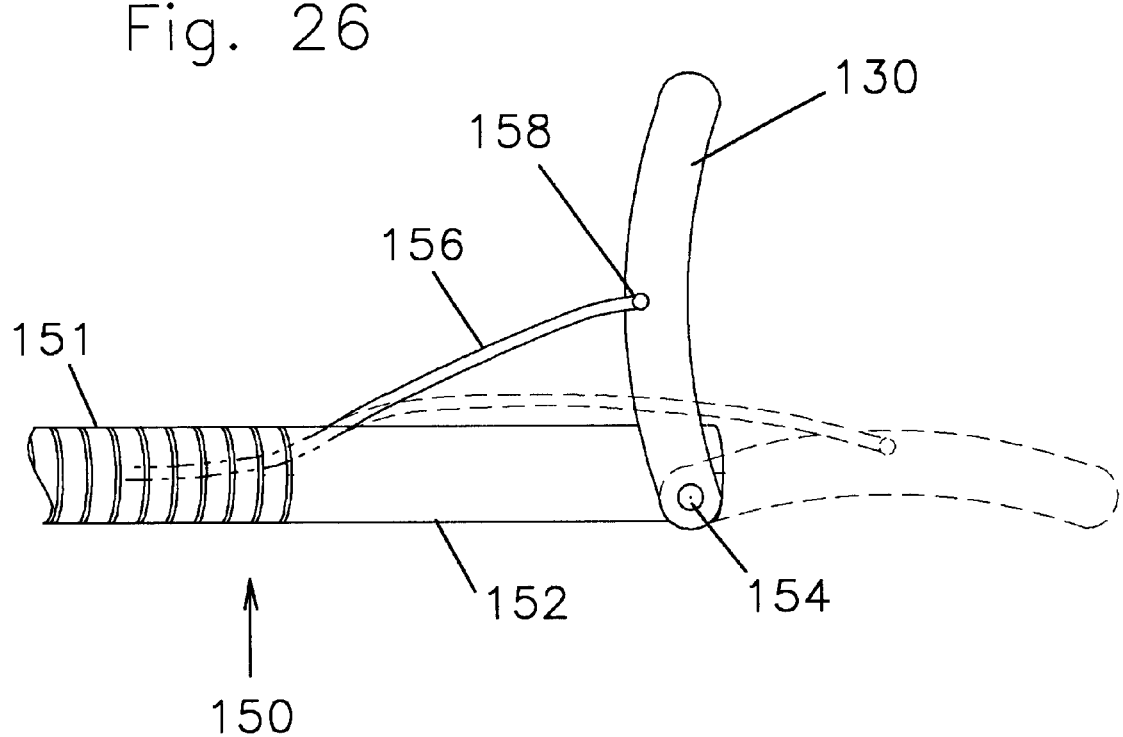
FIG. 26 shows a rigid target array which can take various orientations with respect to its support, and where the orientation is variable in-situ.

Another example of a reference target array with an adjustable orientation is shown in FIG. 26. This apparatus is especially applicable for use through a lumen in a flexible or semi-flexible guide tube (FIG. 22), and for mode 2 measurements made between widely separated points. In FIG. 26 a flexible or semi-flexible reference target support member 150 is composed over the vast majority of its length of a sheath 151 made up of a tightly coiled wire. At the distal end of sheath 151 is mounted an end cap 152. End cap 152 supports a hinge 154 to which is mounted a target array 130. End cap 152 also has a wire operating aperture (not shown) through which an operating wire 156 passes. Operating wire 156 is attached to target array 130 at an operating hinge 158. Sheath 151 and operating wire 156 extend proximally back to a user position (not shown) at some distant point from the inspection area. The relative orientation of target array 130 with respect to end cap 152 is then manipulated by a user from the proximal end of support member 150 by pushing or pulling on operating wire 156.

For insertion through inspection ports, array 130 is moved to a position substantially aligned with end cap 152 by moving operating wire 156 distally with respect to sheath 151. This position is shown by the broken lines in FIG. 26. Once it is inserted into the enclosure, array 130 is moved to the desired operating position by moving operating wire 156 proximally with respect to sheath 151. Support member 150 is manipulated as a whole to position array 130 with respect to an object of interest (not shown). Thus, the orientation of this reference target array can be changed as required during use, without requiring one to withdraw and reinsert the array through the inspection port.

It should be evident that the flat side of array 130 could be oriented perpendicular or at some other angle with respect to the plane of FIG. 26 if that better matches the application. Also, support member 150 could be composed of a rigid tube, rather than the flexible or semi-flexible tube shown, if the application does not require passing support member through a lumen which is curved along its length. Array 130 of FIG. 26 can be made three-dimensional by adding one or more posts as was discussed above with regard to the apparatus of FIG. 25.

To this point, the exemplary target arrays shown have been marked on rigid substrates. The advantage of a rigid target array substrate is that the relative locations of the target points are easily made fixed and stable. The disadvantage of a rigid substrate is that the substrate must pass through whatever inspection openings are available between the proximal position of the user and the distal object of interest. The apparatus shown in FIG. 26 eases this problem somewhat, but it still must have a small cross-section when configured for passing through inspection ports. While rigid substrates are simple and straightforward, it is not necessary that the reference target array always be marked on a rigid substrate.

Figure 27:
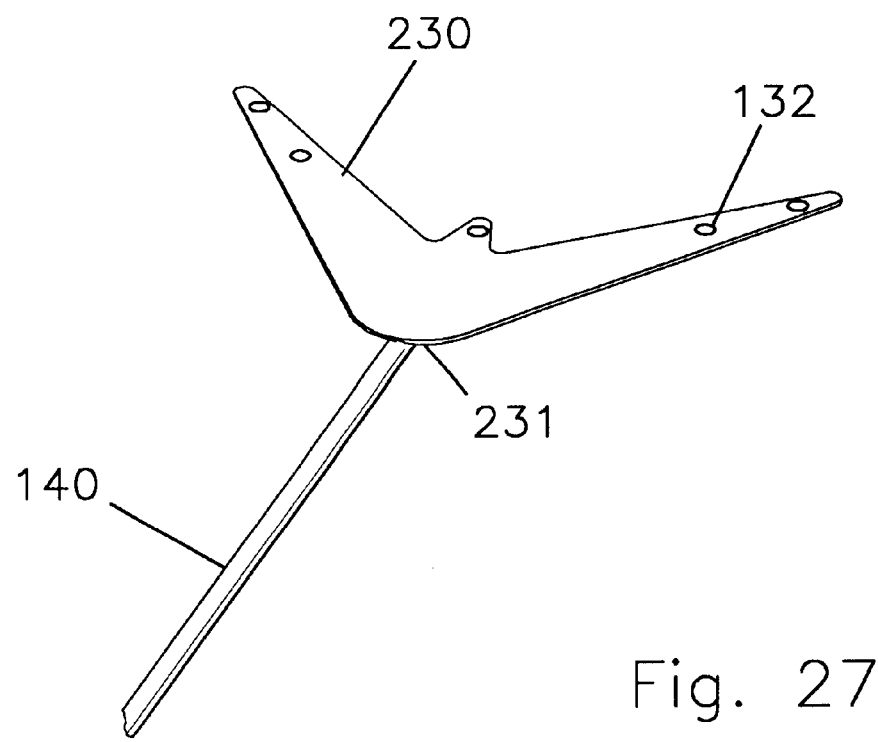
FIG. 27 is a perspective view of a flexible target array which can be bent to pass through an inspection port, and which will return to its original shape.

FIG. 27 is a perspective view of a semi-flexible reference target array 230 which is mounted to a support wire 140. Semi-flexible target array 230 has a plurality of target points 132 marked on its surfaces. Array 230 is fabricated from a flat sheet of flexible and resilient material such as spring steel or beryllium copper alloy. It is attached to support wire 140 by a conventional process such as soldering, welding, or riveting. The rear end of array 230 near support wire 140 is curved to form a heel 231. It is intended that the overall width of semi-flexible target array 230 be larger than can be passed directly through the available inspection ports.

Figure 28:
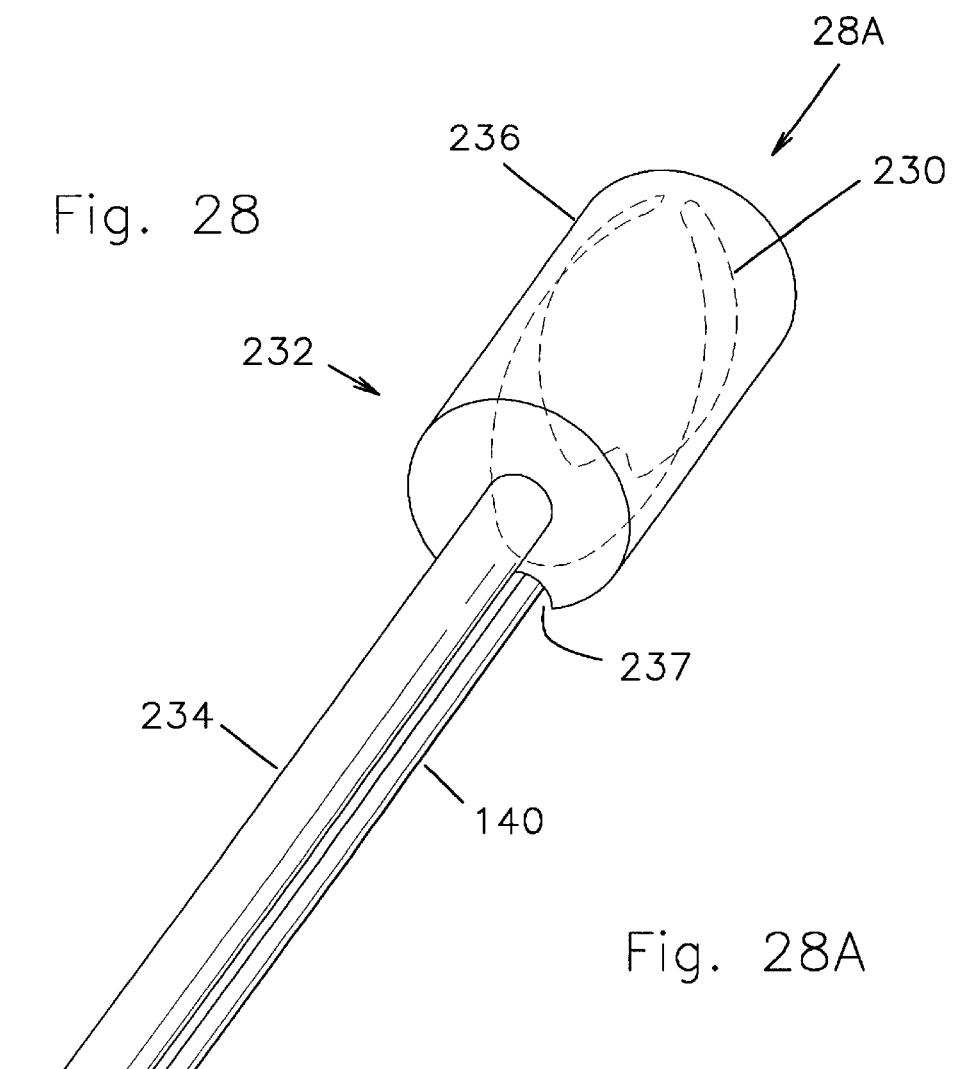
FIG. 28 shows the flexible array of FIG. 27 installed into an insertion tool in preparation for passing the array through an inspection port.
Figure 28A:
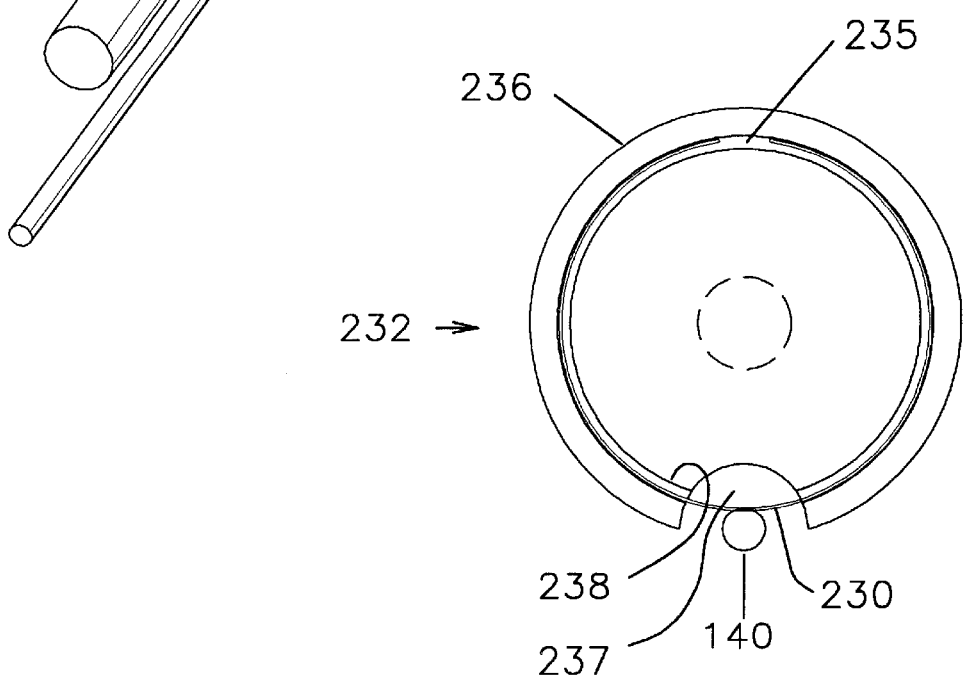
FIG. 28A is a front elevation view of the insertion tool with the installed reference target array.

In FIG. 28, array 230 is shown installed into an array insertion tool 232. Insertion tool 232 comprises a handle 234 and a tool enclosure 236. FIG. 28A depicts a front elevation view of the assembly of FIG. 28, along the direction denoted by the arrow marked 28A in FIG. 28.

In FIG. 28A one sees that an inner cylinder 238 is used to guide array 230 as it is bent to fit into an annular slot 235 between tool enclosure 236 and inner cylinder 238. Both tool enclosure 236 and inner cylinder 238 contain a cylindrical slot 237, which allows passage of support wire 140.

In use, cylindrical slot 237 of insertion tool 232 is placed over support wire 140 and then handle 234 is moved forwards while support wire 140 is moved backwards to introduce heel 231 (FIG. 27) of array 230 into annular slot 235. Once introduced, sufficient force is supplied to bend array 230 to force it to take the shape of annular slot 235. Once array 230 is fully enclosed within tool enclosure 236, the insertion tool is inserted through the inspection port (not shown). Then support wire 140 is pushed forward, freeing array 230 from tool 232 and allowing it to expand to its original configuration as shown in FIG. 27. Insertion tool 232 is then withdrawn from the inspection port. To remove the target array from the inspection enclosure, insertion tool 232 is reintroduced to the inspection port, and the process of installing the array into the tool is repeated. Finally, the tool and the target array are together withdrawn from the enclosure through the inspection port.

Figure 29:
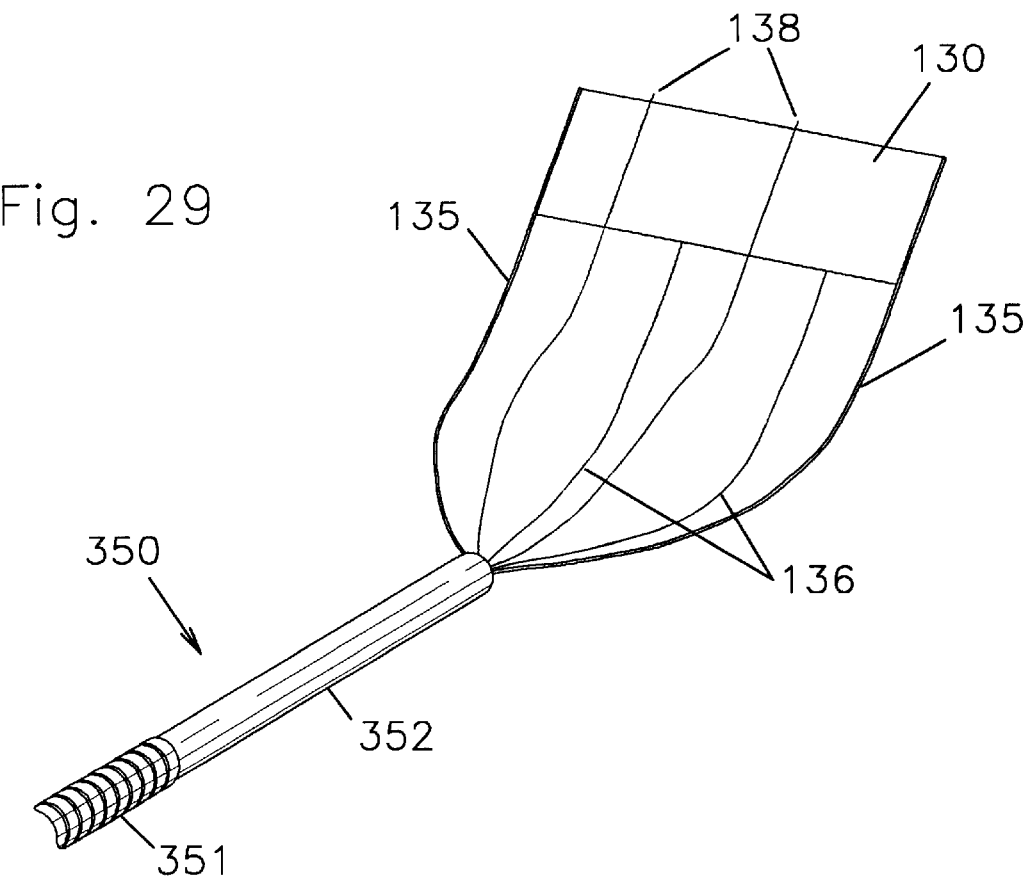
FIG. 29 shows a perspective view of a flexible reference target array in its expanded configuration.
Figure 31:
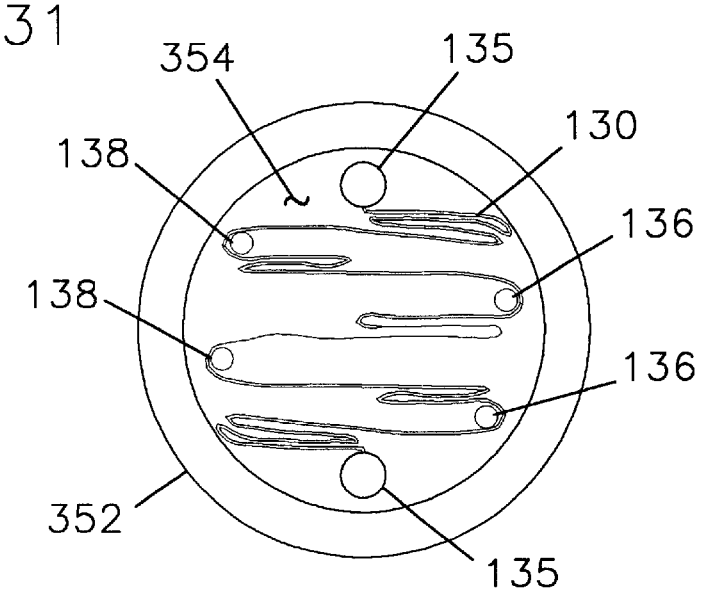
FIG. 31 is a cross-sectional end view of the collapsed configuration the flexible reference target array of FIGS. 29 and 30, generally as would be seen at the position indicated by 31'—31' in FIG. 30A.

Another implementation of a reference target array which can be collapsed for insertion through a port, and then expanded when inside an enclosure, is depicted in FIGS. 29 through 31. FIG. 29 shows a perspective view of a flexible reference target array 130 in its expanded configuration. FIGS. 30A and 30B show respectively top and side views of the same configuration, where FIG. 30B is shown partially in cross-section generally as indicated by the arrow marked 30B in FIG. 30A. FIG. 31 shows an end view cross-section of the collapsed configuration of the array, generally as would be seen at the position indicated by 31'–31' in FIG. 30A.

In FIG. 29 flexible target array 130 is supported by two support wires 135 located at either end. Flexible array 130 is made of a woven material such as cloth, or a material with a great deal of inherent flexibility, such as a polymer film. Support wires 135 exert sufficient spring tension on array 130 to pull it taut in the expanded configuration shown. Support wires 135 are in turn supported by a rigid end section 352 of a flexible target array support assembly 350. Rigid end section 352 is mounted to a flexible sheath 351, which extends proximally to an operating mechanism (not shown) at a user's position (not shown).

As shown in FIG. 30B, support wires 135 are mounted at their proximal ends in a tip plunger 353. Plunger 353 slides in an operating bore 355 in rigid end section 352. The position of plunger 353 is controlled by an operating wire 356. Operating wire 356 extends proximally through flexible sheath 351 back to the user's position (not shown).

Flexible sheath 351 is preferably formed from a helically wound wire. Operating wire 356 may be either a solid wire or a woven or wound cable, depending on the application. Clearly, when operating wire 356 is moved in a proximal direction with respect to sheath 351 at the user's position (not shown), tip plunger 353 will be drawn further into rigid end section 352 as compared to the position shown in FIG. 30B. Support wires 135 will be drawn in with tip plunger 353, and will be bent to fit into a target array storage compartment 354 at the distal tip of rigid end section 352. As support wires 135 are bent in this process, flexible target array 130 will begin to collapse. As operating wire 356 is moved further in the proximal direction with respect to sheath 351, support wires 135 will be drawn into operating bore 355, and target array 130 will enter storage compartment 354. Thus there can be a large ratio between the dimension of the expanded target array and the diameter of the inspection port through which it can pass.

Also shown in FIGS. 29 and 30 are a pair of lower guide wires 136 and a pair of upper guide wires 138. These wires are less stiff than are support wires 135, and are bent into a different shape as shown at bends 137 and 139 in FIG. 30B. Because of the different curve of the guide wires, as the target assembly is drawn into rigid end section 352, guide wires 136 and 138 come into contact with the collapsing flexible target array 130 and cause it to become folded in a predetermined manner. Thus, the purpose of guide wires 136 and 138 is to ensure that flexible target array can be drawn into storage compartment 354 without hanging up at the distal end of rigid end section 352. The cross-section of FIG. 31 depicts a typical configuration of the collapsed flexible reference array as stored in storage compartment 354. Note that the permanent shape of support wires 136 and 138 is such that in the expanded configuration, these wires do not contact array 130, thus ensuring that the three dimensional surface contour of array 130 is not distorted by their presence.

Clearly, support wires 135 can be formed with various degrees of curvature as seen in the side view of FIG. 30B. For instance support wires 135 could be straight in that view.

Thus, the orientation of the deployed reference target array with respect to support assembly 350 can be chosen over a wide range to best fit the application. For each such application, guide wires 136 and 138 will also be bent accordingly.

Just as with the reference target array of FIG. 26, the target array assembly of FIGS. 29 through 31 can be inserted through a lumen in a guide tube or an auxiliary endoscope in its collapsed configuration. If rigid end section 352 is not too long, it can be inserted from the proximal end after the guide tube or endoscope is in position for inspection of the remote object of interest, rather than having to be inserted from the distal end before the guide tube or endoscope is inserted through the inspection port.

It is also possible to make sheath 351 of support assembly 350 rigid—then this reference target array could be used anywhere a rigid target array support rod could be used. The sheath could also be made quasi-rigid, so that the distal end of the sheath could be bent and re-bent by the user to suit the application, and yet would maintain its shape under normal use.

In the exemplary apparatus shown here, the fully deployed and fully collapsed positions are determined by mechanical stops (not shown) at the proximal end which determine the extreme positions of control wire 356 with respect to sheath 351. It is also possible to provide such stops at the distal end of the apparatus.

Array 130 can be formed of a transparent material, or it could be fabricated with one or more openings, so that reference target points can be conveniently arranged surrounding the object points of interest.

In U.S. Pat. No. 4,721,098, Watanabe discloses an expandable measurement scale apparatus that is comprised of 3 segments of wire attached end to end. In its collapsed configuration the connection between one pair of segments is bent to 180 degrees so that two of the wire segments lie adjacent to and parallel to the third segment, thus forming a linear body with a small cross-section. In its expanded configuration the connections between each pair of segments is bent at a moderate angle so that the three segments together form a triangular body. It is evident that if appropriate reference target marks were placed on at least two of the wire segments, one could use the resulting structure as a reference target array for the purposes of the instant invention.

B. Fully Three-Dimensional Arrays

In photogrammetry, three-dimensional reference target arrays, called control frames, are often implemented as a space frame made up of spheres spaced apart by straight rods in a usually cubic configuration. For the purposes of endoscopic measurements we want alternate solutions for three reasons. First, the small size of the required reference target array means that a space frame would be difficult to fabricate accurately. Secondly, such a tiny space frame would be fragile, which is undesirable for any instrument which is expected to make accurate measurements over an extended time. Finally, a tiny three-dimensional space frame requires an expensive three-dimensional coordinate measurement system for its initial characterization.

Most of the examples shown below alleviate this latter problem by making it possible to characterize the array using a relatively inexpensive two-dimensional coordinate measurement system, such as a toolmaker's microscope.

Figure 32:
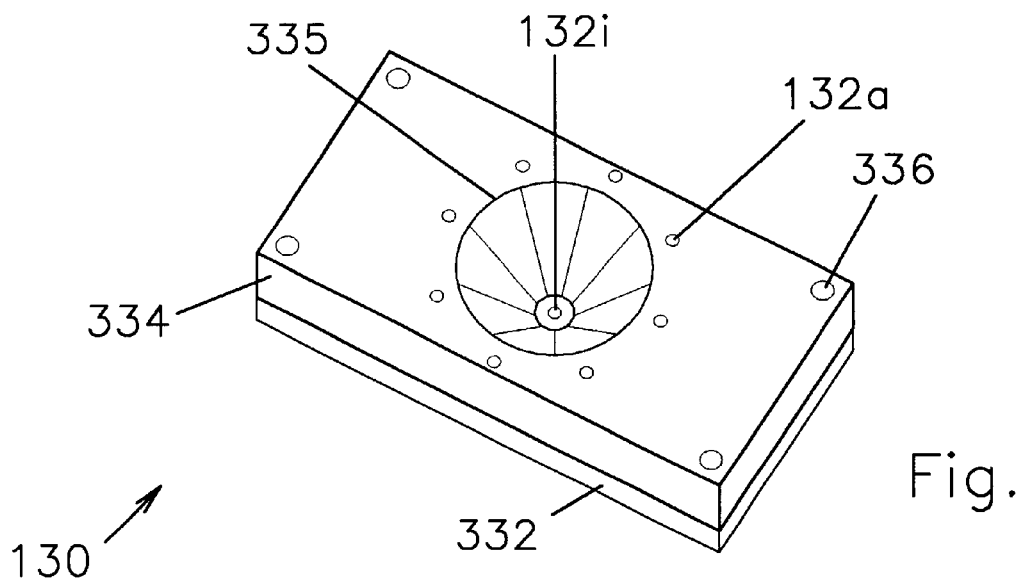
FIG. 32 shows a first embodiment of a three-dimensional reference target array which can be characterized using only two-dimensional metrology.

A first example of a three-dimensional reference target array is shown in FIG. 32. In this device, three-dimensional target array 130 is comprised of a back plate 332 and a cover plate 334. These plates are held in precise in-plane registration through a multiplicity of alignment pins 336. This array can be directly substituted for many of the planar target arrays shown in various of the embodiments discussed above.

An aperture 335 is cut through cover plate 334 so that a portion of back plate 332 can be viewed through it. At least one reference target point, 132$i$, has been marked on back plate 332 and is visible through aperture 335. A multiplicity of additional reference target points, as shown for example by 132$a$, are marked on the front side of cover plate 334 surrounding aperture 335.

During characterization of this reference target array, one determines the position of target point(s) 132$i$ on the surface of back plate 332 with respect to the accurately reamed holes in the back plate which accept alignment pins 336. This requires only a two-dimensional coordinate measurement. Similarly, one also determines the positions of target points 132$a$, etc. on the front surface of cover plate 334 with respect to the alignment pin holes in cover plate 334. When one assembles cover plate 334 to back plate 332, one then has a known relationship between the positions of all of the reference target points to an accuracy determined by the perpendicularity and position tolerances of the holes provided for alignment pins 336 in cover plate 334 and the tolerance on the thickness of cover plate 334. Cover plate 334 is then fastened to back plate 332 by, for instance, screws or adhesive bonding into relief wells which are provided for this purpose, neither of which is shown in FIG. 32.

Aperture 335 is shown as a conical depression in FIG. 32, but it could be a simple cylindrical hole. The maximum viewing angle at which this reference target array can be used is determined by the ratio of the diameter of aperture 335 to the thickness of cover plate 334.

If aperture 335 has a larger diameter at the rear surface of cover plate 334 than is depicted in FIG. 32, there is room for additional reference points marked on back plate 332, and these additional points could be useful for making measurements of the highest possible precision. For "mode 2" measurements, one would use multiple ones of aperture 335 in cover plate 334; each of these apertures would then have an associated array of reference target points located both within and without the aperture.

Figure 33:
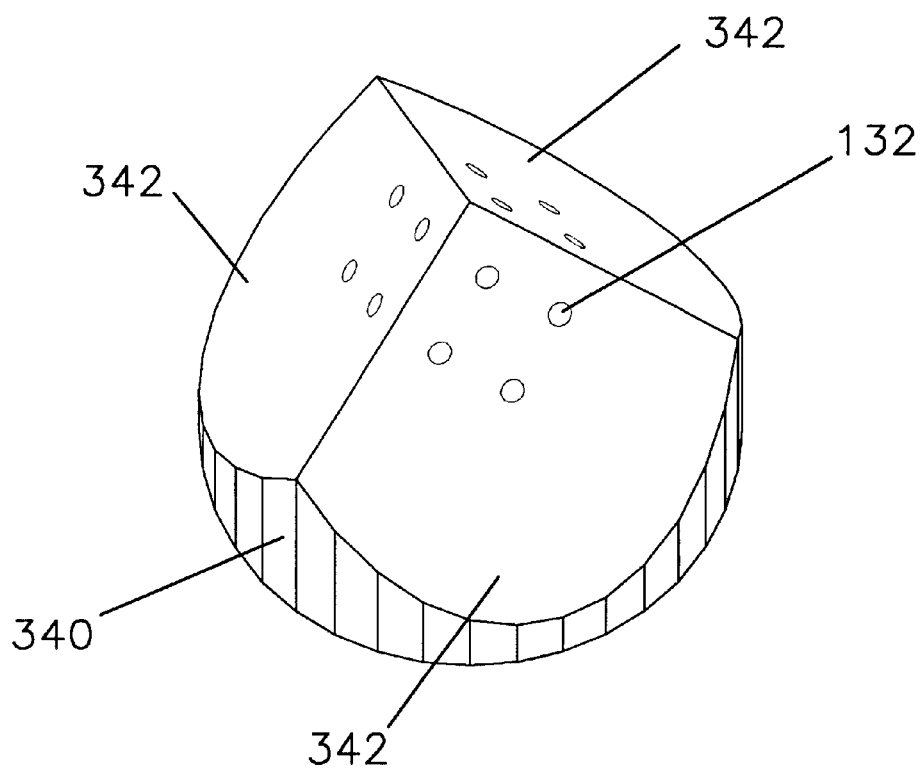
FIG. 33 shows a second embodiment of a three-dimensional reference target array which can be characterized using only two-dimensional metrology.

A second example of a three-dimensional reference target array is shown in FIG. 33. Here, a solid reference array body 340 has been fabricated to have three reference array face planes 342. The three planes 342 are fabricated at mutual right angles, that is, the surface formed by these three planes is the corner of a cubic solid. One can determine the three-dimensional relative positions of target points 132 marked on each of face planes 342 by performing only two-dimensional coordinate measurements on each of planes 342, using the edges where planes 342 come together as the coordinate axes. Such accurately fabricated three-dimensional corners are commonly used in the technology of mechanical metrology, and are available at moderate cost. Of course, a wire or one of the more elaborate array support structures described above can be attached to array body 340 to enable it to be positioned as required for a measurement.

Figure 34:
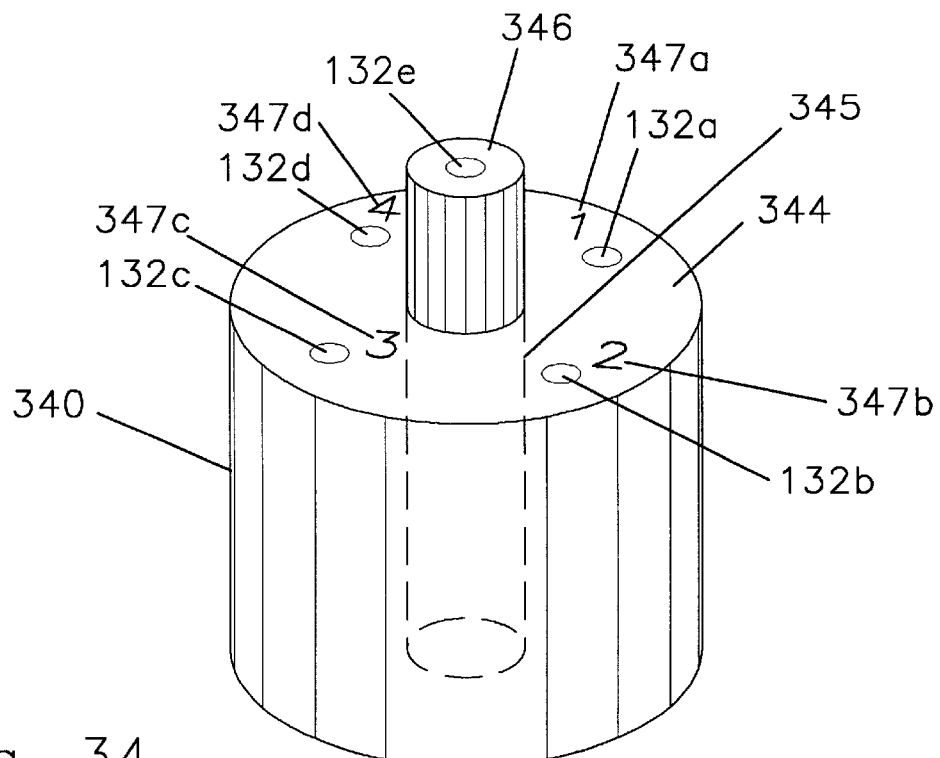
FIG. 34 shows a third embodiment of a three-dimensional reference target array which can be characterized using only two-dimensional (and one-dimensional) metrology.

A third example of a three-dimensional reference target array, and the one I prefer for general purpose use, is shown in FIG. 34. Here a reference array body 340 has been fabricated with an end plane 344. As shown, array body 340 is cylindrical, but that shape is not a necessary feature. Accurately perpendicular to end plane 344 has been reamed a precision center hole 345, shown by a broken line because it is hidden. The term "center hole" is used only for convenience; there is no requirement that this hole actually be located in the center of anything. This hole does, preferably, extend completely through the depth of array body 340 so that it is accessible at both ends.

Inserted into center hole 345 is a precision center pin 346. Marked on the outer end of pin 346 is a reference target denoted as 132e. Marked on end plane 344 are a multiplicity of reference target points which consists of at least three, and preferably, at least four target points. The four reference target points shown are denoted as 132a through 132d. Associated with each of the target points is a target index to unambiguously designate each point; these target indices are denoted as 347a through 347d respectively.

Reference array body 340 can be, for instance, machined from 0.25 inch diameter brass rod, and its length can be 0.19 inch. Center hole 345 can be reamed $0.0630_{-0.0000}^{+0.0002}$ inch diameter, which is a standard, commonly available, reamer size. Center pin 346 can then be fabricated from a standard dowel pin of 0.0627 inch diameter to provide a smooth sliding fit into center hole 345.

Before this reference target array is assembled, target points 132 are marked on end plane 344. Target points can be marked on end plane 344 using any convenient method, including having these targets marked onto a thin backing material (of uniform thickness) in a separate process and adhesively bonding that backing material onto end plane 344. Any such backing material must have a hole which leaves center hole 345 accessible; this is most easily achieved by punching the hole after the target points are marked on the backing material.

Target point 132e is also marked on the end of pin 346 before the reference array is assembled. In this process, some attention should be paid to locating the center of target point 132e at the center of pin 346; however, this need not be perfectly accurate. This can be conveniently done by putting pin 346 into a rotational fixture with accurate bearings (such as a lathe) and either marking the center by machining a small amount of material from the end of pin 346 to form a depression or series of rings that can be filled with paint, or by temporarily bonding a premarked piece of thin material to the end of pin 346 and adjusting its position so that the position of target 132e does not change as pin 346 is rotated. Once the position is correct, the bond can be made permanent, by allowing the temporary adhesive to harden, by using adhesive which can be hardened by applying heat or ultraviolet light, or by applying additional adhesive around the edge of the thin material on which target point 132e has been marked.

Once the target points are marked, the array is assembled by sliding pin 346 into hole 345. Pin 346 is first slid all the way in until the plane of target 132e is close to end plane 344 (that is, to the plane of targets 132a, 132b, etc.). If necessary, a temporary adhesive, such as rubber cement, is used at the rear end of hole 345 to insure that pin 346 remains at this position through the next step of the process.

The array is then partially characterized by determining the relative positions of all of the target points in a two-dimensional coordinate system and these data are recorded.

Pin 346 is then pushed partially out of hole 345 from the rear as is shown in FIG. 34. For instance pin 346 can be raised approximately 0.08 inches. In general there will be little tendency of pin 346 to rotate during this process, but if it does rotate, the fact that target 132e is located at the center of pin 346 guarantees that any rotation does not cause an error. Once pin 346 is advanced a suitable amount, a permanent adhesive, such as epoxy, is injected into the rear opening of hole 345 to fix pin 346 in place with respect to reference array body 340.

Finally, after the permanent adhesive has set, the projection of pin 346 with respect to the plane of the targets 132a, 132b, etc. is measured with a micrometer. If a standard anvil micrometer is to be used for this step, it is preferred that the rear end of reference array body 340 be machined accurately parallel to end plane 344.

The location of target point 132e with respect to the other targets is then considered to be the two dimensional location determined in the first partial characterization, with a third coordinate, perpendicular to the other two, given by the distance determined with the micrometer.

The reason that four points are preferred on end plane 344 is that there are then guaranteed to be at least three of them visible, even if one point happens to be hidden behind pin 346 in the view seen by the camera.

This array can be further improved by making it lighter in weight, either by making it out of a light metal alloy such as magnesium or beryllium, or by removing unneeded material from array body 340. The lighter weight will make the array more stable when it is supported by a support wire, such as those shown in FIGS. 1, 16, and 21.

Figure 35:
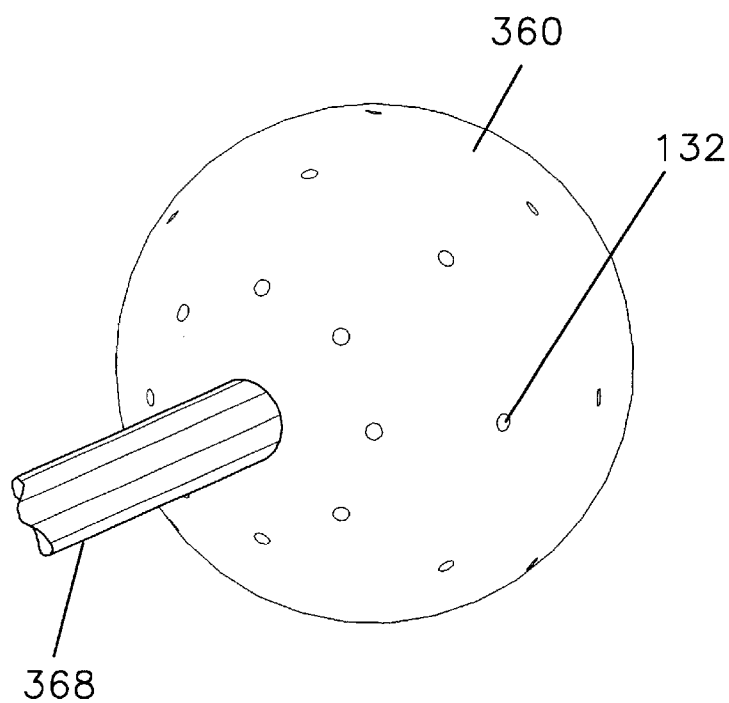
FIG. 35 depicts a three-dimensional reference target array that requires three-dimensional metrology in order to characterize.

A fourth example of a three-dimensional reference target array is shown in FIGS. 35 and 36. FIG. 35 shows a fragmentary perspective view of a reference target array which has a multiplicity of target points marked on the outer surface of a convex shell 360. A typical target point is denoted by reference numeral 132. In the particular configuration depicted, shell 360 is substantially spherical, but this is not a requirement. In use, the array of reference targets is supported by a shell support 368, only a portion of which is shown.

Figure 36A:
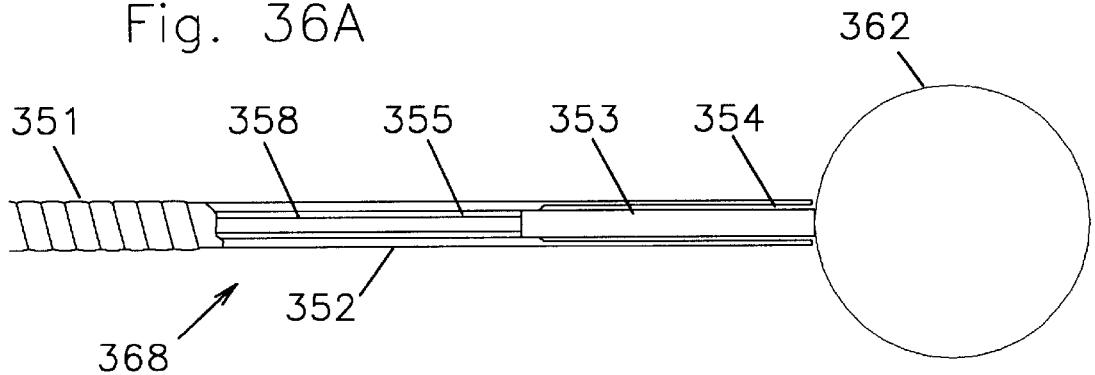
Figure 36B:
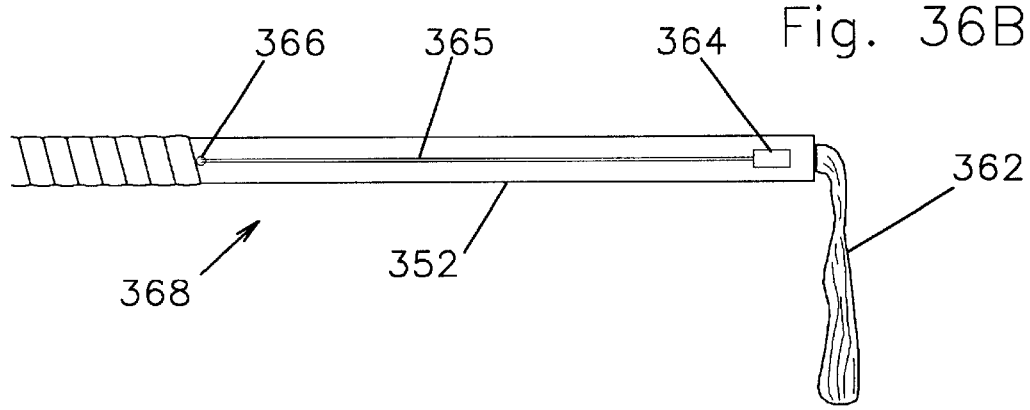
FIG. 36B is an external view that shows the bladder in its deflated state.

FIG. 36 shows further details of a specific implementation of the type of reference array introduced in FIG. 35. In FIG. 36 the convex shell is implemented as an inflatable bladder 362; bladder 362 is shown inflated in FIG. 36A and deflated in FIG. 36B.

Similarly to the flexible target array discussed above in conjunction with FIG. 30B, inflatable bladder 362 is supported by a shell support structure 368 which is comprised of a rigid end section 352 mounted to a flexible sheath 351, which extends proximally to an operating mechanism (not shown) at a user's position (not shown).

As shown in FIG. 36A, bladder 362 is mounted to a tip plunger 353. Plunger 353 slides in an operating bore 355 in rigid end section 352. The position of plunger 353 is controlled by a flexible operating tube 358. Operating tube 358 extends proximally through flexible sheath 351 back to the user's position (not shown). Operating tube 358 and tip plunger 353 are both hollow, and bladder 362 is attached to tip plunger 353 so that the hollow core of tip plunger 353 is open to the inside of bladder 362. Thus, when gas under pressure is introduced to operating tube 358 at the proximal end of the apparatus, this gas will flow into the bladder to inflate it. When the pressure is released at the proximal end of the apparatus, the bladder will deflate. In its deflated configuration (FIG. 36B), the bladder can be drawn back into a target array storage compartment 354 at the distal tip of rigid end section 352 in a similar manner to the operation of the flexible array described earlier. To facilitate this operation, operating tube 358 is preferably made of a flexible polymer, such as cross-linked polyethylene, which has adequate flexibility to allow flexible sheath 351 to bend as required, yet has considerable axial stiffness, so that bladder 362 may also be advanced and withdrawn as required.

It is extremely important that bladder 362 always be inflated to exactly the same diameter every time it is used, so that the relative positions of the target points on its outer surface are the same as when the target array was originally characterized. To insure this, the gauge pressure (i.e., the pressure above the background atmospheric pressure) of the gas is measured at the proximal end of flexible sheath 351 by an accurate pressure gauge (not shown) and this pressure is controlled by a precision pressure controller (also not shown). In addition, a temperature sensor, 364, is located at the distal end of the device near the bladder to monitor the temperature of the bladder. The temperature signal is returned to the proximal end of the device through temperature sensing wires 365 which run externally to rigid end section 352 to a wire entrance port 366. Entrance port 366 is located far enough back from the tip of end section 352 so that wires 365 lie behind tip plunger 353 when bladder 362 is fully withdrawn into storage compartment 354. Determination of the temperature of bladder 362 allows one to determine the correct internal pressure needed to compensate for change in the modulus of elasticity of the wall of bladder 362 as the temperature varies, so that inflation to the same size can be accomplished despite operation at various temperatures.

The reference target array shown in FIGS. 36A and 36B must be characterized with a fully three-dimensional measurement system. The preferred method and apparatus for characterization of the array is a multiple or moving camera perspective measurement system where the camera positions are oriented along a circular path, such as those described in U.S. Pat. No. 6,009,189 in the Section entitled "Embodiments Using Other Camera Motions", subsection C. While FIG. 35 implies that there are target points located all around convex shell 360, there is no requirement that this be the case. It is a simple matter to rotate the target array support 368 as required to bring a limited selection of targets into view, if the limited selection has all of the targets in one area of the surface of shell 360.

It is also not necessary that bladder 362 in FIG. 36 be more or less spherical as shown, or even that it be a convex shell. For instance bladder 362 could be in the form of a torus, so that objects of interest could be viewed through the hole in the torus, and so that reference target points could be located surrounding the object points of interest.

7. Reference Target Markings

In FIG. 37 are shown several alternative examples of the marks which can be used to denote the individual target points on a reference target array. The primary goal in selecting a particular type of mark is that the mark be able to repeatably be located, both during initial characterization of the array as well as during the perspective dimensional measurement.

An important fundamental principle to obtaining repeatable location of a mark by a human user is to make use of a symmetry of the mark in cooperation with the locating cursor. The reason for this is that the human visual system is much more sensitive to changes in symmetry than it is to changes in position. While my new system of measurement can be used with a machine vision system, I consider applications that rely on a human user to determine the positions of image points to be much more important for the present and near future.

Figure 37A:
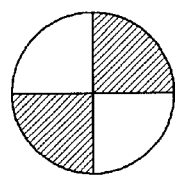
FIG. 37 depicts several alternative implementations of the marks denoting the target points in a reference target array.
Figure 37B:
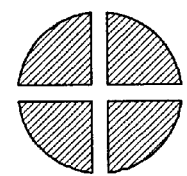

The mark of FIG. 37A is best used with the split cross-hair shown in FIGS. 10 and 11, while the mark of FIG. 37B is best used with the single cross-hair of FIG. 3. These marks are very precisely locatable during reference array characterization, because a cross-hair of a measurement microscope can be oriented to align with the axes of the marks. These marks are less desirable during perspective measurements, because the orientation of the axes of the marks is unlikely to align with the axes of the image measurement system, and because the distortion of the endoscope optical system will distort the apparent shape of the marks, thus reducing the symmetry. If such targets are used, they should appear to be rather small (say 0.5% to 5% of the size of the video screen height), because otherwise the distortion will change the position of the center as judged by the user.

Figure 37C:
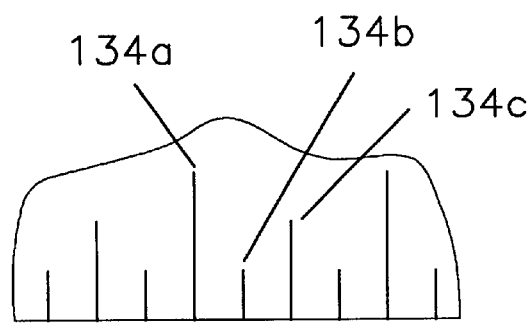

FIG. 37C depicts a fragment of a standard machinist's scale. This, by itself, can serve as a reference target array because a suitable set of tips of the indicia lines, e.g., those denoted as 134a, 134b, and 134c, are not colinear, and because the substrate is flat and stable. The advantages of using a machinist's scale as a reference target array are that these are readily available and that the user can instantly obtain an approximate indication of the size of the object before the measurement is made. The disadvantage is that the repeatability with which measurement cursors can be aligned to the tips of the indicia depends on the orientation of the indicia with respect to the axes of the cursors.

Figure 37D:
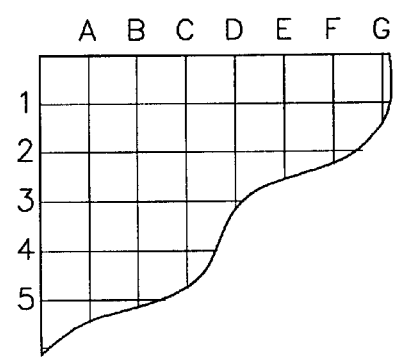

An easy way to obtain a large number of measurement reference target points is to use a grid, such as that depicted in FIG. 37D. Here the target points are marked by the intersections of the individual lines, and each point is designated by an intersection code, such as B3. Such marks are easy to precisely locate during characterization of the array, especially if one uses a split cross-hair like that shown FIG. 10. The same sort of cursor is preferred for measurements with these reference targets, but here the repeatability is not as good, both because the distortion of the endoscope optical system makes the grid lines appear curved, and because the orientation of the grid lines usually doesn't match the orientation of the measurement cursor. The marks that were shown in FIGS. 1 and 3 are alternate versions of the grid and have the same advantages and disadvantages.

Figure 37E:
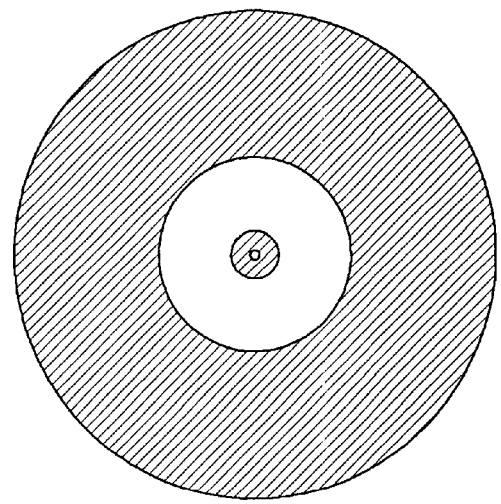

The target point mark that I prefer for general purpose use is shown in FIG. 37E. Here there are a series of concentric circles, with alternate annular regions filled with a color which contrasts with the background. If the radius of the smallest circle is taken as 1, then the radii of the larger circles can be, for instance, 5, 20, and 50 respectively. This target point mark is used with the split cross-hair cursor as was suggested in FIGS. 10 and 11 and is preferred for two reasons. First, target features of different scales are provided, so that an image size suitable for precision measurements is available over a wide range of distances between the reference target array and the camera. Second, the center of the circular feature is unambiguously identifiable no matter what the angular orientation of the target is with respect to the measurement cursor. The distortion of the camera's optical system will distort the circular shape, but the effect of this is minimized by using the circle with the appropriate size.

The preferred target point mark of FIG. 37E has the small disadvantage of being somewhat more difficult to precisely locate during the initial characterization of the array because typical measurement microscopes have a single cross-hair cursor. To minimize this problem, one could add a mark such as FIG. 37A or 37B at a very small scale in the center of the pattern, or one could replace the single cross-hair in the microscope with a reticle containing a circular cursor or a split cross-hair like that shown in FIG. 10.

The preferred target point mark is also preferred for machine vision applications of the system, because the location of the center of a circular boundary is relatively easy for a machine vision system using a modern image processing device. Even if machine vision is not used for field measurements, it makes a great deal of sense to use it for the characterization of the reference target array, if this is done at a factory. Field use of machine vision would be most advantageous in performing the step of locating the images of the reference target points, as opposed to locating the images of the object points, where the human user is much more capable. Such a partial use of machine vision in the measurement system would make the use of an uncalibrated camera in the measurement even more practical.

8. Generalized Embodiments of Measurement Apparatus

The embodiments described above show specific apparatus that can be used to make improved endoscopic measurements using the method of the present invention. In fact, a wide variety of different apparatus can be used to implement the method.

Figure 38:
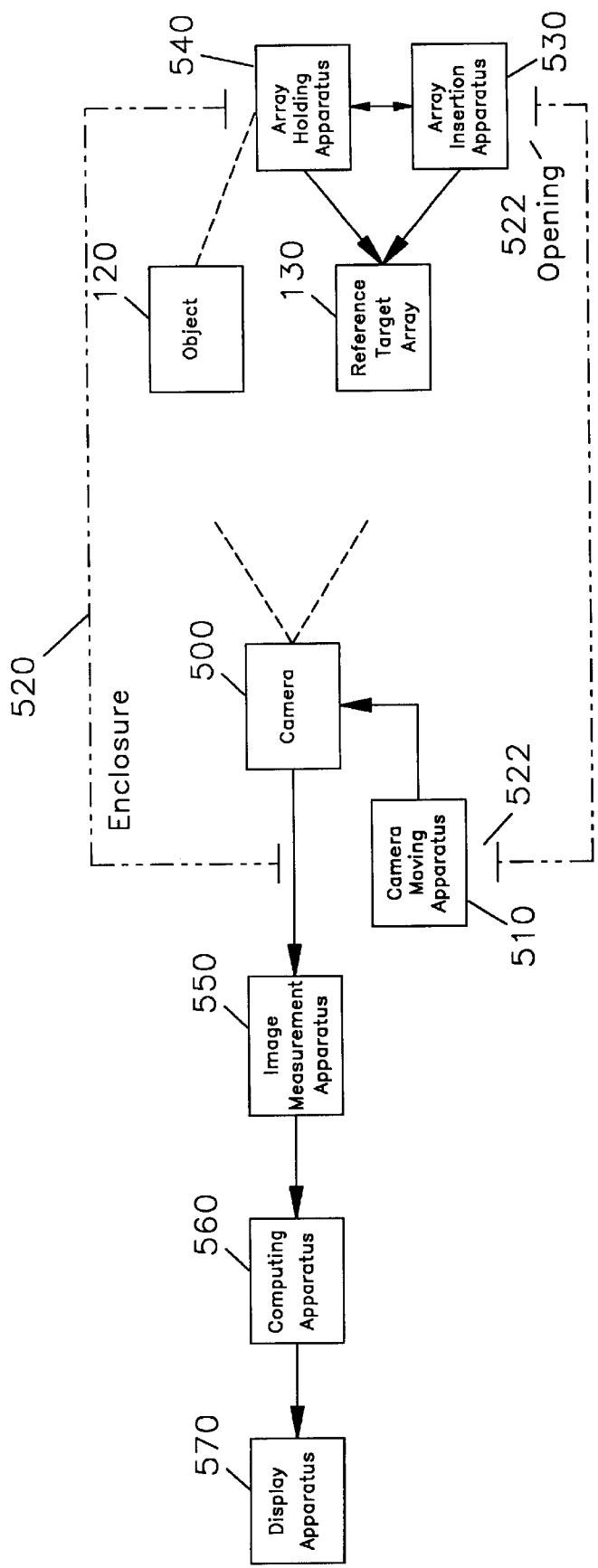
FIG. 38 shows a block diagram of a general embodiment of an apparatus for making a measurement according to the present invention.

In FIG. 38 is shown a block diagram of a general apparatus which can be used to practice the measurement. In FIG. 38 the position of a camera 500 is controlled by a camera moving apparatus 510. Camera 500 has been placed within an enclosure 520 which has one or more access openings 522. Camera 500 views object 120 which is also located inside enclosure 520. In FIG. 38 enclosure 520 is depicted as having two openings, but this is merely for convenience in the diagram. As explained above, a single opening is sufficient to make the measurement in many cases.

Camera 500 can be any sort of camera; it simply has to form an image of an object of interest 120. Camera moving apparatus 510 can be any sort of apparatus which allows the camera to assume more than one position with respect to the object. For instance, camera 500 could simply be rested on some structure internal to enclosure 520, and the camera could be lifted and moved from one position to the other by the user using the access provided by opening(s) 522. Camera moving apparatus 510 is depicted as being located partially inside and partially outside of enclosure 520 because, in general, it has components in both places. That is, the operator access to the moving apparatus is definitely outside of enclosure 520, whereas the mechanical interface to the optical portion of the camera is definitely inside the enclosure.

The key to the measurement is that camera 500 simultaneously forms images of reference target points on a reference target array 130 as it forms an image of object 120. A reference array holding apparatus 540 serves to hold reference target array 130 fixed with respect to object 120. This relationship is indicated by the broken line drawn between object 120 and array holding apparatus 540.

Reference target array holding apparatus 540 can be any apparatus that is capable of holding array 540 fixed in position and orientation with respect to object 120. For instance, if object 120 is so oriented and the area of interest is so located, one could simply provide a pair of hooks or brackets on reference target array 130 so that array 130 could either be hung from the top of object 120 or rested upon its top surface. In other cases, other techniques, such as magnets, could be used to attach reference array 130 directly to object 120 at positions other than its top. In all of these cases, the intent is that reference array 130 is positioned so as not to obscure the view of the points of interest on object 120.

Reference target array 130 is also shown connected to an array insertion apparatus 530, and array insertion apparatus 530 is also shown as having a connection to array holding apparatus 540. The meaning of this is as follows. Array holding apparatus 540 is considered to be ultimately responsible for the connection of reference target array 130 either to a structure which is fixed with respect to object 120 or to object 120 itself. However, array 130 may be supported indirectly through an insertion apparatus 530, and not directly by holding apparatus 540. An example is where the reference array is mounted to a wire, and where the wire is, in turn, supported by a fixture at the inspection port. In other cases, array holding apparatus 540 will be such as to attach directly to object 120, and the reference target array will then attach directly to holding apparatus 540. In this case, array insertion apparatus 530 is used to insert both array holding apparatus 540 and reference array 130 through opening 522. They may be inserted together as an assembly, or one at a time, with the assembly accomplished inside of enclosure 520 using insertion apparatus 530.

Both array holding apparatus 540 and array insertion apparatus 530 are depicted as lying partially inside and partially outside of enclosure 520. The meaning of this is that in any individual case, at least one of holding apparatus 540 and insertion apparatus 530 has a portion that lies inside of enclosure 520 and at least one of them has a portion that lies outside of enclosure 520.

As shown above by specific embodiments, in some cases, array insertion apparatus 530 cooperates with target array 130 to reduce the cross-section of array 130 during insertion through opening 522.

Camera moving apparatus 510 has not been shown as being comprised of both a camera holding apparatus and a camera moving apparatus because the camera does not necessarily have to be held fixed with respect to object 120. All that is required is that any motion of the camera be negligible over the exposure time necessary to acquire an image. In the endoscopic application, camera 500 need not have a specific support mechanism and, in fact, often will not have one. Just the simple fact that a flexible endoscope has been passed through a complicated path inside a structure in order to reach a viewing position is often enough to provide adequate stability to the image, even if a frame grabber is not used.

The image formed by camera 500 is measured with image measurement apparatus 550. Measurement data from measurement apparatus 550 is supplied to a computing apparatus 560 in which the required calculations, detailed in Section 2, above, are carried out. Clearly, either or both of image measurement apparatus 550 and computing apparatus 560 could lie inside of enclosure 520 as well as outside as depicted. Finally, the apparatus comprises a display apparatus, 560, which displays the results of the calculation to the user. The concept of the system is that display apparatus 570 must lie outside of enclosure 520 where it can be viewed by the user.

Enclosure 520 is most often a preexisting mechanical structure, but in the case of medical applications, it is a living body. In that case opening 522 may be either a natural opening in the body, or it may be an opening created surgically.

Figure 39:
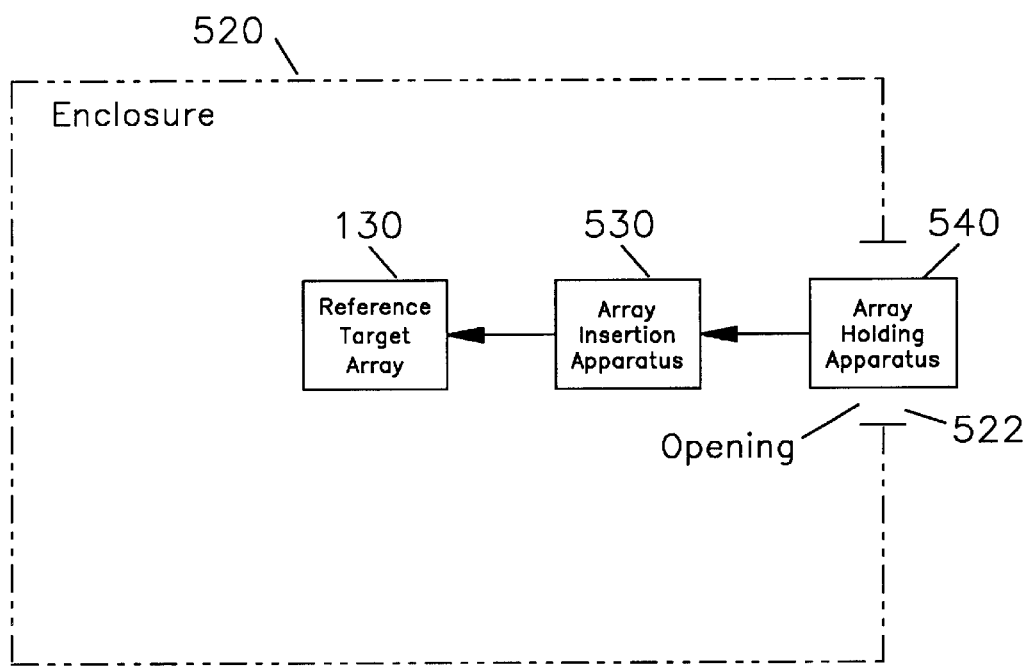
FIG. 39 shows a block diagram of a general embodiment of a measurement reference apparatus according to the present invention.

FIG. 39 shows a block diagram of a general apparatus for providing an array of reference points for making either perspective dimensional measurements or photogrammetric measurements of objects located inside an enclosure according to the present invention. In FIG. 39 an enclosure 520 includes an opening 522. Shown in the opening is an array holding apparatus 540. Array holding apparatus 540 is shown lying partially inside and partially outside of enclosure 520 because it attaches to a reference structure that is either the wall of enclosure 520 or some structure outside of enclosure 520. As stated previously, for this to be useful, reference array 130 must remain fixed with respect to an object of interest located inside the enclosure; thus holding apparatus 540 must attach to some structure that is fixed with respect to that object of interest.

Note that if a particular application permits it, array holding apparatus could attach to more than one opening in enclosure 520. This would be advantageous in those situations where the wall of enclosure 520 has little ability to resist force or torque.

Array holding apparatus 540 supports an array insertion apparatus 530 which, in turn, supports a reference target array 130. Array insertion apparatus 530 can be, for instance, as simple as a wire or as complicated as the apparatuses depicted in FIGS. 29–31 and 36. Array insertion apparatus 530 cooperates with array holding apparatus 530 to position target array 130 near to an object of interest with an orientation suitable for making either perspective dimensional measurements or photogrammetric measurements as desired.

Using photogrammetry and the apparatus depicted in FIG. 39, one can make an endoscopic measurement using more than the two views specified by my perspective dimensional measurement process. As discussed with reference to the prior art, one might want to do this if one were interested in extremely precise measurements of the object and/or if one wanted to characterize a large number of dimensions on the object. In photogrammetry, the process of determining the spatial position and orientation of a camera from image data is known as "resection". The process of determining the position of a point in space from two images is known as "intersection". The process of determining both the locations of object points and the camera locations and orientations, especially when there are more than two camera stations (views), is known as "bundle adjustment". Details can be found, for instance, in the book *Close Range Photogrammetry and Machine Vision*, K. B. Atkinson, ed., Whittles Publishing, Bristol, England, 1996.

CONCLUSIONS, RAMIFICATIONS, AND SCOPE

Accordingly, the reader will see that the improved system of this invention has many advantages over the prior art and solves the problems previously identified. My system produces true three-dimensional measurements, and it does this without requiring contact with the object in any manner. It can be used with any endoscope without requiring any modifications to it, therefore it does not interfere with insertion or withdrawal of an endoscope through an access port.

My system can take an existing ordinary two-dimensional endoscopic measurement system and produce a three-dimensional measurement without requiring any change to the apparatus of the original system. Implementation of my system does not require an image processing device; one simply makes a few additional ordinary two-dimensional measurements and applies a relatively simple process to the measurements to determine the desired three-dimensional data.

The system can be made self-calibrating, that is, the camera need not be calibrated in a separate setup. Because of this, accurate measurements can be obtained even if the magnification of the camera changes as its focus is adjusted.

My system makes use of a reference object, but it is superior to those systems in which a dimensional scale is compared to the inspection object because in my system the reference object need not be precisely located with respect to the inspection object, because the endoscope need not have a particular orientation with respect to the inspection object or the reference object, and because the shape of the reference object need not match the shape of the inspection object.

Embodiments have been shown that provide a variety of apparatus that enable endoscopic measurements to be made in a wide range of situations. Although the invention has been described with reference to these particular embodiments, it will be understood by those skilled in the art that the invention is capable of a variety of alternative embodiments within the spirit and scope of the appended claims.

For instance, while the embodiments shown use a video camera and a video measurement system, one can also use other known image measurement systems, such as photography, or a filar micrometer. If the images formed by the camera are recorded, for instance in digital form with a frame grabber, it is possible to make additional measurements on an object at a later time, after the initial image acquisition, simply by recalling the images and repeating the measurement process. One need not keep a record of the calibration of the camera (if a sufficient number of reference points are included in the images), but does need a record of the characterization of the reference target array.

As mentioned, the system can be used for medical purposes where the object of interest is enclosed inside a living body. In this case, a reference target array like the one shown in FIG. 36 will be preferred. It is undesirable to introduce a sharp, rigid object into a living body, and most of the embodiments shown have both of these characteristics. To obtain an accurate measurement, the reference target array must accurately maintain its size and shape, or accurately recover that size and shape if it gets distorted. With a non-inflatable reference array this stability requirement can be met in the medical application by marking the array on the outer surface of a spherical, elliptical, or similarly shaped shell (or partial shell) made of an elastomeric material. The stability of array size and shape is provided by the shell structure, the flexibility by the fact that it is made of elastomer. Such a reference array can distort when necessary to pass through body openings, yet recover its shape accurately for a measurement.

Returning to more general considerations, there is no requirement that the target array points all be constrained to lie on flat surfaces of the reference target array. That is, the target array could be implemented as, for instance, a space frame of points where the points are indicated by spherical bodies. This has the advantage that the array could be viewed from any angle. Use of ceramic balls for such points is preferred because they are rugged and they do not require a surface treatment to exhibit a diffuse reflection characteristic.

It is also possible for three-dimensional reference target arrays to be fabricated with a great deal of depth; for instance, two of the conventional arrays I have shown could be attached together, separated by a significant distance. To make best use of such an array one would position it so that some of the reference targets are located in front of the object of interest and others are located behind it. This then would offer the ultimate in measurement accuracy, especially in those cases where an uncalibrated camera is used. The disadvantage is the cost of the three-dimensional metrology required for characterizing such an array.

The embodiments discussed in detail illustrate apparatus for measurement that use rigid borescopes and flexible endoscopes that have internal articulation. It was discussed how the measurement can be made using any motion of the camera that meets the requirement on subtended angle. With a flexible endoscope that lacks internal articulation one way to produce a suitable motion is to place the endoscope into a flexible guide tube and use the articulation provided by the guide tube.

In U.S. Pat. No. 6,009,189 I taught two new instruments, the electronic measurement endoscope and the electronic measurement borescope. With the system of the instant invention, it is possible to make accurate measurements with these instruments if they lose their internal calibrations.

The specific embodiments shown for holding devices for rigid borescopes all refer to inspection ports that have threaded openings. It is also possible to use the system with other types of inspection ports, such as those that are covered with a plate mounted with multiple screws.

In my system the measurement accuracy is determined by the accuracy with which the reference array is characterized and by the precision with which the reference points and object points can be located in the images, and not by the precision of the motion of the camera. Thus my system of determining camera positions and orientations in three dimensions could be used to improve surface contouring systems such as that of Tsujiuchi, et. al., U.S. Pat. No. 4,895,431, in that they would no longer require that an accurately determined motion of the contouring camera be generated.

I claim:

1. An apparatus for measuring three-dimensional distances between individual points on an object, said object being located inside an enclosure, said enclosure having an interior and an exterior and having a wall located therebetween, said wall having at least one opening therein through which the interior of the enclosure can be accessed, comprising:
   (a) a camera for forming an image, said camera being located inside the enclosure;
   (b) means for moving the camera in a spatial relationship with respect to the object;
   (c) an array of reference target points having at least three non-colinear target points, said target points having locations characterized in a reference coordinate system;
   (d) means for inserting said array of reference target points through one of said at least one opening from the exterior to the interior of the enclosure;
   (e) means for holding said array in a fixed spatial relationship with respect to the object, said means for holding being cooperatively engaged with said means for inserting and with the array whereby said array is disposed at a position near to and fixed with respect to said object;
   (f) means for measuring the positions of points in an image formed by the camera;
   (g) means for computing, said means for computing receiving measurements from said means for measuring, said means for computing being further adapted to compute the three dimensional distances between said individual points on said object; and
   (h) means for displaying the results of the measurement computations.

2. The apparatus of claim 1 wherein the camera is incorporated into an endoscope, said endoscope having a distal portion that is inserted through an access port in said wall.

3. The apparatus of claim 2 wherein the endoscope is flexible and wherein said means for moving comprises means for variably bending a section of said endoscope.

4. The apparatus of claim 3 wherein said means for variably bending comprises an endoscope guide tube having an articulation means.

5. The apparatus of claim 3 wherein said means for variably bending comprises an internal articulation means of said endoscope.

6. The apparatus of claim 2 wherein the endoscope has a length and wherein said means for moving comprises means to translate the endoscope in a direction substantially oriented along its length.

7. The apparatus of claim 2 wherein the endoscope is rigid and has a length and wherein said means for moving comprises means to rotate the endoscope about an axis, said axis being located near said access port and said axis being oriented substantially perpendicular to said length.

8. The apparatus of claim 2 wherein said means for holding is adapted to hold both the endoscope and said means for inserting and wherein said means for holding is attached to said wall.

9. The apparatus of claim 2 wherein said means for holding comprises an endoscope guide tube.

10. The apparatus of claim 1 wherein said means for inserting comprises a wire.

11. The apparatus of claim 10 wherein said wire is coated with a dissipative polymer.

12. The apparatus of claim 10 wherein said means for holding comprises means for clamping said wire to the wall of the enclosure.

13. The apparatus of claim 10 wherein said means for holding comprises an endoscope guide tube.

14. The apparatus of claim 1 wherein said means for holding comprises an endoscope being held fixed with respect to the object.

15. The apparatus of claim 1 wherein said array of reference target points is rotatably attached to said means for inserting and wherein said means for inserting further comprises means for disposing the array at a selectable angular orientation with respect to said means for inserting.

16. The apparatus of claim 15 further comprising means for selecting the angular orientation of the array from the exterior of the enclosure.

17. The apparatus of claim 1 further comprising array collapsing means and array expanding means, said array being collapsed to a small cross-section for insertion and expanded to an operating configuration after insertion.

18. The apparatus of claim 17 wherein said array collapsing means comprises an auxiliary insertion tool.

19. The apparatus of claim 17 wherein said means for inserting comprises both said array collapsing means and said array expanding means.

20. The apparatus of claim 17 wherein said reference target points are marked on an outer surface of an inflatable bladder.

21. The apparatus of claim 20 further comprising a temperature sensor for measurement of a temperature of said bladder.

22. The apparatus of claim 1 wherein said reference target points are marked on a plane surface.

23. The apparatus of claim 22 wherein the plane surface is a surface of a rigid body.

24. The apparatus of claim 22 further comprising at least one indicium marked on said array of reference target points, said indicium being adapted to provide a-priori information about the spatial location of said camera with respect to said array when said indicium appears in said image.

25. The apparatus of claim 22 wherein the plane surface is a flexible membrane being stretched to conform to a plane.

26. The apparatus of claim 1 wherein said array of reference target points contains at least four target points and wherein at least one target point lies outside of a plane defined by three other target points.

27. The apparatus of claim 26 further comprising two parallel planes spaced apart along their mutual perpendicular, both of the planes having reference target points marked thereupon, and at least one of the planes being adapted to allow target points marked on the other plane to be visible when target points marked upon itself are visible.

28. The apparatus of claim 26 wherein said reference target points are marked on at least two of three planar adjacent sides of a three-dimensional surface, said three planar adjacent sides meeting in a corner.

29. The apparatus of claim 26 further comprising a plane surface marked with at least three reference target points, and a post having a visible end, said post being mounted substantially perpendicular to the plane surface, and said post being marked with a reference target point at said visible end.

30. The apparatus of claim 26 further comprising an inflatable bladder, said reference target points being marked on an outer surface of said bladder.

31. The apparatus of claim 1 wherein said array of reference target points comprises a plurality of sets of reference target points, at least two of the sets being spaced apart by a distance approximately equal to a distance of interest on the object, whereby a mode 2 perspective dimensional measurement can be made of the distance of interest.

32. A reference apparatus for providing reference information in making three-dimensional distance measurements on an object located inside of an enclosure, said enclosure having an interior and an exterior and having a wall located therebetween, said wall having at least one opening therein through which the interior of the enclosure can be accessed, comprising:

(a) an array of reference target points having at least three non-colinear target points, said target points having locations characterized in a reference coordinate system;

(b) array insertion apparatus cooperatively engaged with said array of target reference points, whereby the array of target reference points is inserted through one of said at least one opening from the exterior to the interior of the enclosure; and (c) array holding apparatus adapted to being fixed in position with respect to the object, said array holding apparatus being cooperatively engaged with the insertion apparatus and with the array of target reference points, whereby said array of target reference points is disposed at a position near to and fixed with respect to said object.

33. The apparatus of claim 32 wherein said array insertion apparatus comprises a wire.

34. The apparatus of claim 33 wherein said array holding apparatus comprises means for clamping said wire to the wall of the enclosure.

35. The apparatus of claim 32 wherein said array of reference target points is rotatably attached to said array insertion apparatus and wherein said insertion apparatus further comprises means for disposing the array at a selectable angular orientation with respect to said insertion apparatus.

36. The apparatus of claim 32 further comprising array collapsing means and array expanding means, said array being collapsed to a small cross-section for insertion and expanded to an operating configuration after insertion.

37. The apparatus of claim 32 wherein said array of reference target points contains at least four target points and wherein at least one target point lies outside of a plane defined by three other target points.

38. A method for determining three-dimensional coordinates for at least one object point on an object, thereby determining a location vector for each of said at least one object point, said object being located inside an enclosure, said enclosure having an interior, said enclosure also having at least one opening through which its interior can be accessed, comprising the steps of:

(a) inserting a camera for forming and acquiring images through an opening in the enclosure;

(b) inserting a reference target array through an opening in the enclosure;

(c) disposing the reference target array at a position sufficiently near to said at least one object point that said at least one object point and at least a portion of said reference target array can both be contained in a single image formed by the camera;

(d) holding the reference target array fixed in position with respect to said object;

(e) moving the camera successively to at least two viewing positions with respect to said object, at least two of said at least two viewing positions being separated sufficiently so that an angle subtended by these positions at each of said at least one point on the object is substantially different from zero;

(f) acquiring images containing said at least one object point and at least a portion of said reference target array at each of said at least two viewing positions; and (g) determining, from the images, the three-dimensional coordinates of said at least one object point in a reference coordinate system defined by the reference target array.

39. The method of claim 38 wherein the step of inserting a reference target array comprises the steps of collapsing the reference target array to a small cross-section, inserting it through an opening while it is in the collapsed configuration, and expanding the array to an operating configuration once it is inserted.

40. The method of claim 38 wherein the camera is an endoscope and wherein the step of moving the camera comprises the step of bending a distal portion of the endoscope.

41. The method of claim 38 wherein the camera is an endoscope having a length and wherein the step of moving the camera comprises the step of translating the endoscope along its length.

42. The method of claim 38 wherein the camera is a rigid endoscope having a length and wherein the step of moving the camera comprises the step of rotating the endoscope about an axis substantially perpendicular to its length.

43. The method of claim 38 wherein the step of holding the reference target array comprises the step of clamping or securing the reference target array to the enclosure.

44. The method of claim 38 wherein two viewing positions are used and wherein the step of determining comprises a perspective dimensional measurement process.

45. The method of claim 38 wherein the step of determining comprises a photogrammetric process.

46. The method of claim 38 for determining the three-dimensional distances between the points of each pair of any set of pairs of points in a plurality of points on an object, comprising the steps of:

(h) performing steps (a) through (g) of claim 38 for said plurality of points;

(i) determining a difference vector between the location vectors of a first pair of said set of pairs of points by subtracting the location vector of a first point of said pair from the location vector of the second point of said pair;

(j) determining the length of the difference vector by calculating the square root of the sum of the squares of the components of the difference vector; and (k) repeating steps (i) and (j) as necessary to determine the distances between the points of all remaining pairs in said set of pairs of points.

47. The method of claim 38 for determining the three-dimensional distance between a pair of object points on an object, comprising the steps of:

(h) performing steps (a) through (g) of claim 38 for a first point of said pair of object points;

(i) transforming the three-dimensional coordinates for said first point to said reference coordinate system;

(j) performing steps (e) through (g) of claim 38 for a second point of said pair of object points;

(k) transforming the three-dimensional coordinates for said second point to said reference coordinate system; and (l) calculating the length of the difference vector between the three-dimensional coordinates of said first point and said second point.

* * * * *